US011833198B2

(12) United States Patent
Tan et al.

(10) Patent No.: US 11,833,198 B2
(45) Date of Patent: Dec. 5, 2023

(54) NOROVIRUS S PARTICLE BASED VACCINES AND METHODS OF MAKING AND USING SAME

(71) Applicant: Children's Hospital Medical Center, Cincinnati, OH (US)

(72) Inventors: Ming Tan, Cincinnati, OH (US); Xi Jason Jiang, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 465 days.

(21) Appl. No.: 16/489,095

(22) PCT Filed: Mar. 15, 2018

(86) PCT No.: PCT/US2018/022552
§ 371 (c)(1),
(2) Date: Aug. 27, 2019

(87) PCT Pub. No.: WO2018/182983
PCT Pub. Date: Oct. 4, 2018

(65) Prior Publication Data

US 2020/0069787 A1 Mar. 5, 2020

Related U.S. Application Data

(60) Provisional application No. 62/477,481, filed on Mar. 28, 2017.

(51) Int. Cl.

| | |
|---|---|
| ***A61K 39/12*** | (2006.01) |
| ***A61P 31/14*** | (2006.01) |
| ***A61K 39/385*** | (2006.01) |
| ***C07K 14/005*** | (2006.01) |
| ***C12N 7/00*** | (2006.01) |
| *A61K 39/00* | (2006.01) |

(52) U.S. Cl.
CPC ............ *A61K 39/12* (2013.01); *A61K 39/385* (2013.01); *A61P 31/14* (2018.01); *C07K 14/005* (2013.01); *C12N 7/00* (2013.01); *A61K 2039/6075* (2013.01); *A61K 2039/64* (2013.01); *A61K 2039/70* (2013.01); *C07K 2319/33* (2013.01); *C12N 2770/16022* (2013.01); *C12N 2770/16034* (2013.01)

(58) Field of Classification Search
None
See application file for complete search history.

(56) References Cited

U.S. PATENT DOCUMENTS

| | | | |
|---|---|---|---|
| 4,547,367 | A | 10/1985 | Tabor et al. |
| 4,550,019 | A | 10/1985 | Polson |
| 4,916,213 | A | 4/1990 | Scannon et al. |
| 5,254,342 | A | 10/1993 | Shen et al. |
| 5,326,857 | A | 7/1994 | Yamamoto et al. |
| 5,338,689 | A | 8/1994 | Yves et al. |
| 5,367,054 | A | 11/1994 | Lee |
| 5,559,014 | A | 9/1996 | Estes et al. |
| 5,589,453 | A | 12/1996 | Greve |
| 5,643,579 | A | 7/1997 | Hung et al. |
| 5,665,534 | A | 9/1997 | Vandenbergh et al. |
| 5,750,394 | A | 5/1998 | Palese et al. |
| 5,783,193 | A | 7/1998 | Michael et al. |
| 5,786,340 | A | 7/1998 | Henning et al. |
| 5,789,230 | A | 8/1998 | Cotton et al. |
| 5,861,241 | A | 1/1999 | Herrmann et al. |
| 6,045,854 | A | 4/2000 | Prieto et al. |
| 6,130,205 | A | 10/2000 | Stapleton et al. |
| 6,140,043 | A | 10/2000 | Dierich et al. |
| 6,156,883 | A | 12/2000 | Estes et al. |
| 6,187,762 | B1 | 2/2001 | Mandeville, III et al. |
| 6,254,867 | B1 | 7/2001 | Reiser et al. |
| 6,258,789 | B1 | 7/2001 | German et al. |
| 6,300,090 | B1 | 10/2001 | Steinman et al. |
| 6,303,369 | B1 | 10/2001 | Spana et al. |
| 6,475,489 | B1 | 11/2002 | Rutter et al. |
| 6,572,862 | B1 | 6/2003 | Estes et al. |
| 6,593,080 | B1 | 7/2003 | Smith |
| 6,942,865 | B2 | 9/2005 | Estes et al. |
| 6,946,266 | B2 | 9/2005 | Neiman |
| 7,527,801 | B2 | 5/2009 | Coit et al. |
| 7,785,871 | B2 | 8/2010 | Reed |
| 7,893,041 | B2 | 2/2011 | Morrow et al. |

(Continued)

FOREIGN PATENT DOCUMENTS

| | | | |
|---|---|---|---|
| CN | 1330080 | A | 1/2002 |
| GB | 2535753 | A | 8/2016 |

(Continued)

OTHER PUBLICATIONS

Xia et al., Vaccine vol. 34, pp. 905-913 (Year: 2016).*
European Search Report, Supplementary, and Written Opinion dated Jan. 13, 2021 for Application No. EP 18777340.3, 8 pgs.
Adler, et al., "High Affinity Binding of the *Entamoeba histolytica* Lectin to Polyvalent *N*-Acetylgalactosaminides," J Bio Chem, 1995, 270(10):5164-5171, 8 pgs.
Affixed, definition of, WordReference.com, English Dictionary, searched on Jan. 16, 2010, corresponding U.S. Appl. No. 11/264,992, 1 pg.
Akita, E.M., et al., "Immunoglobulins from Egg Yolk: Isolation and Purification," Journal of Food Science, 1992, 57:629-634, 6 pgs.

(Continued)

*Primary Examiner* — Shanon A. Foley
*Assistant Examiner* — Myron G Hill
(74) *Attorney, Agent, or Firm* — Frost Brown Todd LLP

(57) ABSTRACT

Disclosed herein are vaccine compositions, in particular, polyvalent icosahedral compositions for antigen presentation. The disclosed compositions may contain an S particle made up of recombinant fusion proteins. The recombinant fusion proteins may include a norovirus (NoV) S domain protein, a linker protein domain operatively connected to the norovirus S domain protein, and an antigen protein domain operatively connected to said linker.

18 Claims, 10 Drawing Sheets

Specification includes a Sequence Listing.

(56) References Cited

U.S. PATENT DOCUMENTS

| | | | |
|---|---|---|---|
| 7,912,484 | B2 | 3/2011 | Sohn et al. |
| 7,955,603 | B2 | 6/2011 | Richardson et al. |
| 7,977,098 | B2 | 7/2011 | Jiang et al. |
| 8,026,221 | B2 | 9/2011 | Jiang et al. |
| 8,066,998 | B2 | 11/2011 | Frye et al. |
| 8,277,819 | B2 | 10/2012 | Jiang et al. |
| 8,475,789 | B2 | 7/2013 | Bisgaard-Frantzen et al. |
| 8,486,421 | B2 | 7/2013 | Jiang et al. |
| 8,895,015 | B2 | 11/2014 | Vesikari et al. |
| 9,096,644 | B2 | 8/2015 | Tan et al. |
| 9,321,803 | B2 | 4/2016 | Jiang et al. |
| 9,395,986 | B2 | 7/2016 | Miyoshi et al. |
| 9,561,239 | B2 | 2/2017 | Jiang et al. |
| 9,562,077 | B2 | 2/2017 | Tan et al. |
| 9,701,735 | B2 | 7/2017 | Starzl |
| 10,065,994 | B2 | 9/2018 | Settembre et al. |
| 2002/0019991 | A1 | 2/2002 | Prieto et al. |
| 2006/0057562 | A1 | 3/2006 | Jiang et al. |
| 2007/0231320 | A1 | 10/2007 | Cook et al. |
| 2007/0280949 | A1 | 12/2007 | Alfa |
| 2008/0085553 | A1 | 4/2008 | Reed et al. |
| 2011/0152263 | A1 | 6/2011 | Jiang et al. |
| 2011/0166328 | A1 | 7/2011 | Nguyen |
| 2012/0009211 | A1 | 1/2012 | Tschopp et al. |
| 2012/0020964 | A1 | 1/2012 | Frye et al. |
| 2012/0071436 | A1 | 3/2012 | Jiang et al. |
| 2013/0171185 | A1 | 7/2013 | Settembre et al. |
| 2014/0017257 | A1 | 1/2014 | Jiang et al. |
| 2014/0302079 | A1 | 10/2014 | Nabel et al. |
| 2016/0038586 | A1 | 2/2016 | Lin et al. |
| 2016/0222066 | A1* | 8/2016 | Settembre .............. A61K 39/12 |

FOREIGN PATENT DOCUMENTS

| | | | |
|---|---|---|---|
| JP | 2012-529298 | A | 11/2012 |
| JP | 2013-533745 | A | 8/2013 |
| JP | 2015-201119 | A | 11/2015 |
| WO | WO 01/08677 | A1 | 2/2001 |
| WO | WO 02/30409 | A2 | 4/2002 |
| WO | WO 2003/003985 | A2 | 1/2003 |
| WO | WO 2003/101176 | A2 | 12/2003 |
| WO | WO 2005/030806 | A2 | 4/2005 |
| WO | WO 2005/032457 | A2 | 4/2005 |
| WO | WO 2006/138514 | A2 | 12/2006 |
| WO | WO 2007/020017 | A1 | 2/2007 |
| WO | WO 2007/103162 | A2 | 9/2007 |
| WO | WO 2010/144602 | A2 | 12/2010 |
| WO | WO 2011/120044 | A1 | 9/2011 |
| WO | WO 2016/019890 | A1 | 2/2016 |

OTHER PUBLICATIONS

Akita, E.M., et al., "Production and purification of Fab' fragments from chicken egg yolk immunoglobulin Y (IgY)," J Immunol Methods, 1993, 162:155-164, 10 pgs.

Amaral, J.A., et al., "Anti-enteropathogenic *Escherichia coli* immunoglobulin Y isolated from eggs laid by immunized Leghorn chickens," Res Vet Sci, 2002, 72:229-234, 6 pgs.

Ando, H.Y., et al., "Property-Based Drug Design and Preformulation," in Troy, D.B. (ed.), et al., *Remington, The Science and Practice of Pharmacy*, 21st Ed., Lippincott Williams & Wilkins, Philadelphia, PA, 2006, pp. 720-723, 10 pgs.

Armah, G.E., et al., "Efficacy of pentavalent rotavirus vaccine against severe rotavirus gastroenteritis in infants in developing countries in sub-Saharan Africa: a randomised, double-blind, placebo-controlled trial," Lancet, 2010, 376:606-614, 9 pgs.

Assay, definition of, http://encycolpedia_thefreedictionary.com/assay, corresponding U.S. Appl. No. 11/264,992, printed on Feb. 22, 2008, p. 1-5, 5 pgs.

Atmar, R., et al., "Diagnosis of Noncultivatable Gastroenteritis Viruses, the Human Caliciviruses," Clinical Microbiology Reviews, 2001, 14(1):15-37, 24 pgs.

Barcena, J., et al., "The coat protein of Rabbit hemorrhagic disease virus contains a molecular switch at the N-terminal region facing the inner surface of the capsid," Virol, 2004, 322(1):118-134, 17 pgs.

Bauchau, V., et al., "Post-marketing monitoring of intussusception after rotavirus vaccination in Japan," Pharmacoepidemiology and Drug Safety, 2015, 24:765-770, 6 pgs.

Bereszcazk, J.Z., et al., "Structure, stability and dynamics of norovirus P domain derived protein complexes studied by native mass spectrometry," Journal of Structural Biology, 2012, 177(2):273-282, 10 pgs.

Bertolotti-Ciarlet, A., et al., "Structural Requirements for the Assembly of Norwalk Virus-Like Particles," J Virol, 2002, 76(8):4044-4055, 12 pgs.

Biesiada, J., et al., "On Setting Up and Assessing Docking Simulations for Virtual Screening," Chapter 1, In: Yi Zheng (ed.), *Rational Drug Designs: Methods and Protocols*, Methods in Molecular Biology, 2012, 928:1-16, 16 pgs.

Biesiasa, J., et al., "Survery of public domain software for docking simulations and virtual screening," Human Genomics, 2011, 5:497-505, 9 pgs.

Brinker, J.P., et al., "Immunoglobulin M Antibody Test to Detect Genogroup II Norwalk-Like Virus Infection," Journal for Clinical Microbiology, 1999, 37(9):2983-2986, 4 pgs.

Bruss, V., et al., "Mutational Analysis of Hepatitis B Surface Antigen Particle Assembly and Secretion," J Virol, 1991, 65(7):3813-3820, 8 pgs.

Bu, W., et al., "Structural Basis for the Receptor Binding Specificity of Norwalk Virus," J Virol, 2008, 82(11):5340-5347, 8 pgs.

Burmeistr, W.P., et al., "Structure Determination of Feline Calicivirus Virus-Like Particles in the Context of a Psuedo-Octahedral Arrangement," PLoS One, 2015, 10(3):e0119289, 15 pgs.

Burton-MacLeod, J.A., et al., "Evaluation and Comparison of Two Commerical Enzyme-Linked Immounosorbent Assay Kits for Detection of Antigenically Diverse Human Noroviruses in Stool Samples," Journal of Clinical Microbiology, 2004, 42(6):2587-2595, 9 pgs.

Cao, S., et al., "Structural Basis for the Recognition of Blood Group Trisaccharides by Norovirus," J Virol, 2007, 81(11):5949-5957, 9 pgs.

Capua et al., "Control and prevention of avian influenza in an evolving scenario," Vaccine, 2007, 25:5645-5652, 8 pgs.

Cavasotto, C.N., et al., "Ligand Docking and Structure-based Virtual Screening in Drug Discovery," Current Topics in Medicinal Chemistry, 2007, 7:1006-1014, 9 pgs.

Center for Disease Control and Prevention Information Page, Norovirus Illness: Key Facts—Treatment, 2015, Accessed online on Feb. 9, 2015 at «http://www.cdc.gov/norovirus/about/treatment.html», 1 pg.

Centers for Disease Control and Prevention Information Page, Norovirus: Q&A, Accessed online Sep. 29, 2010, at «https://www.cdc.gov/ncidod/dvrd/revb/gastro/norovirus-qa.htm», 3 pgs.

Center for Disease Control and Prevention Information Page, Rotavirus Vaccination, Accessed online on Feb. 9, 2015 «http://www.cdc.gov/vaccines/vpd-vac/rotavirus/default.html», 3 pgs.

Chakravarty et al., "Evolutionary Trace Residues in Noroviruses: Importance in Receptor Binding, Antiagenicity, Virion Assembly, and Strain Diversity," J Virol, Jan. 2005, 79(1):554-568, 15 pgs.

Chang, D.T., et al., "MEDock: a web server for efficient prediction of ligand binding sites based on a novel optimization algorithm," Nucleic Acids Res, 2005, 33:W233-W238, 6 pgs.

Chatterji, A., et al., "Chemical Conjugation of Heterologous Proteins on the Surface of Cowpea Mosaic Virus," Bioconjugate Chem, 2004, 15:807-813, 7 pgs.

Chatterji, A., et al., "Cowpea Mosaic Virus: From the Presentation of Antigenic Peptides to the Display of Active Biomaterials," Intervirology, 2002, 45(4-6):362-380, 9 pgs.

Chen, C., et al., "Nanoparticle-Templated Assembly of Viral Protein Cages," Nano Lett, 2006, 6(4):611-615, 5 pgs.

Chen, C., et al., "Packaging of Gold Particles in Viral Capsids," J Nacosci Nanotechnol, 2005, 5:2029-2033, 5 pgs.

Chen, J.H., et al., "ChemDB update—full-text search and virtual chemical space," Bioinformatics, 2007, 23(17):2348-2351, 4 pgs.

(56) References Cited

OTHER PUBLICATIONS

Chen, R., et al., "Inter-and Intragenus Structural Variation in Caliciviruses and Their Functional Implications", J Virol, Jun. 2004, 78(12):6469-6479, 11 pgs.
Chen, X.S., et al., "Structure of Small Virus-like Particles Assembled from the L1 Protein of Human Paillomavirus 16," Mol Cell, 2000, 5:557-567, 11 pgs.
Chen, Y., et al., "Crystallography of a Lewis-Binding Norovirus, Elucidation of Strain-Specificity to the Polymorphic Human Histo-Blood Group Antigens," PLoS Pathog, 2011, 7(7):e1002152, 14 pgs.
Choi, A.H-C., et al. "Functional Mapping of Protective Domains and Epitopes in the Rotavirus VP6 Protein," J Virol, Dec. 2000, 74(24):11574-11580, 7 pgs.
Choi, A.H-C., et al., "Functional mapping of protective epitopes within the rotavirus VP6 protein in mice belonging to different haplotypes," Vaccine, Jan. 2003, 21(7-8):761-767, 7 pgs.
Choi, J-M., et al., "Atomic resolution structural characterization of recognition of histo-blood group antigens by Norwalk virus," PNAS, 2008, 105(27):9175-9180, 6 pgs.
Chupakhin, O.N., et al., "An Unusally Easy Oxidative Dequarternization of N-alkyl-1,2,4-trizainium Salts," Mendeleev Communications, 1995, 3:104-105, CAPLUS Abstract, Doc No. 123:285918, 2 pgs.
Cooper, H.M., et al., "Production of Polyclonal Antisera," Curr Protoc Neurosci, 2009, Suppl 48:5.5.1-5.5.10, 10 pgs.
Crisc, E., et al., "Chimeric calicivirus-like particles elicit protective anti-viral Cytotoxic responses without adjuvant," Virol, May 2009, 387(2):303-312, 10 pgs.
Cuillel, M., et al., "A T = 1 Capsid Formed by Protein of Brome Mosaic Virus in the Presence of Trypsin," Virol, 1981, 110(1):63-72, 10 pgs.
Curnis, F., et al., "Differential Binding of Drugs Containing the NGR Motif to CD13 Isoforms in Tumor Vessels, Epithelia, and Myeloid Cells," Cancer Res, 2002, 62:867-874, 8 pgs.
De Filette, M., et al., "An Influenza A Vaccine Based on Tetrameric Ectodomain of Matrix Protein 2," J Biol Chem, 2008 , 283(17):11382-11387, 6 pgs.
De Rougemont, A., et al., "Qualitative and Quantitative Analysis of the Binding of GII.4 Norovirus Variants onto Human Blood Group Antigens," J Virol, 2011, 85(9):4057-4070, 14 pgs.
Desai, R., et al., "Potential Intussusception Risk Versus Benefits of Rotavirus Vaccination in the United States," The Pediatric Infectious Disease Journal, 2013, 32(1):1-7, 15 pgs.
Di, L. et al., "Solubility Issues in Early Discovery and HTS," Chapter 4 in *Solvent Systems and Their Selection in Pharmaceutics and Biopharmaceutics: Biotechnology Pharmaceutical Aspects*, 2007, VI:111-136, 26 pgs.
Dias da Silva, et al., "IgY: a promising antibody for use in immunodiagnostic and in immunotherapy", 2010, Vet Immunol Immunopathol, 135:173-180, 8 pgs.
Doud, M.B., et al., "Unexpected fold in the circumsporozoite protein target of malaria vaccines," PNAS, 2012, 109(20):7817-7822, 6 pgs.
Douglas, T., et al., "Viruses: Making Friends with Old Foes," Science, 2006, 312:873-875, 3 pgs.
Douglas, T., "A Bright Bio-Inspired Future," Science, 2003, 299:1192-1193, 2 pgs.
Dragnea, et al., "Gold Particles as Spectroscopic Enhancers for in Vitro Studies on Single Viruses," J Am Chem Soc, 2003, 125:6375-6375, 2 pgs.
Du, J., et al., "Detailed analysis of BALB/c mice challenged with wild type rotavirus EDIM provide an alternative for infection model of rotavirus," Virus Research, 2017, 228:134-140, 7 pgs.
Eldon Biologicals A/S, EldonCard Home Kit 2511 Manufacture Catalog, published on website, searched on Sep. 2008, in corresponding U.S. Appl. No. 11/264,992, 6 pgs.
Eldon Biologicals A/S, EldonCard Home Kit 2511 Manufacture Protocol, published on website, search on Sep. 2008, in corresponding U.S. Appl. No. 11/264,992, 1 pg.
Eldon Biologicals A/S, Evaluation Report, published 2004, in corresponding U.S. Appl. No. 11/264,992, 15 pgs.
EldonCard Home Blood Testing Kit, published on Website, search on Sep. 2008, in corresponding U.S. Appl. No. 11/264,992, 2 pgs.
Erdman, D.D., et al., "Serum Immunoglobulin A Response to Norwalk Virus Infection," Journal of Clinical Microbiology, Jun. 1989, 27(6):1417-1418, 2 pgs.
Erickson, J.W., et al., "The Structure of a *T* = 1 Icosahedral Empty Particle from Southern Bean Mosaic Virus," Science, 1985, 229(4714):625-629, 5 pgs.
Estes, M. et al., "Norwalk Virus Vaccines: Challenges and Progress," The Journal of Infectious Diseases, 2000, vol. 181(Suppl 2):S367-S373, 7 pgs.
Farkas, T., et al., "Homologous versus Heterologous Immune Responses to Norwalk-Like Viruses among Crew Members after Acute Gastroenteritis Outbreaks on 2 US Navy Vessles," The Journal of Infectious Diseases, 2003, 187:187-193, 7 pgs.
Farkas, T., et al., "Molecular Detection and Sequence Analysis of Human Caliciviruses From Acute Gastroenteritis Outbreaks in Hungary," Journal of Medical Virology, 2002, 67:567-573, 7 pgs.
Feng, X., et al., "Library Screen Inhibitors Targeting Norovirus Binding to Histo-Blood Group Antigen Receptors," Antimicrob Agents Chemother, 2007, 51(1):324-331, 8 pgs.
Feng, Z.K., et al., "Ligand Depot: a data warehouse for ligands bound to macromolecules," Bioinformatics, 2004, 20(13):2153-2155, 3 pgs.
Fischer Walker, C.L., et al., "Global burden of childhood pneumonia and diarrhoea," Lancet, 2013, 381:1405-1416, 12 pgs.
Glass, R.I., et al., "Norovirus Gastroenteritis," N Engl J Med, 2009, 361:1776-1785, 10 pgs.
Glass, R.I., et al., "Rotavirus Vaccines—Balancing Intussusception Risks and Health Benefits," N Engl J Med., 2014, 370(6):568-570, 4 pgs.
Glass, R.I., et al., "The changing epidemiology of astrovirus-associated gastroenteritis: a review," Archives of Virology, 1996, 12(Suppl):287-300, 14 pgs.
Gray, J.J. et al., "Prevalence of Antibodies to Norwalk Virus in England: Detection by Enzyme-Linked Immunosorbent Assay Using Baculovirus-Expressed Norwalk Virus Capsid Antigen," Journal of Clinical Microbiology, Apr. 1993, 31(4):1022-1025, 4 pgs.
Green, J., et al., "Capsid Protein Diversity among Norwalk-like Viruses," Virus Genes, May 2000, 20(3):227-236, 10 pgs.
Green, K.Y., et al., "Taxonomy of the Caliciviruses," The Journal of Infectious Diseases, 2000, 181(Suppl 2):S322-S330, 9 pgs.
Greenberg, H.B., et al., "Proteins of Norwalk Virus," J Virol, 1981, 37(3):997-999, 6 pgs.
Greenberg, H.B., et al., "Rescue of noncultivatable human rotavirus by gene reassortment during mixed infection with *ts* mutants of a cultivatable bovine rotavirus," PNAS, 1981, 78(1):420-424, 5 pgs.
Grgacic, E.V.L., et al., "Virus-like particles: Passport to immune recognition," Methods, 2006, 40(1):60-65, 6 pgs.
Groome, M.J., et al., "Safety and immunogenicity of a parenteral P2-VP8-P[8] subunit rotavirus vaccine in toddlers and infants in South Africa: a randomised, double-blind, placebo-controoled trial," Lancet Infect Dis, 2017, 17:843-853, 11 pgs.
Guix, S., et al., "Norwalk Virus RNA is Infectious in Mammalian Cells," J Virol, 2007, 81(22):12238-12248, 11 pgs.
Hale, A.D., et al., "Expression and Self-Assembly of Grimsby Virus: Antigenic Distinction from Norwalk and Mexico Viruses," Clinical and Diagnostic Laboratory Immunology, 1999, 6(1):142-145, 4 pgs.
Hale, A.D., et al., "Identification of an Epitope Commonc to Genogroup 1 "Norwalk-Like Viruses", " Journal of Clinical Microbiology, Apr. 2000, 38(4):1656-1660, 5 pgs.
Hansman, G.S., et al., "Crystal Structures of GII.10 and GII.12 Norovirus Protruding Domains in Complex with Histo-Blood Group Antigens Reveal Details for a Potential Site of Vulnerability," J Virol, 2011, 85(13):6687-6701, 15 pgs.
Hardy, M.E., et al., "Specific Proteolytic Cleavage of Recombinant Norwalk Virus Capsid Protein," J Virol, 1995, 69(3):1693-1698, 6 pgs.
Harrington, P. et al., "Binding of Norwalk Virus-Like Particles to ABH Histo-Blood Group Antigens is Blocked by Antisera from

(56) References Cited

OTHER PUBLICATIONS

Infected Human Volunteers or Experimentally Vaccinated Mice," Journal of Virology, Dec. 2002, 76(23):12335-12343, 9 pgs.
Harrington, P. et al., "Norovirus Capture with Histo-Blood Group Antigens Reveals Novel Virus-Ligand Interactions," Journal of Virology, Mar. 2004, 78(6):3035-3045, 11 pgs.
Harrison, S.C., "Principles of Virus Structure," Chapter 3, In D.M. Knipe, et al., (eds.), Fields Virology, 4th Ed., vol. 1, Lippincott Williams & Wilkins, 2001, pp. 53-85, 33 pgs.
Hennessy, E.P., et al., "Norwalk Virus Infection and Disease is Associated with ABO Histo-Blood Group Type," The Journal of Infectious Diseases, 2003, 188:176-177, 2 pgs.
Hetenyi, C., et al., "Efficient docking of peptides to proteins without prior knowledge of the binding site," Protein Science, 2002, 11:1729-1737, 9 pgs.
Hoffman, R., (ed), *Hematology Basic Principles and Practice*, 2nd Ed., Churchill Linvingstone, NY, NY, 1995, 8 pgs. (Table of Contents only).
Hu, L., et al., "Cell attachment protein VP8* of a human rotavirus specifically interacts with A-type histo-blood group antigen," Nature, 2012, 485:256-259, 5 pgs.
Hu, L., et al., "Structural basis of glycan specificty in neonate-specific bovine-human reassortant rotavirus," Nat Commun, 2015, 6:8346, 10 pgs.
Huang, P.W., et al., "Concentration and Detection of Caliciviruses in Water Samples by Reverse Transcription-PCR," Appl Environ Microbiol, 2000, 66(10):4383-4388, 6 pgs.
Huang, P. et al., "Noroviruses Bind to Human ABO, Lewis, and Secretor Histo-Blood Antigens: Identification of 4 Distinct Strain-Specific Patterns," J Infect Dis, Jul. 2003, 188:19-31, 13 pgs.
Huang, P., et al., "Norovirus and Histo-Blood Group Antigens: Demonstration of a Wide Spectrum of Strain Specificities and Classification of Two Major Binding Groups Among Multiple Binding Patterns," J Virol, 2005, 79(11):6714-6722, 9 pgs.
Huang, P., et al., "Spike Protein VP8* of Human Rotavirus Recognizes Histo-Blood Group Antigens in a Type-Specific Manner," J Virol, 2012, 86:4833-4843, 11 pgs.
Hutson, A.M. et al., "ABO Phenotype Association with Norwalk Virus Infection and Disease may be Related to Norwalk Virus-Like Particle Binding H Antigens," Gastroenterology, Apr. 2002, 122(4 Suppl 1):A141-A142, Abstract S994, 2 pgs.
Hutson, A.M., et al., "Loss of carbohydrate binding with point mutations of Norwalk virus-like particles," Second International Calicivirus Conference, Dijion, France, Nov. 6-10, 2004. (Reference unavailable. Please consider as prior art until proven otherwise.) 1 pg.
Hutson, A.M., et al., "Norovirus disease: changing epidemiology and host susceptibility factors," Trends Microbiol, 2004, 12(6):279-287, 9 pgs.
Hutson, A.M., et al., "Norwalk Virus Infection and Disease is Associated with ABO Histo-Blood Group Type," The Journal of Infectious Diseases, 2002, 185:1335-1337, 3 pgs.
Hutson, A.M. et al., "Norwalk Virus-Like Particle Hemmagglutination by Binding to H Histo-Blood Group Antigens," J Virol, 2003, 77(1):405-415, 11 pgs.
Immuncor Inc., Manufacture Advertisement, published on Immucor Website, searched Sep. 2008, in corresponding U.S. Appl. No. 11/264,992, 1 pgs.
Irwin, J.J. et al., "ZINC—A Free Database of Commerically Available Compounds for Virtual Screening," J Chem Inf Model, 2005, 45(1):177-182, 11 pgs.
Irwin, J.J. et al., "ZINC: A Free Tool to Discover Chemistry for Biology," J Chem Inf Model, 2012, 52(7):1757-1768, 12 pgs.
Jennings, G.T., et al., "The coming of age of virus-like particle vaccines," Biological Chemistry, 2008, 389(5):521-536, 16 pgs.
Jiang, X., et al., "Baculovirus expression and antigentic characterization of the capsid proteins of three Norwalk-like viruses," Arch Virol, 2002, 147:119-130, 12 pgs.
Jiang, X., et al., "*Capsid*," Nucleotide sequence, UniProtKB/Swiss Prot:Q913Z3 (Q913Z3_9CALI), created Dec. 1, 2001, updated Oct. 31, 2006, 1 pg.
Jiang, X., et al., "Expression, Self-Assembly, and Antigenicity of the Norwalk Virus Capsid Protein," J Virol, 1992, 66(11):6527-6532, 6 pgs.
Jiang, X., et al., "Expression, Self-Assembly, and Antigenicity of a Snow Mountain Agent-Like Calicivirus Capsid Protein," J Clin Microbio, 1995, 33(6):1452-1455, 4 pgs.
Jiang, X., et al., "Histo-blood group antigens as receptors for rotavirus, new understanding on rotavirus epidemiology and vaccine strategy," Emerging Microbes & Infections, 2017, 6:e22, 8 pgs.
Jiang, X., et al., "Human Milk Contains Elements That Block Binding of Noroviruses to Human Histo-Blood Group Antigens in Saliva," J Infect Diseases, Nov. 2004, 190:1850-1859, 10 pgs.
Jiang, X., et al., "Norwalk Virus Genome Cloning and Characterization," Science, Dec. 1990, 250:1580-1583, 4 pgs.
Jiang, X., et al., "Sequence and Genomic Organization of Norwalk Virus," Virology, 1993, 195:51-61, 11 pgs.
KIT, definition of, http://acronyms.thefreedictionary.com/kit, in corresponding U.S. Appl. No. 11/264,992, printed on Feb. 22, 2008, 4 pgs.
Kubota, T., et al., "Structural Basis for the Recognition of Lewis Antigens by Genogroup I Norovirus," J Virol, 2012, 86(20):11138-11150, 13 pgs.
Kumar, S., et al., "MEGA2: molecular evolutionary genetics analysis software," Bioinformatics Applications Note, 2001, 17(12):1244-1245, 2 pgs.
Kurdyashov, V., et al., "Characterization of a mouse monoclonal IgG3 antibody to the tumor-associated globo H structure produced by immunization with a synthetic glycoconjugate" Glycoconjugate Journal, 1998, 15:243-249, 7 pgs.
Lancel, M., et al., "Allopregnanolone Affects Sleep in a Benzodiazepine-Like Fashion," The Journal of Pharmacology and Experimental Therapeutics, 1997, 282(3):1213-1218, 6 pgs.
Lavanchy, D., "Worldwide epidemiology of HBV infection, disease burden, and vaccine prevention," J Clin Virol, 2005, 34(suppl 1):S1-S3, 3 pgs.
Lew, J.F., et al., "Molecular Characterization of Hawaii Virus and Other Norwalk-like Viruses: Evidence for Genetic Polymorphism among Human Caliciviruses," J Infect Dis, 1994, 170:535-542, 8 pgs.
Lindesmith, L., et al., "Cellular and Humoral Immunity following Snow Mountain Virus Challenge," J Virol, 2005, 79(5):2900-2909, 10 pgs.
Lindesmith, L., et al., "Human Susceptibility and Resistance to Norwalk Virus Infection," Nature Medicine, May 2003, 9(5):548-553, 6 pgs.
Liou, J-F., et al. "Passive protection effect of chicken egg yolk immunoglobulins on enterovirus 71 infected mice," Vaccine, 2010, 28:8189-8196, 8 pgs.
Liu, B., et al., "The Genomic 5' Terminus of Manchester Calicivirus," Virus Genes, 1997, 15(1):25-28, 4 pgs.
Liu, W., et al., "A Unique Human Norovirus Lineage with a Distinct HBGA Binding Interface," PLoS Pathog, 2015, 11(7):e1005025, 22 pgs.
Liu, Y., et al., "Glycan Specificity of P[19] Rotavirus and Comparison with Those of Related P Genotypes," J Virol, 2016, 90(21):9983-9996, 14 pgs.
Liu, Y., et al., "Rotavirus VP8*:Phylogeny, Host Range, and Interaction with Histo-Blood Group Antigens," J Virol, 2012, 86(18):9899-9910, 12 pgs.
Lokesh, G.L., et al., "A Molecular Switch in the Capsid Protein Controls the Particle Polymorphism in an Isosahedral Virus," Virol, 2002, 292:211-223, 13 pgs.
Lopman, B., et al., "Environmental transmission of norovirus gastroenteritis," Curr Opin Virol, 2012, 2:96-102, 7 pgs.
Madhi, S.A., et al., "Effect of Human Rotavirus Vaccine on Severe Diarrhea in African Infants," N Engl J Med, 2010, 362(4):289-298, 10 pgs.
Manayani, D.J., "A Viral Nanoparticle with Dual Function as an Anthrax Antitoxin and Vaccine," PLoS Pathog, 2007, 3(10):1422-1431, 10 pgs.

(56) References Cited

OTHER PUBLICATIONS

Marionneau, S., et al., "ABH and Lewis Histo-Blood Group Antigens, A Model for the Meaning of Oligosaccharide Diversity in the Face of a Changing World," Biochimie, 2001, 83(7):565-573, 9 pgs.
Marionneau, S., et al., "Norwalk Virus Binds to Histo-Blood Group Antigens Present on Gastroduodenal Epithelial Cells of Secretor Individuals," Gastroenterology, Jun. 2002, 122:1967-1977, 11 pgs.
McNeal, M.M., et al., "Antibody-Dependent and -Independent Protection following Intranasal Immunization of Mice with Rotavirus Particles," J Virol, 1999, 73(9):7565-7573, 9 pgs.
Minnesota Department of Health, "Norovirus Fact Sheet," Jun. 2009, 2 pgs.
Molport HTS Library Product Page for compounds 002-511-430 and 002-513-186 (Published online 2011). CAS Registry of compounds 002-511-430 and 002-516-186 indexed on Oct. 14, 1997 and Jul. 11, 2008, 7 pgs.
Morris, G.M., et al., "Automated Docking Using a Lamarckian Genetic Algorithm and an Emperical Binding Free Engery Function," Journal of Computational Chemistry, 1998, 19(4):1639-1662, 24 pgs.
National Cancer Institute, Downloadable Structure Files of NCI Open Database Compounds, Release 4 File Series, May 2012, 4 pgs.
Nguyen, H.H., et al., "Prophylactic and Therapeutic Efficacy of Avian Antibodies Againt Influenza Virus H5N1 and H1N1 in Mice," PLoS One, 2010, 5:e10152, 11 pgs.
Nicholas, K.B., et al., "GeneDoc: Analysis and Visualization of Genetic Variation," EMBENT.news, Jul. 1997, 4(2):1-4, 4 pgs.
Nurminek, K., et al., "Prevalence of Norovirus GII-4 Antibodies in Finnish Children," J Med Virol, 2011, 83:525-531, 7 pgs.
Ochoa, W.F., et al., "Generation and Structural Analysis of Reactive Empty Particles Derived from an Icosahedral Virus," Chem Biol, 2006, 13:771-778, 8 pgs.
Oriol, R., et al., "Insights into the Expression of ABH and Lewis Antigens through Human Bone Marrow Transplantation," Am J Hum Genet, 1981, 33:551-560, 10 pgs.
Parashar, U.D., et al., "Rotavirus and Severe Childhood Diarrhea," Emerg Infect Dis, 2006, 12(2):304-306, 3 pgs.
Pasqualini, R., et al., "Aminopeptidase N is a Receptor for Tumorhoming Peptides and a Target for Inhibiting Angiogenesis," Cancer Research, 2000, 60:722-727, 6 pgs.
Patel, M.M., et al., "Noroviruses: A comprehensive review," J Chem Virol, 2009, 44:1-8, 8 pgs.
Patel, M.M., et al., "Systematic Literature Review of Role of Noroviruses in Sporadic Gastroenteritis," Emerg Infect Dis, 2008, 14(8):1224-1231, 9 pgs.
Peabody, D.S., "A Viral Platform for Chemical Modification and Multivalent Display", J Nanobiotechnology, 2003, 1:5, 8 pgs.
Pelosi, E., et al., "The Seroepidemiology of Genogroup 1 and Genogroup 2 Norwalk-Like Viruses in Italy," Journal of Medical Virology, Apr. 1999, 58(1):93-99, 7 pgs.
Prevent, definition of, Merriam-Webster's Collegiant Dictionary, 10th Ed., Merriam-Webster, Inc., 1998, p. 924, 3 pgs.
Radloff, C., et al., "Metal Nanoshell Assembly on a Virus Bioscaffold," Nano Lett, 2005, 5(6):1187-1191, 5 pgs.
Ravan, V., et al., "Tissue distribution of histo-blood group antigens," APMIS, 2000, 108:1-28, 28 pgs.
Reeck, A., et al., "Serological Correlate of Protection against Norovirus-Induced Gastroenteritis," J Infect Dis, 2010, 202:1212-1218, 7 pgs.
Rosillon, D., et al., "Risk of Intussusception After Rotavirus Vaccination: Meta-analysis of Postlicensure Studies," Pediatr Infect Dis J, 2015, 34:763-768, 6 pgs.
Savithri, H.S., et al., "The Self-Assembly of the Cowpea Strain of Southern Bean Mosaic Virus: Formation of $T$ = 1 and $T$ = 3 Nucleoprotein Particles," Virol, 1983, 126(1):328-335, 8 pgs.
Schwartz, S., et al., "Norovirus gastroenteritis causes severe and lethal complications after chemotherapy and hematopoietic stem cell transplantation," Blood, 2011, 117(22):5850-5856, 7 pgs.
Settembre, E.C., et al., "Atomic model of an infectious rotavirus particle," EMBO J, 2011, 30:408-416, 9 pgs.
Shanker, S., et al., "Structural Analysis of Determinants of Histo-Blood Group Antigen Binding Specificity in Genogroup I Noroviruses," J Virol, 2014, 88(11):6168-6180, 13 pgs.
Shanker, S., et al., "Structural Analysis of Histo-Blood Group Antigen Binding Specificity in a Norovirus GII.4 Epidemic Variant: Implications for Epochal Evolution," J Virol, 2011, 85(17):8635-8645, 11 pgs.
Shoemaker, G.K., et al., "Norwalk Virus Assembly and Stability Monitored by Mass Spectrometry," Molecular & Cellular Proteomics, 2010, 9:1742-1751, 10 pgs.
Silverman, R.B., "Drug Discovery, Design, and Development," Chapter 2 in *The Organic Chemistry of Drug Design and Drug Action*, Academic Press, Inc., San Diego, CA, 1992, pp. 4-47, 56 pgs.
Sixth International Symposium on Positive Strand RNA Viruses (May 28-Jun. 2, 2001), Institut Pasteur, Paris, France; Scientific Program Abstracts "Norwalk Virus Binds to H Type 1 Histo-Blood Group Antigen Present on Gastro-Duodenal Epithelial Cells of "Secretor" Pheotype Individuals" 2001, p. 4, 10 pgs. (Mention only) (See also, Marionneau, S., Gastroenterology, Jun. 2002, 122:1967-1977, 11 pgs.).
Sorger, P.K., et al., "Structure and Assembly of Turnip Crinkle Virus, II. Mechanism of Reassembly in Vitro," J Mol Biol, 1986, 191:639-658, 20 pgs.
Tamura, M. et al., "Interaction of Recombinant Norwalk Virus Particles with the 105-Kilodalton Cellualr Binding Protein, a Candidate Molecule for Virus Attachment," J Virol, 2000, 74(24):11589-11597, 9 pgs.
Tan, M., et al., "Conservation of Carbohydrate Binding Interfaces—Evidence of Human HBGA Selection in Norovirus Evolution," PLoS ONE, 2009, 4(4):e5058, 14 pgs.
Tan, M., et al., "C-Terminal Arginine Cluster is Essential for Receptor Binding of Norovirus Capsid Protein," J Virol, 2006, 80(15):7322-7331, 10 pgs.
Tan, et al., "*E. coli*-Expressed Recombinant Norovirus Capsid Proteins Maintain Authentic Antigenicity and Receptor Binding Capability," J Med Virol, 2004, 74(4):641-649, 9 pgs.
Tan, M., et al., "Elucidation of strain-specific interaction of a GII-4 norovirus with HBGA receptors by site-directed mutagenesis study," Virol, 2008, 379(2):324-334, 11 pgs.
Tan, M., et al., "Histo-blood group antigens: a common niche for norovirus and rotavirus," Expert Rev Mol Med, 2014, 16:e5, 20 pgs.
Tan, M., et al., "Mutations within the P2 Domain of Norovirus Capsid Affect Binding to Human Histo-Blood Group Antigens: Evidence for a Binding Pocket," J Virol, 2003, 77(23):12562-12571, 10 pgs.
Tan, M., et al., "Noroviral P particle: Structure, function and applications in virus-host interaction," Virology, 2008, 382(1):115-123, 9 pgs.
Tan, M., et al., "Norovirus and its histo-blood group antigen receptors: an answer to a historical puzzle," Trends Microbiol, 2005, 13(6):285-293, 9 pgs.
Tan, M., et al., "Norovirus Gastroenteritis, Carbohydrate Receptors, and Animal Models," PLoS Pathog, 2010, 6(8):e1000983, 5 pgs.
Tan, M., et al., "Norovirus-host interaction: implications for disease control and prevention," Expert Rev Mol Med, 2007, 9(19):1-22, 22 pgs.
Tan, M., et al., "Norovirus-host interaction: multi-selections by human HBGAs," Trends Microbiol, 2011, 19(8):382-388, 13 pgs.
Tan, M., et al., "Norovirus P Particle, a Novel Platform for Vaccine Development and Antibody Production," J Virol, 2011, 85(2):753-764, 12 pgs.
Tan, M., et al., "Norovirus P particle: a subviral nanoparticle for vaccine development agaisnt norovirus, rotavirus and influenza virus," Nanomedicine, 2012, 7(6):889-897, 14 pgs.
Tan, M., et al., "Recent advancements in combination subunit vaccine development," Human Vaccines & Immunotherapeutics, 2017, 13(1):180-185, 6 pgs.
Tan, M., et al., "Subviral Particle as Vaccine and Vaccine Platform," Curr Opin Virol., 2014, 0:24-33, 18 pgs.
Tan, M., et al., "Terminal modification of norovirus P domain resulted in a new type of subviral particles, the small P particles," Virology, 2011, 410:345-352, 8 pgs.

(56) References Cited

OTHER PUBLICATIONS

Tan et al., "The formation of P particle increased immunogenicity of norovirus P protein," Immunology, 2012, 136:28-29, 2 pgs.
Tan, M., et al., "The P Domain of Norovirus Capsid Protein Forms a Subviral Particle That Binds to Histo-Blood Group Antigen Receptors," J Virol, 2005, 79(22):14017-14030, 14 pgs.
Tan, M., et al., "The P Domain of Norovirus Capsid Protein Forms Dimer and Binds to Histo-Blood Group Antigen Receptors," J Virol, 2004, 78(12):6233-6242, 10 pgs.
Tate, J.E., et al., "2008 estimate of worldwide rota-virus-associated mortality in children younger than 5 years before the introduction of universal rotavirus vaccination programmes: a systemic review and meta-analysis," Lancet Infect Dis, 2012, 12:136-141, 6 pgs.
Taube, S., et al., "Murine Noroviruses Bind Glycolipid and Glycoprotein Attachment Receptors in a Strain-Dependent Manner," J Virol, 2012, 86(10):5584-5593, 10 pgs.
Tini, M., et al., "Generation and application of chicken egg-yolk antibodies," Comparative Biochemistry and Physiology Part A, 2002, 131:569-574, 6 pgs.
Treanor, J. J. et al., "Development of an enzyme immunoassay for the Hawaii agent of viral gastroenteritis," Journal of Virol Methods, Dec. 1998, 22(2-3):207-214, 8 pgs.
Troy, D.B. (ed.), et al., Remington, The Science and Practice of Pharmacy, 21st Ed., Lippincott Williams & Wilkins, Philadelphia, PA, 2006, p. 89, 7 pgs.
Vega, C., et al., "Egg yolk IgY: Protection against rotavirus induced diarehea and modulatory effect on the systemic and mucosal antibody responses in newborn calves," Vet Immunopathol, 2011, 142:156-169, 14 pgs.
Vankataram Prasad, B.V., et al., "-Ray Crystallographic Structure of the Norwalk Virus Capsid," Science, Oct. 1999, 286:287-290, 4 pgs.
Vesikari, T., et al., "Efficacy of a pentavalent rotavirus vaccine in reducing rotavirus-associated health care utilization across three regions (11 countries)," Int J Infect Dis, 2007, 11(Suppl 2):S29-S35, 7 pgs.
Villoutreix, B.O., et al., "Structure-Based Virtual Ligand Screening: Recent Success Stories," Cominatorial Chemistry & High Throughput Screening, 2009, 12:1000-1016, 17 pgs.
Wang, L., et al., "A Dial Vaccine Candidate against Norovirus and Hepatitis E Virus," Vaccine, 2014, 32(4):445-452, 16 pgs.
Wang, L., et al., "Branched-linear and agglomerate protein polymers as vaccine platforms," Biomaterials, 2014, 35:8424-8438, 12 pgs.
Wang, L.Y., et al., *Outer capsid protein VP4* [Human rotavirus A], Protein sequence, UniProtKB—H6WUJ8 (H6WUJ8_9REOV), Submitted Apr. 18, 2012, 5 pgs.
Wang, L., et al., "Polyvalent complexes for vaccine development," Biomaterials, 2013, 34(18):4480-4492, 13 pgs.
Wang, L.Y., et al., *VP4, partial* [Human rotavirus A], RNA sequence, GenBank: AFA25718.1, Submitted Dec. 21, 2011, 1 pg.
Weintraub, E.S. et al., "Risk of Intussusception after Movovalent Rotavirus Vaccination," N Engl J Med, 2014, 370:513-519, 7 pgs.
Wen, X., et al., "Tandem truncated rotavirus VP8* subunit protein with T cell epitope as non-replicating parenteral vaccine is highly immunogenic," Human Vaccines & Immunotherapeutics, 2015, 11(10):2483-2489, 7 pgs.
White, L.J., et al., "Attachement and Entry of Recombinant Norwalk Virus Capsids to Cultured human and Animal Cell Lines," J Virol, Oct. 1996, 70(10):6589-6597, 9 pgs.
White, L.J., et al., "Biochemical Characterization of a Smaller Form of Recombinant Norwalk Virus Capsids Assembled in Insect Cells." J Virol, Oct. 1997, 71(10):8066-8072, 7 pgs.
Wobus, C.E., et al., "Replication of *Norovirus* in Cell Culture Reveals a Tropism for Dendritic Cells and Macrophages," PLoS Biol, 2004, 2(12):e432, 9 pgs.
Wolf, A., et al., "*In Silico* Drug Discovery Approaches on Grib Computing Infrastructures," Current Clinical Pharmacology, 2010, 5:37-46, 10 pgs.
Xia, M., et al., "A candidate dual vaccine against influenza and noroviruses," Vaccine, 2011, 29(44):7670-7677, 16 pgs.
Xia, M., et al., "A trivalent vaccine candidate againt hepatitis E virus, norovirus, and astrovirus," Vaccine, 2016, 37(7):905-913, 24 pgs.
Xia, M., et al., "Development and evaluation of two subunit vaccine candidates containing antigens of hepatits E virus, rotavirus, and astrovirus," Sci Rep, 2016, 6:25735, 12 pgs.
Xia, M., et al., "Norovirus Capsid Protein Expressed in Yeast Forms Virus-like Particles and Stimulates Systemic and Mucosal Immunity in Mice Following an Oral Administration of Raw Yeast Extracts," J Med Virol, 2007, 79(1):74-83, 10 pgs.
Xu, Y., et al., "Application of chicken egg yolk immunoglobulins in the control of terrestrial and aquatic animal diseases: A review," Biotechol Adv, 2011, 29:860-868, 9 pgs.
Yang, Y., et al., *capsid protein*, [Norovirus Hu/GII.4/082686/Alberta/2000/CA], Protein sequence, GenBank: ADF50093.1, submitted Apr. 25, 2010, 1 pg
Yen, C., et al., "Rotavirus vaccines: Update on global impact and future priorities," Human Vaccines, 2011, 7(12):1282-1290, 9 pgs.
Yih, W.K., et al., "Intussusception Risk after Rotavirus Vaccination in U.S. Infants," N Engl J Med, 2014, 370(6):503-512, 10 pgs.
Yung, C-F., et al., "Intussusception and Monovalent Rotavirus Vaccination in Singapore: Self-Controlled Case Series and Risk-Benefit Study," J Pediatr, 2015, 167:163-168 & 168.e1, 7 pgs.
Zaman, K., et al., "Efficacy of pentavalent rotavirus vaccine against severe rotavirus gastroenteritis in infants in developing countries in Asia: a randomised, double-blind, placebo-controlled trial," Lancet, 2010, 376:615-623, 9 pgs.
Zhang, X-F., et al., "Tannic acid inhibited norovirus binding to HBGA receptors, a study of 50 Chinese medicinal herbs," Bioorg Med Chem, 2012, 20:1616-1623, 8 pgs.
Zheng, D-P., et al., "Molecular Epidemiology of Genogroup II-Genotype 4 Noroviruses in the United States between 1994 and 2006," J Clin Microbiol, 2010, 48(1):168-177, 10 pgs.
Australian Information Statement Documentary Search Results dated May 16, 2007 for Application No. AU 2003273206, 1 pg.
Canadian Office Action dated Jan. 26, 2010 for Application No. CA 2,487,846, 4 pgs.
Canadian Response and Amendment filed Jul. 16, 2010 for Application No. CA 2,487,846, 6 pgs.
Canadian Response and Amendment filed Mar. 3, 2011 for Application No. CA 2,487,846, 4 pgs.
Chinese Office Action, The First Office Action, and First Search Report dated Jul. 11, 2013 for Application No. CN 201080035302.2, 8 pgs.
Chinese Office Action, The Second Office Action dated Apr. 28, 2014 for Application No. CN 201080035302.2, 11 pgs.
Chinese Office Action, The First Office Action, and First Search Report dated Feb. 3, 2020 for Application No. CN 201710198133.8, 10 pgs.
Chinese Office Action, The Second Office Action, dated Jun. 29, 2020, for Application No. CN 201710198133.8, 10 pgs.
European Search Report, Supplementary, and Written Opinion dated Jan. 7, 2013 for Application No. EP 10786797.0, 4 pgs.
European Search Report, Supplemantary Partial, dated Sep. 28, 2005 for Application No. EP 03741844.9, 3 pgs.
International Search Report dated Jan. 14, 2005 for Application No. PCT/US2003/017247, 4 pgs.
International Preliminary Examination Report dated Mar. 21, 2005 for Application No. PCT/US2003/017247, 3 pgs.
International Search Report dated Apr. 23. 2007 for Application No. PCT/US2006/023407, 2 pgs.
International Preliminary Report on Patentability and Written Opinion dated Dec. 17, 2007 for Application No. PCT/US2006/023407, 6 pgs.
International Search Report dated Mar. 31, 2011 for Application No. PCT/US2010/038008, 5 pgs.
International Preliminary Report on Patentability and Written Opinion dated Dec. 12, 2011 for Application No. PCT/US2010/038008, 5 pgs.
International Search Report and Written Opinion dated Oct. 16, 2013 for Application No. PCT/US2013/050004, 17 pgs.
International Search Report and Written Opinion dated Dec. 23, 2013 for Application No. PCT/US2013/050044, 8 pgs.

(56) References Cited

OTHER PUBLICATIONS

International Search Report and Written Opinion, Corrected, dated Jul. 16, 2018 for Application No. PCT/US2018/022552, 14 pgs.
Japanese Office Action dated Oct. 21, 2014 for Application No. JP 2012-515109, 3 pgs.
Japanese Office Action dated Jun. 9, 2015 for Application No. JP 2012-515109, 2 pgs.
Xia, M., et al., "Bioengineered Norovirus $S_{60}$ Nanoparticles as a Multifunctional Vaccine Platform," ACS Nano, 2018, 12(1):10665-10682, 36 pgs.
Japanese Office Action, Notice of Reasons for Refusal, dated Feb. 22, 2022 for Application No. JP 2019-546799, 6 pgs.
Bale, J.B., et al., "Accurate design of megadalton-scale two-component icosahedral protein complexes," Science, 2016, 353(6297):389-394, 7 pgs.
Boyoglu-Barnum, S., et al., "Elicitation of broadly protective immunity to influenza by multivalent hemagglutinin nanoparticle vaccines," bioRxiv, 2020.05.30.125179, 2020. Available at: https://doi.org/10.1101/2020.05.30.125179, 29 pgs.
Centers for Disease Control and Prevention. Seasonal influenza vaccine effectiveness, 2005-2020 [Online]. https://www.cdc.gov/flu/vaccines-work/effectiveness-studies.htm (accessed 2020), 4 pgs.
D'Aoust, M.A., et al., "The production of hemagglutinin based virus-like particles in plants: A rapid, efficient and safe response to pandemic influenza," Plant Biotechnol J, 2010, 8:607-619, 13 pgs.
Deng, L., et al., "M2e-Based Universal Influenza A Vaccines," Vaccines, 2015, 3(1):105-36, 32 pgs.
Devant, J.M., et al., "Structural heterogeneity of a human norovirus vaccine candidate," Virology, 2021, 553:23-34, 12 pgs.
Ebrahimi, S.M., et al., "Influenza A viruses: why focusing on M2e-based universal vaccines," Virus Genes, 2011, 42(1):1-8, 8 pgs.
Ekiert, D.C., et al., "Cross-neutralization of influenza A viruses mediated by a single antibody loop," Nature, 2012, 489:526-532, 10 pgs.
Fischer, II, W.A., et al., "Global Burden of Influenza as a Cause of Cardiopulmonary Morbidity and Mortality," Glob Heart, 2014, 9(3):325-336, 12 pgs.
Gouma, S., et al., "Comparison of Human H3N2 Antibody Responses Elicited by Egg-Based, Cell-Based, and Recombinant Protein-Based Influenza Vaccines During the 2017-2018 Season," Clin Infect Dis, 2020, 71:1447-1453, 7 pgs.
Iuliano, A.D., et al., "Estimates of global seasonal influenza-associated respiratory mortality: A modelling study," Lancet, 2018, 391(10127):1285-1300, 31 pgs.
Jung, J., et al., "High-resolution cryo-EM structures of outbreak strain human norovirus shells reveal size variations," Proc Natl Acad Sci USA, 2019, 116(26):12828-12832, 5 pgs.
Kanekiyo, M., et al., "Mosaic nanoparticle display of diverse influenza virus hemagglutinins elicits broad B cell responses," Nat Immunol, 2019, 20(3):362-372, 31 pgs.
Kanekiyo, M., et al., "Self-Assembling Influenza Nanoparticle Vaccines Elicit Broadly Neutralizing H1N1 Antibodies," Nature, 2013, 499(7456):102-106, 16 pgs.
Khurana, S., et al., "Bacterial HA1 Vaccine against Pandemic H5N1 Influenza Virus: Evidence of Oligomerization, Hemagglutination, and Cross-Protective Immunity in Ferrets," J Virol, 2011, 85(3):1246-1256, 11 pgs.
Klimochkin, Y.N., et al., "Design of Broad-Spectrum Inhibitors of Influenza A Virus M2 Proton Channels: A Molecular Modeling Approach," Curr Comput Aided Drug Des, 2016, 12(2):154-164, 11 pgs.
Lee, P.S., et al., "Receptor mimicry by antibody F045-092 facilitates universal binding to the H3 subtype of influenza virus," Nat Commun, 2014, 5:3614, 22 pgs.
Levine, M.Z., et al., "Antibodies Against Egg- and Cell-Grown Influenza A(H3N2) Viruses in Adults Hospitalized During the 2017-2018 Influenza Season," J Infect Dis, 2019, 219:1904-1912, 9 pgs.
Mezhenskaya, D., et al., "M2e-based universal influenza vaccines: a historical overview and new approaches to development," J Biomed Sci, 2019, 26(1):76, 15 pgs.
Paules, C.I., et al., "Chasing Seasonal Influenza—The Need for a Universal Influenza Vaccine," New Engl J Med, 2018, 378(1):7-9, 3 pgs.
Pielak, R.M., et al., "Influenza M2 proton channels," Biochim Biophys Acta, 2011, 1808(2):522-529, 16 pgs.
Portnoff, A.D., et al., "Influenza Hemagglutinin Nanoparticle Vaccine Elicits Broadly Neutralizing Antibodies Against Structurally Distinct Domains of H3N2 HA," Vaccines, 2020, 8:99, 17 pgs.
Punjani, A., et al., "cryoSPARC: Algorithms for rapid unsupervised cryo-EM structure determination," Nat Methods, 2017, 14(3):290-296, 8 pgs.
Rolfes, M.A., et al., "Effects of Influenza Vaccination in the United States During the 2017-2018 Influenza Season," Clin Infect Dis, 2019, 69:1845-1853, 9 pgs.
Saelens, X., "The Role of Matrix Protein 2 Ectodomain in the Development of Universal Influenza Vaccines," J Infect Dis, 2019, 219(Suppl 1):S68-S74, 7 pgs.
Scheres, S.H.W., "A Bayesian View on Cryo-EM Structure Determination," J Mol Biol, 2012, 415(2):406-418, 13 pgs.
Shi, Y., et al., "Structures and Receptor Binding of Hemagglutinins from Human-Infecting H7N9 Influenza Viruses," Science, 2013, 342:243-247, 5 pgs.
Skowronski, D.M., et al., "Low 2012-13 Influenza Vaccine Effectiveness Associated with Mutation in the Egg-Adapted H3N2 Vaccine Strain not Antigenic Drift in Circulating Viruses," PLoS One, 2014, 9(3):e92153, 15 pgs.
Smith, G., et al., "Novel hemagglutinin nanoparticle influenza vaccine with Matrix-M™ adjuvant induces hemagglutination inhibition, neutralizing, and protective responses in ferrets against homologous and drifted A(H3N2) subtypes," Vaccine, 2017, 35:5366-5372, 7 pgs.
Su, S., et al., "Epidemiology, Evolution, and Pathogenesis of H7N9 Influenza Viruses in Five Epidemic Waves since 2013 in China," Trends Microbiol, 2017, 25(9):713-728, 16 pgs.
Tan, M., et al., "Nanoparticles of norovirus," in Viral Nanotechnology, Y. Khudyakov, and p. Pumpens, (eds.), CRC Press: Boca Raton, 2015; pp. 363-371, Abstract only, 1 pg.
Tan, M., et al., "Norovirus Capsid Protein-Derived Nanoparticles and Polymers as Versatile Platforms for Antigen Presentation and Vaccine Development," Pharmaceutics, 2019, 11:472, 16 pgs.
Tan, M., et al., "Saliva as a source of reagent to study human susceptibility to avian influenza H7N9 virus infection," Emerg Microbes Infect, 2018, 7:156, 10 pgs.
Tharakaraman, K., et al., "Glycan-Receptor Binding of the Influenza A Virus H7N9 Hemagglutinin," Cell, 2013, 153(7):1486-1493, 14 pgs.
Thompson, C.P., et al., "A naturally protective epitope of limited variability as an influenza vaccine target," Nat Commun, 2018, 9:3859, 10 pgs.
Whittle, J.R.R., et al., "Broadly neutralizing human antibody that recognizes the receptor-binding pocket of influenza virus hemagglutinin," Proc Natl Acad Sci USA, 2011, 108(34):14216-14221, 6 pgs.
World Health Organization (WHO), "8 Things to know about pandemic influenza," [Online]. www.who.int/news-room/feature-stories/detail/8-things-to-know-about-pandemic-influenza, 2019, 3 pgs.
Wu, N.C., et al., "A structural explanation for the low effectiveness of the seasonal influenza H3N2 vaccine," PLoS Pathog, 2017, 13(10):e1006682, 17 pgs.
Xia, M. et al., "Immune Response and Protective Efficacy of the S Particle Presented Rotavirus VP8* Vaccine in Mice," Vaccine, 2019, 37(30):4103-4110, 18 pgs.
Xia, M., et al., "A Nanoparticle-Based Trivalent Vaccine Targeting the Glycan Binding VP8* Domains of Rotaviruses," Viruses, 2021, 13:72, 15 pgs.
Xia, M., et al., "Bioengineered pseudovirus nanoparticles displaying the HA1 antigens of influenza viruses for enhanced immunogenicity," Nano Research, 2022, 15(5):4181-4190, 10 pgs.

(56) References Cited

OTHER PUBLICATIONS

Xu, R., et al., "Preferential recognition of avian-like receptors in human influenza A H7N9 viruses" Science, 2013, 342(6163):1230-1235, 12 pgs.
Yang, H., et al., "Structural Analysis of the Hemagglutinin from the Recent 2013 H7N9 Influenza Virus," J Virol, 2013, 87(22):12433-12446, 14 pgs.
Yassine, H.M., et al., "Hemagglutinin-stem nanoparticles generate heterosubtypic influenza protection," Nat Med, 2015, 21(9):1065-1070, 9 pgs.
Zhang, K., "GCTF: Real-time CTF determination and correction," J Struct Biol, 2016, 193(1):1-12, 12 pgs.
Zost, S.J., et al., "Contemporary H3N2 influenza viruses have a glycosylation site that alters binding of antibodies elicited by egg-adapted vaccine strains," Proc Natl Acad Sci USA, 2017, 114(47):12578-12583, 6 pgs.
Chinese Office Action, The First Office Action, and First Search, dated Oct. 28, 2022 for Application No. CN 201880017019.3, 10 pgs.
International Search Report and Written Opinion dated Jul. 7, 2022 for Application No. PCT/US2022/016535, 15 pgs.
U.S. Appl. No. 63/149,742, filed Feb. 16, 2021.
U.S. Appl. No. 63/162,369, filed Mar. 17, 2021.

* cited by examiner

Figure 2

A Result of the N-terminal sequencing: NAPGE

B MKMASNDASPSDGSTANLVPEVNNEVMALEPVVGAAIAAPVAGQQNVIDPWIR NNFVQAPGGEFTVSPR*NAPGEILWSAPLGPDLNPYLSHLARMYNGYAGGFEVQ VILAGNAFTAGKVIFAAVPPNFPTEGLSPSQVTMFPHIIVDVRQLEPVLIPLPDVRNN FYHYNQSNDSTIKLIAMLYTPLRANNAGDDVFTVSCRVLTRPSPDFDFIFLVPPTVE-GGGG-HHHHHH (Calculated MW of $S_{R69A}$=24585.89 Da) (SEQ ID NO 1)

C

| | | |
|---|---|---|
| GII.4-AY038600 | EFTVSPRNAPGEILWSAP | (SEQ ID NO 2) |
| GII.20-EU373815 | EFTVSPRNAPGEVLLNLP | (SEQ ID NO 3) |
| GII.1-U07611 | EFTVSPRNSPGEILLNLE | (SEQ ID NO 4) |
| GII.12-AJ277618 | XFTVSPRNSPGEVLLNLE | (SEQ ID NO 5) |
| GII.16-AY502010 | EFTVSPRNSPGEILLNLE | (SEQ ID NO 6) |
| GII.22-AB083780 | EFTISPRNSPGEILLNME | (SEQ ID NO 7) |
| GII.2-AY134748 | EFTVSPRNAPGEVLLNLE | (SEQ ID NO 8) |
| GII.5-AF397156 | EFTVSPRNSPGEILVNLE | (SEQ ID NO 9) |
| GII.10-AF427118 | EFTVSPRNSPGEVLLNLE | (SEQ ID NO 10) |
| GII.13-AY113106 | EFTVSPRNSPGEILLNLE | (SEQ ID NO 11) |
| GII.21-AY675554 | EFTVSPRNSPGEILMNLE | (SEQ ID NO 12) |
| GII.17-AY502009 | EFTVSPRNSPGEILLNLE | (SEQ ID NO 13) |
| GII.11-AB074893 | EFTVSPRNAPGEILLDLE | (SEQ ID NO 14) |
| GII.19-AY823306 | EFTVSPRNAPGEILLDLE | (SEQ ID NO 15) |
| GII.18-AY823305 | EFTVSPRNSPGEVLLNLE | (SEQ ID NO 16) |
| GII.3-U22498 | EFTVSPRNSPGEVLLNLE | (SEQ ID NO 17) |
| GII.6-AF414407 | EFTVSPRNSPGEMLLNLE | (SEQ ID NO 18) |
| GII.8-AF195848 | EFTVSPRNAPGEFLLDLE | (SEQ ID NO 19) |
| GII.9-AAK84676 | EFTVSPRNAPGEFLLDLE | (SEQ ID NO 20) |
| GII.14-AY130761 | EFTVSPRNSPGELLLDLE | (SEQ ID NO 21) |
| GII.7-AJ277608 | EFTVSPRNSPGEILLDLE | (SEQ ID NO 22) |
| GII.15-AY130762 | EFTVSPRNAPGEVLIDLE | (SEQ ID NO 23) |
| | **:****:***.* . | |

D

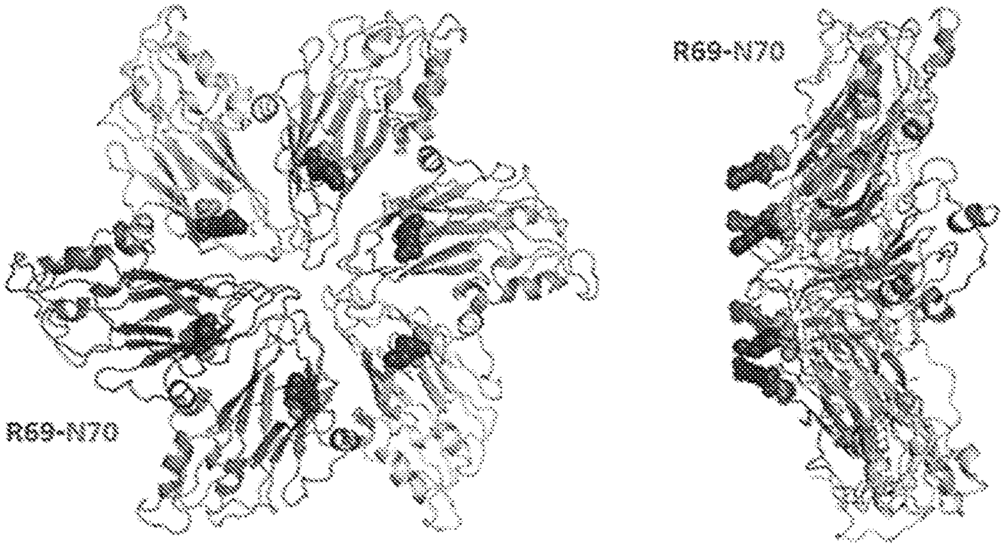

A Plasmid construct B M S₆₀ₐ-VP8 protein C Gel filtration of the S₆₀ₐ-VP8 proteins

D EM micrograph of the S₆₀-VP8 chimeric particles.

E ESI-MS analysis of the S₆₀ₐ-VP

SEQUENCE LISTING

```
<160> NUMBER OF SEQ ID NOS: 54

<210> SEQ ID NO 1
<211> LENGTH: 231
<212> TYPE: PRT
<213> ORGANISM: Artificial Sequence
<220> FEATURE:
<223> OTHER INFORMATION: SR69A protein with hinge, linker (GGGG), and
      the Hisx6 peptide

<400> SEQUENCE: 1

Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
```

-continued

```
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Gly Gly Gly
    210                 215                 220

Gly His His His His His His
225                 230


<210> SEQ ID NO 2
<211> LENGTH: 18
<212> TYPE: PRT
<213> ORGANISM: Norovirus Norwalk Virus

<400> SEQUENCE: 2

Glu Phe Thr Val Ser Pro Arg Asn Ala Pro Gly Glu Ile Leu Trp Ser
1               5                   10                  15

Ala Pro


<210> SEQ ID NO 3
<211> LENGTH: 18
<212> TYPE: PRT
<213> ORGANISM: Norovirus Norwalk Virus

<400> SEQUENCE: 3

Glu Phe Thr Val Ser Pro Arg Asn Ala Pro Gly Glu Val Leu Leu Asn
1               5                   10                  15

Leu Pro


<210> SEQ ID NO 4
<211> LENGTH: 18
<212> TYPE: PRT
<213> ORGANISM: Norovirus Norwalk Virus

<400> SEQUENCE: 4

Glu Phe Thr Val Ser Pro Arg Asn Ser Pro Gly Glu Ile Leu Leu Asn
1               5                   10                  15

Leu Glu


<210> SEQ ID NO 5
<211> LENGTH: 18
<212> TYPE: PRT
<213> ORGANISM: Norovirus Norwalk Virus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 5

Xaa Phe Thr Val Ser Pro Arg Asn Ser Pro Gly Glu Val Leu Leu Asn
1               5                   10                  15

Leu Glu


<210> SEQ ID NO 6
<211> LENGTH: 18
<212> TYPE: PRT
<213> ORGANISM: Norovirus Norwalk Virus

<400> SEQUENCE: 6

Glu Phe Thr Val Ser Pro Arg Asn Ser Pro Gly Glu Ile Leu Leu Asn
```

-continued

```
1               5                   10                  15

Leu Glu


<210> SEQ ID NO 7
<211> LENGTH: 18
<212> TYPE: PRT
<213> ORGANISM: Norovirus Norwalk Virus

<400> SEQUENCE: 7

Glu Phe Thr Ile Ser Pro Arg Asn Ser Pro Gly Glu Ile Leu Leu Asn
1               5                   10                  15

Met Glu


<210> SEQ ID NO 8
<211> LENGTH: 18
<212> TYPE: PRT
<213> ORGANISM: Norovirus Norwalk Virus

<400> SEQUENCE: 8

Glu Phe Thr Val Ser Pro Arg Asn Ala Pro Gly Glu Val Leu Leu Asn
1               5                   10                  15

Leu Glu


<210> SEQ ID NO 9
<211> LENGTH: 18
<212> TYPE: PRT
<213> ORGANISM: Norovirus Norwalk Virus

<400> SEQUENCE: 9

Glu Phe Thr Val Ser Pro Arg Asn Ser Pro Gly Glu Ile Leu Val Asn
1               5                   10                  15

Leu Glu


<210> SEQ ID NO 10
<211> LENGTH: 18
<212> TYPE: PRT
<213> ORGANISM: Norovirus Norwalk Virus

<400> SEQUENCE: 10

Glu Phe Thr Val Ser Pro Arg Asn Ser Pro Gly Glu Val Leu Leu Asn
1               5                   10                  15

Leu Glu


<210> SEQ ID NO 11
<211> LENGTH: 18
<212> TYPE: PRT
<213> ORGANISM: Norovirus Norwalk Virus

<400> SEQUENCE: 11

Glu Phe Thr Val Ser Pro Arg Asn Ser Pro Gly Glu Ile Leu Leu Asn
1               5                   10                  15

Leu Glu


<210> SEQ ID NO 12
<211> LENGTH: 18
<212> TYPE: PRT
<213> ORGANISM: Norovirus Norwalk Virus

<400> SEQUENCE: 12

Glu Phe Thr Val Ser Pro Arg Asn Ser Pro Gly Glu Ile Leu Met Asn
1               5                   10                  15
```

Leu Glu

<210> SEQ ID NO 13
<211> LENGTH: 18
<212> TYPE: PRT
<213> ORGANISM: Norovirus Norwalk Virus

<400> SEQUENCE: 13

Glu Phe Thr Val Ser Pro Arg Asn Ser Pro Gly Glu Ile Leu Leu Asn
1 5 10 15

Leu Glu

<210> SEQ ID NO 14
<211> LENGTH: 18
<212> TYPE: PRT
<213> ORGANISM: Norovirus Norwalk Virus

<400> SEQUENCE: 14

Glu Phe Thr Val Ser Pro Arg Asn Ala Pro Gly Glu Ile Leu Leu Asp
1 5 10 15

Leu Glu

<210> SEQ ID NO 15
<211> LENGTH: 18
<212> TYPE: PRT
<213> ORGANISM: Norovirus Norwalk Virus

<400> SEQUENCE: 15

Glu Phe Thr Val Ser Pro Arg Asn Ala Pro Gly Glu Ile Leu Leu Asp
1 5 10 15

Leu Glu

<210> SEQ ID NO 16
<211> LENGTH: 18
<212> TYPE: PRT
<213> ORGANISM: Norovirus Norwalk Virus

<400> SEQUENCE: 16

Glu Phe Thr Val Ser Pro Arg Asn Ser Pro Gly Glu Val Leu Leu Asn
1 5 10 15

Leu Glu

<210> SEQ ID NO 17
<211> LENGTH: 18
<212> TYPE: PRT
<213> ORGANISM: Norovirus Norwalk Virus

<400> SEQUENCE: 17

Glu Phe Thr Val Ser Pro Arg Asn Ser Pro Gly Glu Val Leu Leu Asn
1 5 10 15

Leu Glu

<210> SEQ ID NO 18
<211> LENGTH: 18
<212> TYPE: PRT
<213> ORGANISM: Norovirus Norwalk Virus

<400> SEQUENCE: 18

Glu Phe Thr Val Ser Pro Arg Asn Ser Pro Gly Glu Met Leu Leu Asn
1 5 10 15

-continued

Leu Glu

<210> SEQ ID NO 19
<211> LENGTH: 18
<212> TYPE: PRT
<213> ORGANISM: Norovirus Norwalk Virus

<400> SEQUENCE: 19

Glu Phe Thr Val Ser Pro Arg Asn Ala Pro Gly Glu Phe Leu Leu Asp
1 5 10 15

Leu Glu

<210> SEQ ID NO 20
<211> LENGTH: 18
<212> TYPE: PRT
<213> ORGANISM: Norovirus Norwalk Virus

<400> SEQUENCE: 20

Glu Phe Thr Val Ser Pro Arg Asn Ala Pro Gly Glu Phe Leu Leu Asp
1 5 10 15

Leu Glu

<210> SEQ ID NO 21
<211> LENGTH: 18
<212> TYPE: PRT
<213> ORGANISM: Norovirus Norwalk Virus

<400> SEQUENCE: 21

Glu Phe Thr Val Ser Pro Arg Asn Ser Pro Gly Glu Leu Leu Leu Asp
1 5 10 15

Leu Glu

<210> SEQ ID NO 22
<211> LENGTH: 18
<212> TYPE: PRT
<213> ORGANISM: Norovirus Norwalk Virus

<400> SEQUENCE: 22

Glu Phe Thr Val Ser Pro Arg Asn Ser Pro Gly Glu Ile Leu Leu Asp
1 5 10 15

Leu Glu

<210> SEQ ID NO 23
<211> LENGTH: 18
<212> TYPE: PRT
<213> ORGANISM: Norovirus Norwalk Virus

<400> SEQUENCE: 23

Glu Phe Thr Val Ser Pro Arg Asn Ala Pro Gly Glu Val Leu Ile Asp
1 5 10 15

Leu Glu

<210> SEQ ID NO 24
<211> LENGTH: 663
<212> TYPE: DNA
<213> ORGANISM: Norovirus Norwalk virus

<400> SEQUENCE: 24
atgaagatgg cgtcgaatga cgccagccca tctgatgggt ccacagccaa cctcgtccca 60
gaggtcaaca atgaggttat ggctttggag cccgttgttg gtgccgctat tgcggcacct 120

```
gtggcgggcc aacaaaacgt aattgacccc tggattagga ataattttgt acaagcccct    180

ggtggagagt ttacagtatc ccctagaaac gctccaggtg agatactatg gagcgcgccc    240

ttgggccctg atttgaaccc ctacctttct catttggcca gaatgtacaa tggttatgca    300

ggtggttttg aagtgcaggt aatcctcgcg gggaacgcgt tcaccgccgg gaaagtcata    360

tttgcagcag tcccaccaaa ttttccaact gaaggcttga gccccagcca ggttactatg    420

ttcccccata taatagtaga tgttaggcaa ttggaacctg tgttgatccc cttacctgat    480

gttaggaata acttctatca ttacaatcaa tcaaatgatt ctaccattaa attgatagca    540

atgctgtata caccacttag gctaataat gctggggatg atgtcttcac agtctcttgt    600

cgagtcctca cgaggccatc ccccgatttt gatttcatat tcttggtgcc acccacagtt    660

gaa                                                                 663
```

<210> SEQ ID NO 25
<211> LENGTH: 221
<212> TYPE: PRT
<213> ORGANISM: Norovirus Norwalk virus

<400> SEQUENCE: 25

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu
    210                 215                 220
```

<210> SEQ ID NO 26
<211> LENGTH: 663
<212> TYPE: DNA
<213> ORGANISM: Artificial Sequence
<220> FEATURE:
<223> OTHER INFORMATION: SR69A sequence

<400> SEQUENCE: 26

-continued

```
atgaagatgg cgtcgaatga cgccagccca tctgatgggt ccacagccaa cctcgtccca     60

gaggtcaaca atgaggttat ggctttggag cccgttgttg gtgccgctat tgcggcacct    120

gtggcgggcc aacaaaacgt aattgacccc tggattagga ataattttgt acaagcccct    180

ggtggagagt ttacagtatc ccctgcaaac gctccaggtg agatactatg gagcgcgccc    240

ttgggccctg atttgaaccc ctacctttct catttggcca gaatgtacaa tggttatgca    300

ggtggttttg aagtgcaggt aatcctcgcg gggaacgcgt tcaccgccgg gaaagtcata    360

tttgcagcag tcccaccaaa ttttccaact gaaggcttga gccccagcca ggttactatg    420

ttcccccata taatagtaga tgttaggcaa ttggaacctg tgttgatccc cttacctgat    480

gttaggaata acttctatca ttacaatcaa tcaaatgatt ctaccattaa attgatagca    540

atgctgtata caccacttag ggctaataat gctggggatg atgtcttcac agtctcttgt    600

cgagtcctca cgaggccatc cccgattttt gatttcatat tcttggtgcc acccacagtt    660

gaa                                                                  663
```

<210> SEQ ID NO 27
<211> LENGTH: 221
<212> TYPE: PRT
<213> ORGANISM: Artificial Sequence
<220> FEATURE:
<223> OTHER INFORMATION: SR69A sequence (protein)

<400> SEQUENCE: 27

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Ala Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu
    210                 215                 220
```

<210> SEQ ID NO 28

<211> LENGTH: 1152
<212> TYPE: DNA
<213> ORGANISM: Artificial Sequence
<220> FEATURE:
<223> OTHER INFORMATION: SR69A-VP8 chimeric protein (Nucleotide sequences of Sr69A-VP8)

<400> SEQUENCE: 28

```
atgaagatgg cgtcgaatga cgccagccca tctgatgggt ccacagccaa cctcgtccca     60

gaggtcaaca atgaggttat ggctttggag cccgttgttg gtgccgctat tgcggcacct    120

gtggcgggcc aacaaaacgt aattgacccc tggattagga ataattttgt acaagcccct    180

ggtggagagt ttacagtatc ccctgcaaac gctccaggtg agatactatg gagcgcgccc    240

ttgggccctg atttgaaccc ctacctttct catttggcca gaatgtacaa tggttatgca    300

ggtggttttg aagtgcaggt aatcctcgcg ggaacgcgt tcaccgccgg gaaagtcata     360

tttgcagcag tcccaccaaa ttttccaact gaaggcttga gccccagcca ggttactatg    420

ttcccccata taatagtaga tgttaggcaa ttggaacctg tgttgatccc cttacctgat    480

gttaggaata acttctatca ttacaatcaa tcaaatgatt ctaccattaa attgatagca    540

atgctgtata caccacttag ggctaataat gctggggatg atgtcttcac agtctcttgt    600

cgagtcctca cgaggccatc ccccgatttt gatttcatat tcttggtgcc acccacagtt    660

gaacatcacc atcacttaga tggtccttat caacctacta catttacacc acctactgat    720

tactggatac ttattaattc aaatacaaat ggagtagtat acgagagtac aaataatagt    780

gacttttgga ctgcagtcat tgctgttgaa ccgcacgtca atccagtaga tagacaatat    840

aatgtatttg gtgaaaataa acaatttaat gtaagaaatg attcagataa atggaagttt    900

ttagaaatgt ttagaggcag tagtcaaaat gacttttata atagacgtac actaacttct    960

gatactagac tcgtgggaat attaaaatat ggtggaagaa tatggacatt tcatggtgaa   1020

acaccgaggg ctactactga tagctcaaac actgcaaatt tgaacggtat atcaattaca   1080

attcattcag aattttatat tattccaagg tcccaagagt ctaagtgtaa tgaatatatt   1140

aacaacggtc ta                                                       1152
```

<210> SEQ ID NO 29
<211> LENGTH: 384
<212> TYPE: PRT
<213> ORGANISM: Artificial Sequence
<220> FEATURE:
<223> OTHER INFORMATION: SR69A-VP8 chimeric protein

<400> SEQUENCE: 29

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Ala Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110
```

```
Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu His His His
    210                 215                 220

His Leu Asp Gly Pro Tyr Gln Pro Thr Thr Phe Thr Pro Pro Thr Asp
225                 230                 235                 240

Tyr Trp Ile Leu Ile Asn Ser Asn Thr Asn Gly Val Val Tyr Glu Ser
                245                 250                 255

Thr Asn Asn Ser Asp Phe Trp Thr Ala Val Ile Ala Val Glu Pro His
            260                 265                 270

Val Asn Pro Val Asp Arg Gln Tyr Asn Val Phe Gly Glu Asn Lys Gln
        275                 280                 285

Phe Asn Val Arg Asn Asp Ser Asp Lys Trp Lys Phe Leu Glu Met Phe
    290                 295                 300

Arg Gly Ser Ser Gln Asn Asp Phe Tyr Asn Arg Arg Thr Leu Thr Ser
305                 310                 315                 320

Asp Thr Arg Leu Val Gly Ile Leu Lys Tyr Gly Gly Arg Ile Trp Thr
                325                 330                 335

Phe His Gly Glu Thr Pro Arg Ala Thr Thr Asp Ser Ser Asn Thr Ala
            340                 345                 350

Asn Leu Asn Gly Ile Ser Ile Thr Ile His Ser Glu Phe Tyr Ile Ile
        355                 360                 365

Pro Arg Ser Gln Glu Ser Lys Cys Asn Glu Tyr Ile Asn Asn Gly Leu
    370                 375                 380


<210> SEQ ID NO 30
<211> LENGTH: 1152
<212> TYPE: DNA
<213> ORGANISM: Artificial Sequence
<220> FEATURE:
<223> OTHER INFORMATION: SR69A/V57C/M140C-VP8

<400> SEQUENCE: 30

atgaagatgg cgtcgaatga cgccagccca tctgatgggt ccacagccaa cctcgtccca      60

gaggtcaaca atgaggttat ggctttggag cccgttgttg gtgccgctat tgcggcacct     120

gtggcgggcc aacaaaacgt aattgacccc tggattagga ataatttttg tcaagcccct     180

ggtggagagt ttacagtatc ccctgcaaac gctccaggtg agatactatg gagcgcgccc     240

ttgggccctg atttgaaccc ctacctttct catttggcca gaatgtacaa tggttatgca     300

ggtggttttg aagtgcaggt aatcctcgcg gggaacgcgt tcaccgccgg gaaagtcata     360

tttgcagcag tcccaccaaa ttttccaact gaaggcttga gccccagcca ggttacttgt     420

ttcccccata taatagtaga tgttaggcaa ttggaacctg tgttgatccc cttacctgat     480

gttaggaata acttctatca ttacaatcaa tcaaatgatt ctaccattaa attgatagca     540
```

atgctgtata caccacttag ggctaataat gctggggatg atgtcttcac agtctcttgt 600
cgagtcctca cgaggccatc cccgatttt gatttcatat tcttggtgcc acccacagtt 660
gaacatcacc atcacttaga tggtccttat caacctacta catttacacc acctactgat 720
tactggatac ttattaattc aaatacaaat ggagtagtat acgagagtac aaataatagt 780
gacttttgga ctgcagtcat tgctgttgaa ccgcacgtca atccagtaga tagacaatat 840
aatgtatttg gtgaaaataa acaatttaat gtaagaaatg attcagataa atggaagttt 900
ttagaaatgt ttagaggcag tagtcaaaat gacttttata atagacgtac actaacttct 960
gatactagac tcgtgggaat attaaaatat ggtggaagaa tatggacatt tcatggtgaa 1020
acaccgaggg ctactactga tagctcaaac actgcaaatt tgaacggtat atcaattaca 1080
attcattcag aattttatat tattccaagg tcccaagagt ctaagtgtaa tgaatatatt 1140
aacaacggtc ta 1152

<210> SEQ ID NO 31
<211> LENGTH: 384
<212> TYPE: PRT
<213> ORGANISM: Artificial Sequence
<220> FEATURE:
<223> OTHER INFORMATION: Amino acid sequences of the SR69A/V57C/M140C-
VP8

<400> SEQUENCE: 31

Met Lys Met Ala Ser Asn Asp Ala Ser Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Cys Gln Ala Pro Gly Gly Glu Phe
50 55 60

Thr Val Ser Pro Ala Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Val Ile Phe Ala Ala Val Pro Pro Asn Phe
115 120 125

Pro Thr Glu Gly Leu Ser Pro Ser Gln Val Thr Cys Phe Pro His Ile
130 135 140

Ile Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Ser Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu His His His
210 215 220

His Leu Asp Gly Pro Tyr Gln Pro Thr Thr Phe Thr Pro Pro Thr Asp
225 230 235 240

-continued

```
Tyr Trp Ile Leu Ile Asn Ser Asn Thr Asn Gly Val Val Tyr Glu Ser
                245                 250                 255

Thr Asn Asn Ser Asp Phe Trp Thr Ala Val Ile Ala Val Glu Pro His
            260                 265                 270

Val Asn Pro Val Asp Arg Gln Tyr Asn Val Phe Gly Glu Asn Lys Gln
        275                 280                 285

Phe Asn Val Arg Asn Asp Ser Asp Lys Trp Lys Phe Leu Glu Met Phe
    290                 295                 300

Arg Gly Ser Ser Gln Asn Asp Phe Tyr Asn Arg Arg Thr Leu Thr Ser
305                 310                 315                 320

Asp Thr Arg Leu Val Gly Ile Leu Lys Tyr Gly Gly Arg Ile Trp Thr
                325                 330                 335

Phe His Gly Glu Thr Pro Arg Ala Thr Thr Asp Ser Ser Asn Thr Ala
            340                 345                 350

Asn Leu Asn Gly Ile Ser Ile Thr Ile His Ser Glu Phe Tyr Ile Ile
        355                 360                 365

Pro Arg Ser Gln Glu Ser Lys Cys Asn Glu Tyr Ile Asn Asn Gly Leu
    370                 375                 380
```

<210> SEQ ID NO 32
<211> LENGTH: 1152
<212> TYPE: DNA
<213> ORGANISM: Artificial Sequence
<220> FEATURE:
<223> OTHER INFORMATION: SR69A/V57C/Q58C/S136C-VP8

<400> SEQUENCE: 32

```
atgaagatgg cgtcgaatga cgccagccca tctgatgggt ccacagccaa cctcgtccca     60

gaggtcaaca atgaggttat ggctttggag cccgttgttg gtgccgctat tgcggcacct    120

gtggcgggcc aacaaaacgt aattgacccc tggattagga ataatttttg ttgtgcccct    180

ggtggagagt ttacagtatc ccctgcaaac gctccaggtg agatactatg gagcgcgccc    240

ttgggccctg atttgaaccc ctacctttct catttggcca gaatgtacaa tggttatgca    300

ggtggttttg aagtgcaggt aatcctcgcg gggaacgcgt tcaccgccgg gaaagtcata    360

tttgcagcag tcccaccaaa ttttccaact gaaggcttga gcccctgtca ggttactatg    420

ttcccccata taatagtaga tgttaggcaa ttggaacctg tgttgatccc cttacctgat    480

gttaggaata acttctatca ttacaatcaa tcaaatgatt ctaccattaa attgatagca    540

atgctgtata caccacttag ggctaataat gctggggatg atgtcttcac agtctcttgt    600

cgagtcctca cgaggccatc ccccgatttt gatttcatat tcttggtgcc acccacagtt    660

gaacatcacc atcacttaga tggtccttat caacctacta catttacacc acctactgat    720

tactggatac ttattaattc aaatacaaat ggagtagtat acgagagtac aaataatagt    780

gacttttgga ctgcagtcat tgctgttgaa ccgcacgtca atccagtaga tagacaatat    840

aatgtatttg gtgaaaataa acaatttaat gtaagaaatg attcagataa atggaagttt    900

ttagaaatgt ttagaggcag tagtcaaaat gacttttata atagacgtac actaacttct    960

gatactagac tcgtgggaat attaaaatat ggtggaagaa tatggacatt tcatggtgaa   1020

acaccgaggg ctactactga tagctcaaac actgcaaatt tgaacggtat atcaattaca   1080

attcattcag aattttatat tattccaagg tcccaagagt ctaagtgtaa tgaatatatt   1140

aacaacggtc ta                                                       1152
```

<210> SEQ ID NO 33

<211> LENGTH: 385
<212> TYPE: PRT
<213> ORGANISM: Artificial Sequence
<220> FEATURE:
<223> OTHER INFORMATION: SR69A/V57C/Q58C/S136C-VP8

<400> SEQUENCE: 33

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Cys Cys Gln Ala Pro Gly Gly Glu
    50                  55                  60

Phe Thr Val Ser Pro Ala Asn Ala Pro Gly Glu Ile Leu Trp Ser Ala
65                  70                  75                  80

Pro Leu Gly Pro Asp Leu Asn Pro Tyr Leu Ser His Leu Ala Arg Met
                85                  90                  95

Tyr Asn Gly Tyr Ala Gly Gly Phe Glu Val Gln Val Ile Leu Ala Gly
            100                 105                 110

Asn Ala Phe Thr Ala Gly Lys Val Ile Phe Ala Ala Val Pro Pro Asn
        115                 120                 125

Phe Pro Thr Glu Gly Leu Ser Pro Ser Gln Val Thr Cys Phe Pro His
    130                 135                 140

Ile Ile Val Asp Val Arg Gln Leu Glu Pro Val Leu Ile Pro Leu Pro
145                 150                 155                 160

Asp Val Arg Asn Asn Phe Tyr His Tyr Asn Gln Ser Asn Asp Ser Thr
                165                 170                 175

Ile Lys Leu Ile Ala Met Leu Tyr Thr Pro Leu Arg Ala Asn Asn Ala
            180                 185                 190

Gly Asp Asp Val Phe Thr Val Ser Cys Arg Val Leu Thr Arg Pro Ser
        195                 200                 205

Pro Asp Phe Asp Phe Ile Phe Leu Val Pro Pro Thr Val Glu His His
    210                 215                 220

His His Leu Asp Gly Pro Tyr Gln Pro Thr Thr Phe Thr Pro Pro Thr
225                 230                 235                 240

Asp Tyr Trp Ile Leu Ile Asn Ser Asn Thr Asn Gly Val Val Tyr Glu
                245                 250                 255

Ser Thr Asn Asn Ser Asp Phe Trp Thr Ala Val Ile Ala Val Glu Pro
            260                 265                 270

His Val Asn Pro Val Asp Arg Gln Tyr Asn Val Phe Gly Glu Asn Lys
        275                 280                 285

Gln Phe Asn Val Arg Asn Asp Ser Asp Lys Trp Lys Phe Leu Glu Met
    290                 295                 300

Phe Arg Gly Ser Ser Gln Asn Asp Phe Tyr Asn Arg Arg Thr Leu Thr
305                 310                 315                 320

Ser Asp Thr Arg Leu Val Gly Ile Leu Lys Tyr Gly Gly Arg Ile Trp
                325                 330                 335

Thr Phe His Gly Glu Thr Pro Arg Ala Thr Thr Asp Ser Ser Asn Thr
            340                 345                 350

Ala Asn Leu Asn Gly Ile Ser Ile Thr Ile His Ser Glu Phe Tyr Ile
        355                 360                 365

Ile Pro Arg Ser Gln Glu Ser Lys Cys Asn Glu Tyr Ile Asn Asn Gly
    370                 375                 380
```

Leu
385

<210> SEQ ID NO 34
<211> LENGTH: 477
<212> TYPE: DNA
<213> ORGANISM: Rotavirus Rotavirus A

<400> SEQUENCE: 34
ttagatggtc cttatcaacc tactacattt acaccaccta ctgattactg gatacttatt 60
aattcaaata caaatggagt agtatacgag agtacaaata atagtgactt ttggactgca 120
gtcattgctg ttgaaccgca cgtcaatcca gtagatagac aatataatgt atttggtgaa 180
aataaacaat ttaatgtaag aaatgattca gataaatgga agtttttaga aatgtttaga 240
ggcagtagtc aaaatgactt ttataataga cgtacactaa cttctgatac tagactcgtg 300
ggaatattaa aatatggtgg aagaatatgg acatttcatg gtgaaacacc gagggctact 360
actgatagct caaacactgc aaatttgaac ggtatatcaa ttacaattca ttcagaattt 420
tatattattc caaggtccca agagtctaag tgtaatgaat atattaacaa cggtcta 477

<210> SEQ ID NO 35
<211> LENGTH: 159
<212> TYPE: PRT
<213> ORGANISM: Rotavirus Rotavirus A

<400> SEQUENCE: 35

Leu Asp Gly Pro Tyr Gln Pro Thr Thr Phe Thr Pro Pro Thr Asp Tyr
1 5 10 15

Trp Ile Leu Ile Asn Ser Asn Thr Asn Gly Val Val Tyr Glu Ser Thr
20 25 30

Asn Asn Ser Asp Phe Trp Thr Ala Val Ile Ala Val Glu Pro His Val
35 40 45

Asn Pro Val Asp Arg Gln Tyr Asn Val Phe Gly Glu Asn Lys Gln Phe
50 55 60

Asn Val Arg Asn Asp Ser Asp Lys Trp Lys Phe Leu Glu Met Phe Arg
65 70 75 80

Gly Ser Ser Gln Asn Asp Phe Tyr Asn Arg Arg Thr Leu Thr Ser Asp
85 90 95

Thr Arg Leu Val Gly Ile Leu Lys Tyr Gly Gly Arg Ile Trp Thr Phe
100 105 110

His Gly Glu Thr Pro Arg Ala Thr Thr Asp Ser Ser Asn Thr Ala Asn
115 120 125

Leu Asn Gly Ile Ser Ile Thr Ile His Ser Glu Phe Tyr Ile Ile Pro
130 135 140

Arg Ser Gln Glu Ser Lys Cys Asn Glu Tyr Ile Asn Asn Gly Leu
145 150 155

<210> SEQ ID NO 36
<211> LENGTH: 1152
<212> TYPE: DNA
<213> ORGANISM: Artificial Sequence
<220> FEATURE:
<223> OTHER INFORMATION: SR69A/V57C/Q58C/S136C/M140C-VP8 chimeric proteins (the expression construct was made by cloning these sequences into the pET-24 vector)

<400> SEQUENCE: 36
atgaagatgg cgtcgaatga cgccagccca tctgatgggt ccacagccaa cctcgtccca 60

```
gaggtcaaca atgaggttat ggctttggag cccgttgttg gtgccgctat tgcggcacct    120

gtggcgggcc aacaaaacgt aattgacccc tggattagga ataatttttg ttgtgcccct    180

ggtggagagt ttacagtatc ccctgcaaac gctccaggtg agatactatg gagcgcgccc    240

ttgggccctg atttgaaccc ctacctttct catttggcca gaatgtacaa tggttatgca    300

ggtggttttg aagtgcaggt aatcctcgcg ggaacgcgt tcaccgccgg gaaagtcata     360

tttgcagcag tcccaccaaa ttttccaact gaaggcttga gcccctgtca ggttacttgt    420

ttcccccata taatagtaga tgttaggcaa ttggaacctg tgttgatccc cttacctgat    480

gttaggaata acttctatca ttacaatcaa tcaaatgatt ctaccattaa attgatagca    540

atgctgtata caccacttag ggctaataat gctggggatg atgtcttcac agtctcttgt    600

cgagtcctca cgaggccatc cccgattttt gatttcatat tcttggtgcc acccacagtt    660

gaacatcacc atcacttaga tggtccttat caacctacta catttacacc acctactgat    720

tactggatac ttattaattc aaatacaaat ggagtagtat acgagagtac aaataatagt    780

gacttttgga ctgcagtcat tgctgttgaa ccgcacgtca atccagtaga tagacaatat    840

aatgtatttg gtgaaaataa acaatttaat gtaagaaatg attcagataa atggaagttt    900

ttagaaatgt ttagaggcag tagtcaaaat gacttttata atagacgtac actaacttct    960

gatactagac tcgtgggaat attaaaatat ggtggaagaa tatggacatt tcatggtgaa   1020

acaccgaggg ctactactga tagctcaaac actgcaaatt tgaacggtat atcaattaca   1080

attcattcag aattttatat tattccaagg tcccaagagt ctaagtgtaa tgaatatatt   1140

aacaacggtc ta                                                       1152
```

<210> SEQ ID NO 37
<211> LENGTH: 385
<212> TYPE: PRT
<213> ORGANISM: Artificial Sequence
<220> FEATURE:
<223> OTHER INFORMATION: Amino acid sequences of the SR69A/V57C/Q58/S136C/M140C-VP8

<400> SEQUENCE: 37

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Cys Cys Gln Ala Pro Gly Gly Glu
    50                  55                  60

Phe Thr Val Ser Pro Ala Asn Ala Pro Gly Glu Ile Leu Trp Ser Ala
65                  70                  75                  80

Pro Leu Gly Pro Asp Leu Asn Pro Tyr Leu Ser His Leu Ala Arg Met
                85                  90                  95

Tyr Asn Gly Tyr Ala Gly Gly Phe Glu Val Gln Val Ile Leu Ala Gly
            100                 105                 110

Asn Ala Phe Thr Ala Gly Lys Val Ile Phe Ala Ala Val Pro Pro Asn
        115                 120                 125

Phe Pro Thr Glu Gly Leu Ser Pro Ser Gln Val Thr Cys Phe Pro His
    130                 135                 140

Ile Ile Val Asp Val Arg Gln Leu Glu Pro Val Leu Ile Pro Leu Pro
145                 150                 155                 160
```

```
Asp Val Arg Asn Asn Phe Tyr His Tyr Asn Gln Ser Asn Asp Ser Thr
                165                 170                 175

Ile Lys Leu Ile Ala Met Leu Tyr Thr Pro Leu Arg Ala Asn Asn Ala
            180                 185                 190

Gly Asp Asp Val Phe Thr Val Ser Cys Arg Val Leu Thr Arg Pro Ser
        195                 200                 205

Pro Asp Phe Asp Phe Ile Phe Leu Val Pro Pro Thr Val Glu His His
    210                 215                 220

His His Leu Asp Gly Pro Tyr Gln Pro Thr Thr Phe Thr Pro Pro Thr
225                 230                 235                 240

Asp Tyr Trp Ile Leu Ile Asn Ser Asn Thr Asn Gly Val Val Tyr Glu
                245                 250                 255

Ser Thr Asn Asn Ser Asp Phe Trp Thr Ala Val Ile Ala Val Glu Pro
            260                 265                 270

His Val Asn Pro Val Asp Arg Gln Tyr Asn Val Phe Gly Glu Asn Lys
        275                 280                 285

Gln Phe Asn Val Arg Asn Asp Ser Asp Lys Trp Lys Phe Leu Glu Met
    290                 295                 300

Phe Arg Gly Ser Ser Gln Asn Asp Phe Tyr Asn Arg Arg Thr Leu Thr
305                 310                 315                 320

Ser Asp Thr Arg Leu Val Gly Ile Leu Lys Tyr Gly Gly Arg Ile Trp
                325                 330                 335

Thr Phe His Gly Glu Thr Pro Arg Ala Thr Thr Asp Ser Ser Asn Thr
            340                 345                 350

Ala Asn Leu Asn Gly Ile Ser Ile Thr Ile His Ser Glu Phe Tyr Ile
        355                 360                 365

Ile Pro Arg Ser Gln Glu Ser Lys Cys Asn Glu Tyr Ile Asn Asn Gly
    370                 375                 380

Leu
385
```

<210> SEQ ID NO 38
<211> LENGTH: 1152
<212> TYPE: DNA
<213> ORGANISM: Artificial Sequence
<220> FEATURE:
<223> OTHER INFORMATION: Nucleotide sequences of S-VP8

<400> SEQUENCE: 38

```
atgaagatgg cgtcgaatga cgccagccca tctgatgggt ccacagccaa cctcgtccca      60

gaggtcaaca atgaggttat ggctttggag cccgttgttg gtgccgctat tgcggcacct     120

gtggcgggcc aacaaaacgt aattgacccc tggattagga ataattttgt acaagcccct     180

ggtggagagt ttacagtatc ccctagaaac gctccaggtg agatactatg gagcgcgccc     240

ttgggccctg atttgaaccc ctacctttct catttggcca gaatgtacaa tggttatgca     300

ggtggttttg aagtgcaggt aatcctcgcg gggaacgcgt tcaccgccgg gaaagtcata     360

tttgcagcag tcccaccaaa ttttccaact gaaggcttga gccccagcca ggttactatg     420

ttcccccata taatagtaga tgttaggcaa ttggaacctg tgttgatccc cttacctgat     480

gttaggaata acttctatca ttacaatcaa tcaaatgatt ctaccattaa attgatagca     540

atgctgtata caccacttag ggctaataat gctggggatg atgtcttcac agtctcttgt     600

cgagtcctca cgaggccatc ccccgatttt gatttcatat tcttggtgcc acccacagtt     660

gaacatcacc atcacttaga tggtccttat caacctacta catttacacc acctactgat     720
```

-continued

```
tactggatac ttattaattc aaatacaaat ggagtagtat acgagagtac aaataatagt    780

gacttttgga ctgcagtcat tgctgttgaa ccgcacgtca atccagtaga tagacaatat    840

aatgtatttg gtgaaaataa acaatttaat gtaagaaatg attcagataa atggaagttt    900

ttagaaatgt ttagaggcag tagtcaaaat gacttttata atagacgtac actaacttct    960

gatactagac tcgtgggaat attaaaatat ggtggaagaa tatggacatt tcatggtgaa   1020

acaccgaggg ctactactga tagctcaaac actgcaaatt tgaacggtat atcaattaca   1080

attcattcag aattttatat tattccaagg tcccaagagt ctaagtgtaa tgaatatatt   1140

aacaacggtc ta                                                        1152
```

```
<210> SEQ ID NO 39
<211> LENGTH: 383
<212> TYPE: PRT
<213> ORGANISM: Artificial Sequence
<220> FEATURE:
<223> OTHER INFORMATION: Amino acid sequences of S-VP8

<400> SEQUENCE: 39

Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu His His His
    210                 215                 220

His Leu Asp Gly Pro Tyr Gln Pro Thr Thr Phe Thr Pro Pro Thr Asp
225                 230                 235                 240

Tyr Trp Ile Leu Ile Asn Ser Asn Thr Asn Gly Val Val Tyr Glu Ser
                245                 250                 255

Thr Asn Asn Ser Asp Phe Trp Thr Ala Val Ile Ala Val Glu Pro His
            260                 265                 270

Val Asn Pro Val Asp Arg Gln Tyr Asn Val Phe Gly Glu Asn Lys Gln
```

```
        275                 280                 285

Phe Asn Val Arg Asn Asp Ser Asp Lys Trp Lys Phe Leu Glu Phe Arg
    290                 295                 300

Gly Ser Ser Gln Asn Asp Phe Tyr Asn Arg Arg Thr Leu Thr Ser Asp
305                 310                 315                 320

Thr Arg Leu Val Gly Ile Leu Lys Tyr Gly Gly Arg Ile Trp Thr Phe
                325                 330                 335

His Gly Glu Thr Pro Arg Ala Thr Thr Asp Ser Ser Asn Thr Ala Asn
            340                 345                 350

Leu Asn Gly Ile Ser Ile Thr Ile His Ser Glu Phe Tyr Ile Ile Pro
        355                 360                 365

Arg Ser Gln Glu Ser Lys Cys Asn Glu Tyr Ile Asn Asn Gly Leu
    370                 375                 380
```

<210> SEQ ID NO 40
<211> LENGTH: 1149
<212> TYPE: DNA
<213> ORGANISM: Artificial Sequence
<220> FEATURE:
<223> OTHER INFORMATION: Nucleotide sequences of the SR69A/V57C/Q58C/S136C-mVP8 (the expression construct was made by cloning these sequences into the pET-24 vector)

<400> SEQUENCE: 40

```
atgaagatgg cgtcgaatga cgccagccca tctgatgggt ccacagccaa cctcgtccca     60

gaggtcaaca atgaggttat ggctttggag cccgttgttg gtgccgctat tgcggcacct    120

gtggcgggcc aacaaaacgt aattgacccc tggattagga ataatttttg ttgtgcccct    180

ggtggagagt ttacagtatc ccctgcaaac gctccaggtg agatactatg gagcgcgccc    240

ttgggccctg atttgaaccc ctacctttct catttggcca gaatgtacaa tggttatgca    300

ggtggttttg aagtgcaggt aatcctcgcg gggaacgcgt tcaccgccgg gaaagtcata    360

tttgcagcag tcccaccaaa ttttccaact gaaggcttga gcccctgtca ggttactatg    420

ttcccccata taatagtaga tgttaggcaa ttggaacctg tgttgatccc cttacctgat    480

gttaggaata acttctatca ttacaatcaa tcaaatgatt ctaccattaa attgatagca    540

atgctgtata caccacttag ggctaataat gctggggatg atgtcttcac agtctcttgt    600

cgagtcctca cgaggccatc ccccgatttt gatttcatat tcttggtgcc acccacagtt    660

gaacatcacc atcaccttga tggaccatac caaccaatag cgttcagtcc gccgccagag    720

tactatattc tactctcccc gactgcaccc ggagtaatcg ctgaatgtac gaatactgtc    780

aaccgctgga tagcaatcat agctatagag ccaaacgtgt caccaacaaa tcgtacctac    840

acattgttcg gaattactga acagctaaca gtagaaaaca gctccgtgga taaatggaag    900

tttatagact tcatgaaaac tccaacaact ggcagctacg tccgttataa cattttgttg    960

tctagcacta agctatgcgc agtggcgaag cacacggaca atttatactc ctatgttgga   1020

gaaacgccta ctgcaggtca ggcatactac tcttctttca atatatttaa cctaaccgcg   1080

cactgtgact tctacattat accatggtcg cagcaatcgt tgtgcacgca atacgttaat   1140

aacggatta                                                           1149
```

<210> SEQ ID NO 41
<211> LENGTH: 383
<212> TYPE: PRT
<213> ORGANISM: Artificial Sequence
<220> FEATURE:
<223> OTHER INFORMATION: Amino acid sequences of the -continued SR69A/V57C/Q58C/S136C-mVP8

<400> SEQUENCE: 41

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Cys Cys Ala Pro Gly Gly Glu Phe
    50                  55                  60

Thr Val Ser Pro Ala Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Cys Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu His His His
    210                 215                 220

His Leu Asp Gly Pro Tyr Gln Pro Ile Ala Phe Ser Pro Pro Pro Glu
225                 230                 235                 240

Tyr Tyr Ile Leu Leu Ser Pro Thr Ala Pro Gly Val Ile Ala Glu Cys
                245                 250                 255

Thr Asn Thr Val Asn Arg Trp Ile Ala Ile Ile Ala Ile Glu Pro Asn
            260                 265                 270

Val Ser Pro Thr Asn Arg Thr Tyr Thr Leu Phe Gly Ile Thr Glu Gln
        275                 280                 285

Leu Thr Val Glu Asn Ser Ser Val Asp Lys Trp Lys Phe Ile Asp Phe
    290                 295                 300

Met Lys Thr Pro Thr Thr Gly Ser Tyr Val Arg Tyr Asn Ile Leu Leu
305                 310                 315                 320

Ser Ser Thr Lys Leu Cys Ala Val Ala Lys His Thr Asp Asn Leu Tyr
                325                 330                 335

Ser Tyr Val Gly Glu Thr Pro Thr Ala Gly Gln Ala Tyr Tyr Ser Ser
            340                 345                 350

Phe Asn Ile Phe Asn Leu Thr Ala His Cys Asp Phe Tyr Ile Ile Pro
        355                 360                 365

Trp Ser Gln Gln Ser Leu Cys Thr Gln Tyr Val Asn Asn Gly Leu
    370                 375                 380
```

<210> SEQ ID NO 42
<211> LENGTH: 498

<212> TYPE: DNA
<213> ORGANISM: Orthohepevirus Orthohepevirus A

<400> SEQUENCE: 42
cctaccccgt cacctgcccc ctcccgccct ttttcagttc ttcgtgccaa tgacgttctg 60
tggctctctc tcactgccgc tgagtacgac cagaccacgt atgggtcgtc caccaacccc 120
atgtatgtct ctgacacggt cacgtttgtt aatgtggcca ctggtgctca ggccgttgcc 180
cgctctcttg actggtctaa agtcaccctg gatggtcgtc ctcttaccac tattcagcag 240
tattctaaga cattttatgt tctcccgctt cgcgggaaac tttccttctg ggaggctagc 300
acgactaagg ccggctaccc gtataactat aatactactg ctagtgacca aattttgatt 360
gagaacgcgg ccggtcaccg tgtcgctatt tctacttata ccactagtct gggtgccggc 420
cctacctcga tctctgcggt cggtgtgcta gccccacatt cggcccttgc cgctcttgag 480
gacaccgttg attaccct 498

<210> SEQ ID NO 43
<211> LENGTH: 166
<212> TYPE: PRT
<213> ORGANISM: Orthohepevirus Orthohepevirus A

<400> SEQUENCE: 43

Pro Thr Pro Ser Pro Ala Pro Ser Arg Pro Phe Ser Val Leu Arg Ala
1 5 10 15

Asn Asp Val Leu Trp Leu Ser Leu Thr Ala Ala Glu Tyr Asp Gln Thr
20 25 30

Thr Tyr Gly Ser Ser Thr Asn Pro Met Tyr Val Ser Asp Thr Val Thr
35 40 45

Phe Val Asn Val Ala Thr Gly Ala Gln Ala Val Ala Arg Ser Leu Asp
50 55 60

Trp Ser Lys Val Thr Leu Asp Gly Arg Pro Leu Thr Thr Ile Gln Gln
65 70 75 80

Tyr Ser Lys Thr Phe Tyr Val Leu Pro Leu Arg Gly Lys Leu Ser Phe
85 90 95

Trp Glu Ala Ser Thr Thr Lys Ala Gly Tyr Pro Tyr Asn Tyr Asn Thr
100 105 110

Thr Ala Ser Asp Gln Ile Leu Ile Glu Asn Ala Ala Gly His Arg Val
115 120 125

Ala Ile Ser Thr Tyr Thr Thr Ser Leu Gly Ala Gly Pro Thr Ser Ile
130 135 140

Ser Ala Val Gly Val Leu Ala Pro His Ser Ala Leu Ala Ala Leu Glu
145 150 155 160

Asp Thr Val Asp Tyr Pro
165

<210> SEQ ID NO 44
<211> LENGTH: 624
<212> TYPE: DNA
<213> ORGANISM: Avastrovirus Avastrovirus 2

<400> SEQUENCE: 44
tccatctatt tgccactacc acaagcagat gaccaataca caccctactt tgtctataat 60
tttcaagggg aaagggtgtc aaccaccgag actggggtat tttgtctggc agccatacca 120
gctgcgacta catctagtag gtataataat cagatcacca ctccatcaat tggctacagg 180
aatgctagtg gtacaggaac atcattccta ctagatgctg catcatggtg gaatatattg 240

-continued gatgtaactc agactggagt gctttttgga caaccaagat tgggtgttgg tgtcatgcag 300
acaatgaaga ctctcaaaca gcatatcaag gattacacag agcctgcaat acagaaatat 360
tatcctggaa caactaacct tgatgagcag ttgaagcaga gattgaacct ggcagagggt 420
gacccggtca tctcaatggg ggacacaaac ggtaggaggg ctgcactctt ttataggact 480
agtgatgaaa aatatatttt atttttctca accacagaag atccaggggc acagtatcaa 540
aatctgaaaa tgttgtactt ctggaactgg tcctattctg acacaaaaca gcaatttttg 600
gaccacctta gaacagtgca gttt 624

<210> SEQ ID NO 45
<211> LENGTH: 208
<212> TYPE: PRT
<213> ORGANISM: Avastrovirus Avastrovirus 2

<400> SEQUENCE: 45

```
Ser Ile Tyr Leu Pro Leu Pro Gln Ala Asp Asp Gln Tyr Thr Pro Tyr
1               5                   10                  15

Phe Val Tyr Asn Phe Gln Gly Glu Arg Val Ser Thr Thr Glu Thr Gly
            20                  25                  30

Val Phe Cys Leu Ala Ala Ile Pro Ala Ala Thr Thr Ser Ser Arg Tyr
        35                  40                  45

Asn Asn Gln Ile Thr Thr Pro Ser Ile Gly Tyr Arg Asn Ala Ser Gly
    50                  55                  60

Thr Gly Thr Ser Phe Leu Leu Asp Ala Ala Ser Trp Trp Asn Ile Leu
65                  70                  75                  80

Asp Val Thr Gln Thr Gly Val Leu Phe Gly Gln Pro Arg Leu Gly Val
                85                  90                  95

Gly Val Met Gln Thr Met Lys Thr Leu Lys Gln His Ile Lys Asp Tyr
            100                 105                 110

Thr Glu Pro Ala Ile Gln Lys Tyr Tyr Pro Gly Thr Thr Asn Leu Asp
        115                 120                 125

Glu Gln Leu Lys Gln Arg Leu Asn Leu Ala Glu Gly Asp Pro Val Ile
    130                 135                 140

Ser Met Gly Asp Thr Asn Gly Arg Arg Ala Ala Leu Phe Tyr Arg Thr
145                 150                 155                 160

Ser Asp Glu Lys Tyr Ile Leu Phe Phe Ser Thr Thr Glu Asp Pro Gly
                165                 170                 175

Ala Gln Tyr Gln Asn Leu Lys Met Leu Tyr Phe Trp Asn Trp Ser Tyr
            180                 185                 190

Ser Asp Thr Lys Gln Gln Phe Leu Asp His Leu Arg Thr Val Gln Phe
        195                 200                 205
```

<210> SEQ ID NO 46
<211> LENGTH: 678
<212> TYPE: DNA
<213> ORGANISM: Influenzavirus A influenza A

<400> SEQUENCE: 46
tgctctaaag gtaaacgtac cgttgacctg ggtcagtgcg gtctgctggg taccatcacc 60
ggtccgccgc agtgcgacca gttcctggaa ttctctgctg acctgatcat cgaacgtcgt 120
gaaggttctg acgtttgcta cccgggtaaa ttcgttaacg aagaagctct gcgtcagatc 180
ctgcgtgaat ctggtggtat cgacaaagaa accatgggtt tcacctacaa cggtatccgt 240
accaacggtg ttacctctgc ttgcaaacgt tctggttctt ctttctacgc tgaaatgaaa 300

```
tggctgctgt ctaacaccga caacgctgct ttcccgcaga tgaccaaatc ttacaaaaac    360

acccgtaaat ctccggctat catcgtttgg ggtatccacc actctgtttc taccgctgaa    420

cagaccaaac tgtacggttc tggtaacaaa ctggttaccg ttggttcttc taactaccag    480

cagtctttcg ttccgtctcc gggtgctcgt ccgcaggtta acggtctgtc tggtcgtatc    540

gacttccact ggctgatcct gaacccgaac gacaccgtta ccttctcttt caacggtgct    600

ttcatcgctc cggaccgtgc ttctttcctg cgtggtaaat ctatgggtat ccagtctggt    660

gttcaggttg acgctaac                                                  678
```

<210> SEQ ID NO 47
<211> LENGTH: 226
<212> TYPE: PRT
<213> ORGANISM: Influenzavirus A influenza A

<400> SEQUENCE: 47

```
Cys Ser Lys Gly Lys Arg Thr Val Asp Leu Gly Gln Cys Gly Leu Leu
1               5                   10                  15

Gly Thr Ile Thr Gly Pro Pro Gln Cys Asp Gln Phe Leu Glu Phe Ser
            20                  25                  30

Ala Asp Leu Ile Ile Glu Arg Arg Glu Gly Ser Asp Val Cys Tyr Pro
        35                  40                  45

Gly Lys Phe Val Asn Glu Glu Ala Leu Arg Gln Ile Leu Arg Glu Ser
    50                  55                  60

Gly Gly Ile Asp Lys Glu Thr Met Gly Phe Thr Tyr Asn Gly Ile Arg
65                  70                  75                  80

Thr Asn Gly Val Thr Ser Ala Cys Lys Arg Ser Gly Ser Ser Phe Tyr
                85                  90                  95

Ala Glu Met Lys Trp Leu Leu Ser Asn Thr Asp Asn Ala Ala Phe Pro
            100                 105                 110

Gln Met Thr Lys Ser Tyr Lys Asn Thr Arg Lys Ser Pro Ala Ile Ile
        115                 120                 125

Val Trp Gly Ile His His Ser Val Ser Thr Ala Glu Gln Thr Lys Leu
    130                 135                 140

Tyr Gly Ser Gly Asn Lys Leu Val Thr Val Gly Ser Ser Asn Tyr Gln
145                 150                 155                 160

Gln Ser Phe Val Pro Ser Pro Gly Ala Arg Pro Gln Val Asn Gly Leu
                165                 170                 175

Ser Gly Arg Ile Asp Phe His Trp Leu Ile Leu Asn Pro Asn Asp Thr
            180                 185                 190

Val Thr Phe Ser Phe Asn Gly Ala Phe Ile Ala Pro Asp Arg Ala Ser
        195                 200                 205

Phe Leu Arg Gly Lys Ser Met Gly Ile Gln Ser Gly Val Gln Val Asp
    210                 215                 220

Ala Asn
225
```

<210> SEQ ID NO 48
<211> LENGTH: 198
<212> TYPE: DNA
<213> ORGANISM: Plasmodium falciparum

<400> SEQUENCE: 48

```
gaaccgtctg acaaacacat caaagaatac ctgaacaaaa tccagaactc tctgtctacc     60

gaatggtctc cgtgctctgt tacctgcggt aacggtatcc aggttcgtat caaaccgggt    120
```

```
tctgctaaca aaccgaaaga cgaactggac tacgctaacg acatcgaaaa aaaaatctgc    180

aaaatggaaa aatgctct                                                  198


<210> SEQ ID NO 49
<211> LENGTH: 66
<212> TYPE: PRT
<213> ORGANISM: Plasmodium falciparum

<400> SEQUENCE: 49

Glu Pro Ser Asp Lys His Ile Lys Glu Tyr Leu Asn Lys Ile Gln Asn
1               5                   10                  15

Ser Leu Ser Thr Glu Trp Ser Pro Cys Ser Val Thr Cys Gly Asn Gly
            20                  25                  30

Ile Gln Val Arg Ile Lys Pro Gly Ser Ala Asn Lys Pro Lys Asp Glu
        35                  40                  45

Leu Asp Tyr Ala Asn Asp Ile Glu Lys Lys Ile Cys Lys Met Glu Lys
    50                  55                  60

Cys Ser
65


<210> SEQ ID NO 50
<211> LENGTH: 69
<212> TYPE: DNA
<213> ORGANISM: Influenzavirus A influenza A

<400> SEQUENCE: 50

agtcttctaa ccgaggtcga aacgcctatc agaaacgaat gggggtgcag atgcaacgat     60

tcaagtgat                                                             69


<210> SEQ ID NO 51
<211> LENGTH: 23
<212> TYPE: PRT
<213> ORGANISM: Influenzavirus A influenza A

<400> SEQUENCE: 51

Ser Leu Leu Thr Glu Val Glu Thr Pro Ile Arg Asn Glu Trp Gly Cys
1               5                   10                  15

Arg Cys Asn Asp Ser Ser Asp
            20


<210> SEQ ID NO 52
<211> LENGTH: 5
<212> TYPE: PRT
<213> ORGANISM: Artificial Sequence
<220> FEATURE:
<223> OTHER INFORMATION: Penta-residue sequence

<400> SEQUENCE: 52

Asn Ala Pro Gly Glu
1               5


<210> SEQ ID NO 53
<211> LENGTH: 4
<212> TYPE: PRT
<213> ORGANISM: Artificial Sequence
<220> FEATURE:
<223> OTHER INFORMATION: Four-residue linker GGGG

<400> SEQUENCE: 53

Gly Gly Gly Gly
1
```

-continued

```
<210> SEQ ID NO 54
<211> LENGTH: 4
<212> TYPE: PRT
<213> ORGANISM: Artificial Sequence
<220> FEATURE:
<223> OTHER INFORMATION: Four-residue linker HHHH

<400> SEQUENCE: 54

His His His His
1
```

NOROVIRUS S PARTICLE BASED VACCINES AND METHODS OF MAKING AND USING SAME

CROSS-REFERENCE TO RELATED APPLICATIONS

This application claims priority to and benefit of International Application No. PCT/US18/22552, filed Mar. 15, 2018, which claims priority to and benefit of U.S. Provisional Application 62/477,481, filed Mar. 28, 2017, the contents of which are incorporated in their entirety and for all purposes.

STATEMENT REGARDING FEDERALLY-SPONSORED RESEARCH

This invention was made with government support under AI092434, AI089634 and AI114831 awarded by the National Institute of Health. The government has certain rights in the invention

BACKGROUND

RVs cause severe acute gastroenteritis primarily in infants and young children, leading to ~200,000 deaths, 2.3 million hospitalizations, and 24 million outpatient visits among children younger than 5 years of age globally each year [25-27]. The two current RV vaccines, RotaTeq (Merck) and Rotarix (GlaxoSmithKline, GSK), are effective in protecting children from severe RV cases in many developed countries [28, 29]. However, they have not shown satisfactory efficacies in most developing countries [30-32] in Africa and Asia, where most infection, morbidity, and mortality of RV occur and thus the RV vaccines are mostly needed.

BRIEF SUMMARY

Disclosed herein are vaccine compositions, in particular, polyvalent icosahedral compositions for antigen presentation. The disclosed compositions may contain an S particle made up of recombinant fusion proteins. The recombinant fusion proteins may include a norovirus (NoV) S domain protein, a linker protein domain operatively connected to the norovirus S domain protein, and an antigen protein domain operatively connected to said linker. The disclosed compositions may be used to provide

BRIEF DESCRIPTION OF THE DRAWINGS

Those of skill in the art will understand that the drawings, described below, are for illustrative purposes only. The drawings are not intended to limit the scope of the present teachings in any way.

FIG. 2. Identification of the exposed protease site in the S domain. (A) N-terminal sequencing of the protease cleaved S protein resulted in penta-residue sequences, NAPGE (SEQ ID NO: 52) (B) The S domain sequences show the same penta-residue sequences, NAPGE (SEQ ID NO: 52) (underlined), indicating the protease cutting site (star symbol). The C-terminal hinge (underlined), the four-residue linker (GGGG) (SEQ ID NO: 53), and the end fused Hisx6 peptide are indicated. The calculated molecular weight of this recombinant S domain protein is also indicated. (C) Sequence alignment among representations of all GII noroviruses indicated that the protease site is highly conserved (positions 69 and 70, highlighted). (D) Inspection of a partial GII NoV shell structure (W.J., unpublished data) in cartoon representation in different colors at 3-fold axis shows the exposed proteinase site formed by R69 (red)-N70 (cyan) in sphere representations. Left panel: top view; right panel: side view.

Figure 1:
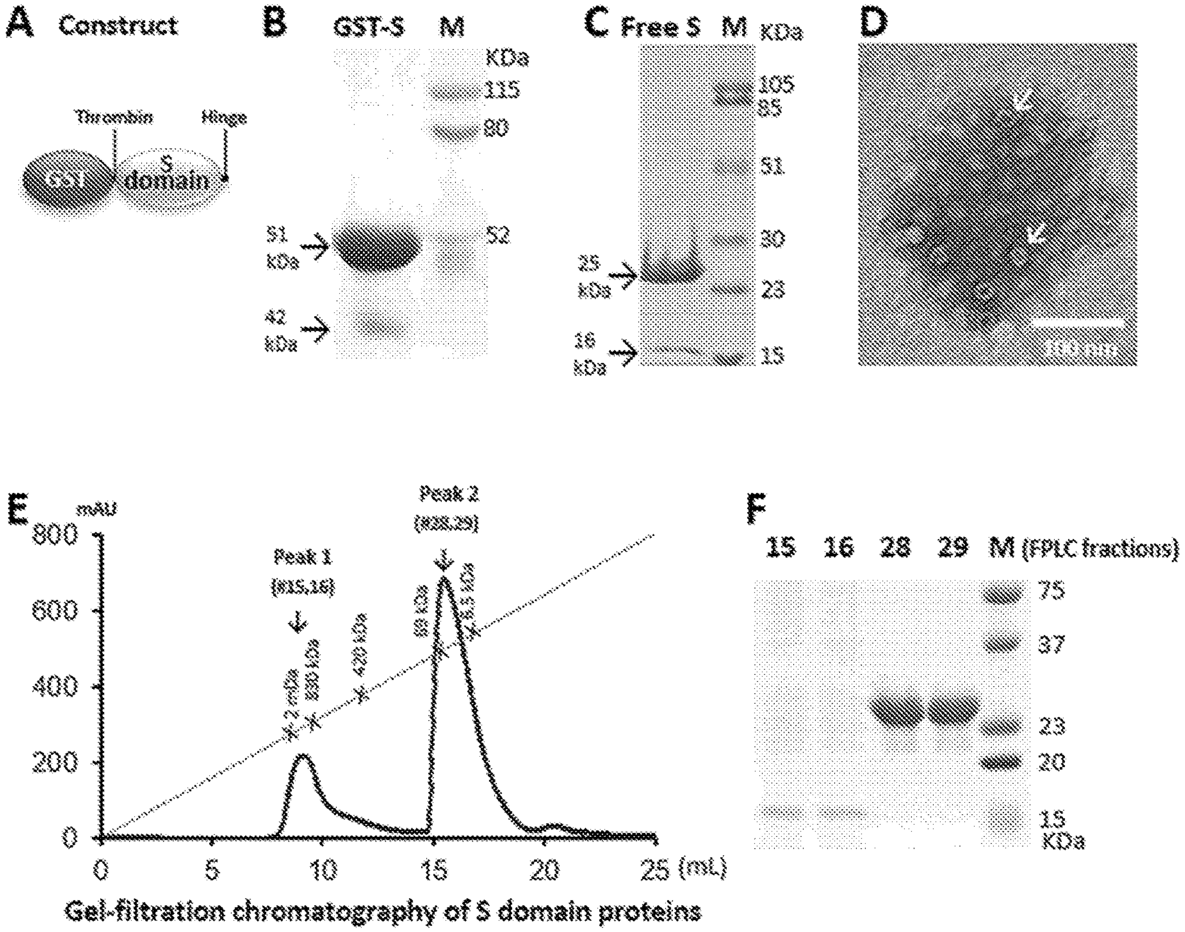
FIG. 1. Native norovirus (NoV) S domain proteins assembled into particles or complexes at low efficiency. (A) Schematic diagram of the expression construct of the GST-S domain fusion protein, showing positions of the thrombin cleavage site and the hinge. (B and C) SDS-PAGE analysis of the GST-S fusion protein (GST-S, ~51 kDa) (B) and the free S protein (~25 kDa) (C). (D) An EM micrograph of the S proteins showing few assembled S particles (arrows). (E) Elution curve of a gel-filtration chromatography of the S protein via a size-exclusion column (Superdex 200). The gel-filtration column was calibrated by the Gel Filtration Calibration Kit and the purified recombinant NoV P particles [21, 22], small P particles [20], and P dimers [11]. The elution positions of the blue Dextran 2000 (~2000 kDa, void), P particles (~830 kDa), small P particles (~420 kDa), P dimers (~69 kDa), and aprotinin (~6.5 kDa) are indicated. (F) SDS-PAGE analysis of the proteins from the two peaks, peak 1 (fraction #15 and 16) and peak 2 (fraction #28 and 29). In all SDS PAGE, Lane M is pre-stained protein markers with indicated molecular weights. Minor S protein bands at ~42, and ~16 kDa were seen in (B), (C) and (F), respectively.

BT50 against RV VP8-ligand interactions by the mouse sera after vaccination with the same three immunogens, respectively. (C) Neutralizing activity against RV infection in culture cells by mouse sera after immunization with the same three immunogens, respectively. The statistical differences between data groups are shown by star symbols (* $P<0.05$,  $P<0.01$, * $P<0.001$).

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

As used herein, the term "antigen" may be used interchangeably with the terms "immunogen" and "immunogenic antigen", as defined below. Technically speaking, an antigen is a substance that is able to combine with the products of an immune response once they are made, but is not necessarily able to induce an immune response (i.e. while all immunogens are antigens, the reverse is not true); however, the antigens that are discussed herein as the subject of the present invention are assumed to be immunogenic antigens, even when referred to as antigens.

The term "fusion protein" means a protein created through translation of a fusion gene, resulting in a single polypeptide with functional properties derived from each of the original proteins.

The term "immunity" means the state of having sufficient biological defenses to avoid infection, disease, or other biological invasion by a disease-causing organism.

The term "immunogenicity" means the ability of an immunogen to elicit a humoral and/or cell-mediated immune response.

The terms "immunogen" and "immunogenic antigen" mean a specific type of antigen that is able to induce or provoke an adaptive immune response in the form of the production of one or more antibodies.

The terms "immunogenic response" and "immune response" mean an alteration in the reactivity of an organisms' immune system in response to an immunogen. This can involve antibody production, induction of cell-mediated immunity, complement activation or development of acquired immunity or immunological tolerance to a certain disease or pathogen.

The terms "immunization" and "vaccination" mean the deliberate induction of an immune response, and involve effective manipulation of the immune system's natural specificity, as well as its inducibility. The principle behind immunization is to introduce an antigen, derived from a disease-causing organism, which stimulates the immune system to develop protective immunity against that organism, but wherein the antigen itself does not cause the pathogenic effects of that organism.

The term "infection" means the invasion of an animal or plant host's body tissues by a pathogen, as well as the multiplication of the pathogen within the body and the body's reaction to the pathogen and any toxins that it may produce.

The terms "Norovirus," "NoV", "Norwalk-like virus," or "NLV" refer to any virus of the Norovirus genus in the Calicivirus family, and includes, without limitation, the following: Norwalk Virus ("NV"), MOH, Mexico, VA 207, VA 387, 02-1419, C59, VA 115, Hawaii, Snow Mountain, Hillington, Toronto, Leeds, Amsterdam, Idaho Falls, Lordsdale, Grimsby, Southampton, Desert Shield, Birmingham, and White Rivercap. NoVs cause acute gastroenteritis in humans.

As used herein, the letter "S" means "S domain" when used in the context of the described particles, for example, in $S_{69A/58C/140C}$-VP8, which means the S-VP8 protein with 69A/58C/140C mutations. In other aspects, the nomenclature used may be, for example, S with "69A/58C/140C" denoted as a superscript.

The term "vaccine" means a biological preparation or composition that improves immunity to a particular disease. Vaccines are examples of immunogenic antigens intentionally administered to induce an immune response in the recipient.

The terms "multivalent vaccine" and "polyvalent vaccine" mean a vaccine designed to immunize against two or more strains of the same microorganism (such as NoV), or against two or more different microorganisms.

Noroviruses (NoVs) are members the Norovirus genus in the family Caliciviridae, causing epidemic acute gastroenteritis in humans with significant morbidity and mortality [4, 5]. Structurally, NoV virions are encapsulated by a protein capsid that is composed of a single major structural protein, the capsid protein or viral protein 1 (VP1). The crystal structures of NoV capsids revealed that NoV VP1 contains two principle domains, the N-terminal shell (S) and the C-terminal protruding (P) domains, linked by a short hinge [6]. The S domain builds the interior, icosahedral shell supporting the basic scaffold of a NoV virion, while the P domain constitutes the dimeric protrusions [7-10] to stabilize NoV capsid and recognize cell surface glycans as the host attachment factors or receptors [11-14].

In vitro expression of full-length NoV VP1 via a eukaryotic system resulted in self-formation of 180-valent virus-like particles (VLPs) that are structurally and antigenically similar to the authentic viral capsids [6, 15], while production of the P domain via the *E. coli* system formed P dimers that are structurally indistinguishable from those of NoV capsid [7-11, 16-19]. In addition, generation of modified NoV P domains assembled into different higher order particles or complexes, including the 12-valent small P particles [20], the 24-valent P particles [21, 22], and the 36-valent P complexes [23].

Unlike the P domain, the S domain has been less studied, although "thin layer" S particles were reported through expression of the S domain in the baculovirus/insect cell system [11, 24], likely equivalent to the 180-valent shells of NoV capsids. In this study, Applicant developed a new technology to produce unified, 60-valent S particles, referred as S60 particles, via the simple *E. coli* system and applied them as a multifunctional vaccine platform for antigen presentation for subunit vaccine development against rotavirus (RV) and other pathogens.

RVs cause severe acute gastroenteritis primarily in infants and young children, leading to ~200,000 deaths, 2.3 million hospitalizations, and 24 million outpatient visits among children younger than 5 years of age globally each year [25-27]. The two current RV vaccines, RotaTeq (Merck) and Rotarix (GlaxoSmithKline, GSK), are effective in protecting children from severe RV cases in many developed countries [28, 29]. However, they have not shown satisfactory efficacies in most developing countries [30-32] in Africa and Asia, where most infection, morbidity, and mortality of RV occur and thus the RV vaccines are mostly needed. Applicant's recent studies suggested that the low RV vaccine efficacy in the developing countries could be due to mismatched P types of the vaccines with the changing predominant RV P types in the middle- and low-income nations [33, 34]. In addition, both current live attenuated vaccines remain costly and the replications of vaccine RVs in intestine after oral administration may be the cause of the increased risk of intussusception in vaccinated children [35-41]. Thus, new generation of RV vaccines that can overcome the mentioned limitations of the two current RV live vaccine are warranted.

RV P types are determined by viral protein 4 (VP4) that constitutes the spike proteins of a RV virion. Structurally each spike protein contains two major parts, the stalk formed by VP5 and the distal head built by VP8 [42]. VP5 and VP8 are cleavage products of VP4 by a trypsin. The VP8 is responsible for interaction with RV host attachment factor or receptors that are a group of cell surface glycans, including histo-blood group antigens (HBGAs) [33, 43-45]. Previously studies have shown that VP8 antigens elicit neutralizing antibodies that inhibit RV infection and replication in culture cells and protected immunized mice from RV infection [46, 47], and therefore, the VP8 antigen is an important vaccine target against RVs [46-49].

However, many defined neutralizing antigens, including RV VP8, face a common problem of low immunogenicity for non-replicating vaccine development, due to their small sizes with low valences. This problem can be solved via fusion or conjugation of the antigens to a large, polyvalent protein platform for enhanced immunogenicity. In this study, Applicant has provided solid evidence supporting significantly enhanced immunogenicity of the RV VP8 antigens after displayed by the NoV S60 particles as an effective vaccine platform. Applicant's data indicates that the S60-VP8 particle can be easily produced, stable, and highly immunogenic toward the displayed RV VP8 antigen, and thus is a promising subunit vaccine against RV infection.

Homotypic interactions of viral capsid proteins are common, driving viral capsid self-formation. By taking advantage of such interactions of the norovirus shell (S) domain that naturally builds the interior shells of norovirus capsids, Applicant has developed methods for the production of 60-valent, icosahedral S60 particles through the simple *E. coli* system. This can been achieved by several modifications to the S domain, for example an R69A mutation to destruct an exposed proteinase cleavage site and triple cysteine mutations (V57C/Q58C/S136C) to establish inter-S domain disulfide bonds for enhanced inter-S domain interactions. The polyvalent S60 particle with 60 exposed S domain C-termini offers an ideal platform for antigen presentation, leading to enhanced immunogenicity to the displayed antigen for vaccine development. This was proven by constructing a chimeric S60 particles displaying 60 rotavirus (RV) VP8 proteins, the major RV neutralizing antigens. These S60-VP8 particles are easily produced and elicited high IgG response in mice toward the displayed VP8 antigens. The mouse antisera after immunization with the S60-VP8 particles exhibited high blockades against RV VP8 binding to its glycan ligands and high neutralizing activities against RV infection in culture cells. The three-dimensional structures of the S60 and S60-VP8 particles were studied. Finally, the S60 particle can also display other antigens, supporting the notion that the S60 particle is a multifunctional vaccine platform.

Disclosed herein are methods and compositions that can be used to form a polyvalent vaccine composition, in particular, using a modified norovirus S particle.

In one aspect, a polyvalent icosahedral composition for antigen presentation is disclosed. The composition may comprise an S particle, wherein the S particle may comprise a recombinant fusion protein comprising a norovirus (NoV) S domain protein; a linker protein domain operatively connected to the norovirus S domain protein; and an antigen protein domain operatively connected to the linker.

The composition typically has an icosahedral symmetry structure. In one aspect, the composition comprises 60 sites for antigen presentation.

In one aspect, the norovirus S domain protein is that of a calicivirus. The calicivirus may be characterized by having 180 copies of a single capsid protein.

In one aspect, the norovirus S domain protein may comprise a mutation in a proteinase cleavage site of the NoV S domain protein, wherein the mutation renders the site resistant to trypsin cleavage. One or more mutations may be made to the site, provided the mutation effectively destroys the trypsin cleavage site. Modifications to the site that achieve such effect will be readily understood by one of ordinary skill in the art. In one aspect, the mutation may be at position 69 or position 70. In one aspect, the mutation may occur at position R69. In certain aspects, the mutation may be a change to any amino acid other than K (lysine), which is sufficient to destroy the proteinase cleavage site. In certain aspects, the mutation is R69A. In other aspects, the mutation may occur at position N70, for example, the mutation may be any amino acid other than P (proline) sufficient to destruct the proteinase cleavage site.

In one aspect, the norovirus S domain protein may comprise a mutation sufficient to provide a non-native disulfide bond binding site. The norovirus S domain protein may comprise a mutation of at least two amino acids (that are sterically close to each other) to cysteine residues sufficient to provide at least one non-native disulfide bond binding site, or, in other aspects, at least two non-native disulfide bond binding sites, or at least three non-native disulfide bond binding sites between neighboring S domain proteins of the polyvalent icosahedral S particle. In certain aspects, the mutation may be selected from V57C, Q58C, S136C, M140C, or a combination thereof.

In one aspect, the linker may comprise an amino acid sequence of a length sufficient to provide space and certain flexibility between the S domain protein particle and the displayed antigens. The linker is typically a short peptide of one to ten amino acid units, or three to six amino acids, that connect the C-terminus of the S domain to the displayed antigens. The linker provides space and certain flexibility between the S60 particle and the displayed antigens, which helps the independent folding of the S domain and the displayed antigens. A longer linker may be used as necessary. The amino acid length of the linker should be sufficient to allow flexibility of the protein domains to form the claimed compositions.

The disclosed compositions are ideally suited for presentation of an antigen. Suitable antigens may be readily determined by one of ordinary skill in the art. Exemplary antigens are disclosed herein. In certain aspects, the antigen protein domain may be selected by size, in addition to immunogenicity, and may encode for an antigen having a size of from 8 amino acids up to about 300 amino acids, or from 8 amino acids up to about 400 amino acids, or from 8 amino acids up to about 500 amino acids. As will be readily appreciated by one of ordinary skill in the art, the size of an antigen may vary greatly, and the instant compositions may be used for presentation of a variety of different antigens to illicit an immune response.

In one aspect, the polyvalent icosahedral composition may comprise an antigen protein domain that is a rotavirus (RV) antigen. In one aspect, the antigen protein domain may comprise an RV spike protein antigen (VP8 antigen). In further aspects, the antigen may comprise a TSR antigen of circumsporozoite protein (CSP) of malaria parasite *Plasmodium falciparum*, a receptor-binding domain of the HA1 protein and an M2e epitope of influenza A virus, a P domain antigen of hepatitis E, a surface spike protein of the astrovirus, and combinations thereof. Again, such antigens are merely exemplary and the recitation of such is not intended to limit the scope of the claims. Exemplary sequences include those of SEQ ID NO 34 and SEQ ID NO 35: human Rotavirus VP8 antigen, SEQ ID NO 42 and SEQ ID NO 43: P domain antigen of hepatitis E virus (HEV), SEQ ID NO 44 and SEQ ID NO 45: Surface Spike protein antigens of an avian AstV (see, e.g., (GenBank AC #: NP987088, residue 423-630), SEQ ID NO 46 and SEQ ID NO 47: HA1 antigen (H7) of influenza A virus, SEQ ID NO 48 and SEQ ID NO 49: TSR antigen of the circumsporozoite protein of *Plasmodium falciparum*, and SEQ ID NO 50 and SEQ ID NO 51: M2E epitope of influenza A viruses. It will be understood that antigen sequences used to generate the antigen peptide may have at least 50%, 60%, 70%, 75%, 80%, 85%, 90%, 95%, 96%, 97%, 98%, 99%, or 100% identity to the reference nucleic acid sequence, provided that the resulting antigen elicits at least a partial immune response in an individual administered the composition having the antigen.

The recombinant fusion protein is a subunit of the disclosed vaccine compositions. Further disclosed herein are recombinant fusion proteins that may form the basis of the polyvalent icosahedral compositions. The fusion protein may comprise a norovirus (NoV) S domain protein having a mutation to the trypsin site as described above an added cysteine site as described above; a linker protein domain operatively connected to said norovirus S domain protein having the aforementioned mutations; and an antigen protein domain operatively connected to the linker. The features of each portion of the fusion proteins are described above.

In addition to the S particle described above, the disclosed compositions may further comprise one or more pharmaceutical-acceptable carriers, which may include any and all solvents, dispersion media, coatings, stabilizing agents, diluents, preservatives, antibacterial and antifungal agents, isotonic agents, adsorption delaying agents, and the like. The disclosed S particles may be provided in physiological saline. Optionally, a protectant may be included, for example, an anti-microbiological active agent, such as for example Gentamycin, Merthiolate, and the like. The compositions may further include a stabilizing agent, such as for example saccharides, trehalose, mannitol, saccharose and the like, to increase and/or maintain product shelf-life. Those of skill in the art will understand that the composition herein may incorporate known injectable, physiologically acceptable sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants will be appreciated by one of ordinary skill in the art.

In one aspect, disclosed is a container comprising at least one dose of the immunogenic compositions disclosed herein. The container may comprise 1 to 250 doses of the immunogenic composition, or in other aspects, 1, 10, 25, 50, 100, 150, 200, or 250 doses of the immunogenic composition. In one aspect, each of the containers may comprise more than one dose of the immunogenic composition and may further comprises an anti-microbiological active agent. Those agents may include, for example, antibiotics such as Gentamicin and Merthiolate and the like.

A further aspect relates to a kit. The kit may comprise any of the containers described above and an instruction manual, including the information for the delivery of the immunogenic composition disclosed above. For example, instructions related to intramuscular application of at least one dose may be provided for lessening the severity of clinical symptoms associated with an infection of an antigen as disclosed here. The kits and/or compositions may further include an immune stimulant such as keyhole limpet hemocyanin (KLH), or incomplete Freund's adjuvant (KLH/ICFA). Any other immune stimulant known to a person skilled in the art may also be used.

In one aspect, a method of making the disclosed polyvalent icosahedral structures are disclosed. The method may comprise the steps of a) making a first region comprising a modified NoV S domain protein, wherein said modification comprises a mutation sufficient to destruct an exposed protease cleavage site (wherein the mutation prevents protein degradation), preferably an R69A mutation, and introducing one or more mutations in said norovirus (NoV) S domain protein sufficient to create an inter-S domain protein disulfide bonds, for example, a mutation selected from V57C, Q58C, S136C and M140C, and combinations thereof, and b) recombinantly expressing the first region having a modified NoV S domain protein with a linker and an antigen. In certain aspects, the composition may be effectively produced in *E. coli.*

In one aspect, a method of eliciting an immune response in an individual in need thereof is disclosed. In this aspect, the method may include the step of administering a vaccine composition as disclosed above to an individual in need thereof. It will be readily appreciated that the disclosed compositions may be administered to an individual according to any method known in the art, and that optimal administration (including route and amounts) will not require undue experimentation. The vaccine compositions may be administered prophylactically to an individual suspected of having a future exposure to the antigen incorporated into the vaccine composition. In certain aspects, provided is a method of providing an immune response that protects an individual receiving the composition from infection, or reduces or lessens the severity of the clinical symptoms associated from an infection. The infection may include, for example, malaria, influenza A, hepatitis E, and an astroviral infection. Dosage regimen may be a single dose schedule or a multiple dose schedule (e.g., including booster doses) with a unit dosage form of the composition administered at different times. The term "unit dosage form," as used herein, refers to physically discrete units suitable as unitary dosages for human and animal subjects, each unit containing a predetermined quantity of the antigenic compositions disclosed herein in an amount sufficient to produce the desired effect, which compositions are provided in association with a pharmaceutically acceptable excipient (e.g., pharmaceutically acceptable diluent, carrier or vehicle). The vaccine may be administered in conjunction with other immunoregulatory agents.

Examples

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Generations of novel biomaterials through bioengineering have been a fast-growing field in modern medicine. Typical examples include various polyvalent protein nanoparticles and complexes that have been constructed by taking advantage of the self-formation features of viral capsid proteins [1-3]. Viral capsid proteins are responsible for many basic functions necessary for viral life cycles, particular viral attachment and entry, and thus are able to elicit neutralizing antibodies against viral infection after immunization to humans and animals. This supports the notion that viral capsid proteins are excellent vaccine targets against corresponding viral pathogens. In fact, various capsid protein particles and complexes have been developed and used as non-replicating subunit vaccines to combat against different infectious diseases [1-3] that claim millions of lives each year. Unlike the traditional live-attenuated and inactivated virus vaccines that need cultivation of infectious virions and thus are associated with certain safety concerns, the non-replicating subunit vaccines that derived from bioengineered viral capsid proteins do not involve in an infectious agent, and therefore are safer with lower manufacturing costs than the traditional vaccines. Thus, non-replicating subunit vaccines represent a new generation of innovative vaccine strategy.

Materials and Methods

Plasmid constructs. 1) Expression construct of glutathione-s-transferase (GST)-tagged S domain protein. The S domain with the hinge-encoding sequences of a GII.4 NoV strain VA387 (GenBank AC #: AY038600.3; residue 1 to 221) were inserted into the multiple cloning sites of the pGEX-4T-1 vector (GST Gene Fusion System, GE Healthcare Life Sciences) via the BamH1/Sal I sites. The resulting S domain protein had an N-terminal GST with a thrombin cleavage site in between. 2) Plasmid construct for the Hisx6-fused $S_{R69A}$ domain expression. The same NoV S domain-hinge-encoding sequences with an R69A mutation were inserted into the multiple cloning sites of the pET-24b vector (Novagen) via the BamH1/Not I sites. The resulting S domain protein had a C-terminally fused Hisx6 peptide. 3) DNA construct for $S_{R69A}$-VP8 (SEQ ID NO: 29) chimeric protein expression. A DNA fragment containing RV VP8-encoding sequences of a P[8] human RV strain BM14113, equivalent to the amino acid sequences from 64 to 231 of the VP8 of WA strain (GenBank AC #: VPXRWA), was fused to the C-terminal end of the $S_{R69A}$ domain-hinge with a linker (four histidines) in between. RV strain BM14113 was isolated directly from a RV positive stool sample [45]. A Hisx6-peptide was added to the C-terminus of the VP8 antigen for purification purpose. 4) Expression constructs of the $S_{R69}$s/V57C/M140C-VP8(SEQ ID NO: 31) , the $S_{R69A}$/V57C/Q58C/S136C-VP8(SEQ ID NO: 33) , and SR69/V57C/Q58C/S136C/M140C-VP8 (SEQ ID NO: 37) chimeric proteins. This DNA construct was made by introduction of other two (V57C/M140C), three (V57C/Q58C/S136C), or four (V57C/Q58C/S136C/M140C) mutations to the expression construct of the $S_{R69A}$-VP8 (SEQ ID NO: 29) chimeric proteins through site-directed mutagenesis. 5). Plasmid construct for $S_{R69A}$/V57C/Q58C/S136C-mVP8 (SEQ ID NO: 41) chimeric protein expression. This construct contained the DNA sequences like the $S_{R69A}$/V57C/Q58C/S136C-VP8 (SEQ ID NO: 33) construct, but the VP8-encoding sequences were replaced with those encoding the VP8 of the murine RV EDIM (epizootic diarrhea of infant mice) strain [50]. In addition, DNA constructed for other $S_{R69A}$/V57C/Q58C/S136C-based chimeric particles displaying antigens of various pathogens, including the surface TSR antigen of the circumsporozoite protein (CSP) (GenBank AC #:CAB38998, residues 309-375) of *Plasmodium falciparum* parasite 3D7 strain [51], the M2e epitope of influenza A virus [52, 53], and the P domain antigens of hepatitis E viruses [54-56], were constructed using the construct of $S_{R69A}$/V57C/Q58C/S136C-VP8 (SEQ ID NO: 33) chimeric proteins as the starting construct, in which the RV VP8-encoding sequences are replaced with those encoding the corresponding antigens.

Production and purification of recombinant proteins. The recombinant GST- and Hstx6-fused proteins were expressed in *E. coli* (BL21, DE3) as described previously [11, 47, 53, 56]. The resulting recombinant proteins were purified using Sepharose 4 Fast Flow purification resin (GE Healthcare Life Sciences) for GST tagged and the TALON CellThru Resin (ClonTech) for the Hisx6-peptide fused proteins according to the instructions of the manufacturers. The GST can be removed from the target proteins by thrombin (GE Healthcare Life Sciences) cleavage, while the GST-fusion proteins still bound to the purification resin.

Sodium dodecyl sulfate polyacrylamide gel electrophoresis (SDS-PAGE) and protein quantitation. Purified proteins were analyzed by SDS-PAGE using 10% separating gels. Proteins were quantitated by SDS-PAGE using serially diluted bovine serum albumin (BSA, Bio-Rad) as standards on same gels [46].

Gel filtration chromatography. This was performed to analyze the size distributions of proteins and protein complexes as described previously [11, 53, 57] through an AKTA Fast Performance Liquid Chromatography System (AKTA Pure 25L, GE Healthcare Life Sciences) using a size exclusion column (Superdex 200, 10/300 GL, GE Healthcare Life Sciences). The column was calibrated by gel-filtration calibration kits (GE Healthcare Life Sciences) and purified NoV P particles (~830 kDa) [57], small P particles (~420 kDa) [20], and P dimers (~69 kDa) [1] as described previously [53, 55]. The proteins of the elution peaks were analyzed by SDS-PAGE.

Cesium chloride (CsCl) density gradient ultracentrifugation. 0.5 mL of resin-purified S60-VP8 particles were mixed with 11 mL CsCl solution with a density of 1.300 g/mL and then packed in a 12-ml centrifuge tube. After centrifugation at 288,000 g for 45 h in the Optima L-90K ultracentrifuge (Beckman Coulter) using a SW41Ti rotor, the gradient was fractionated by bottom puncture into 23 fractions with 0.5 mL each. CsCl densities of fractions are determined based on the refractive index. The S60-VP8 particles in factions were analyzed by ELISA, in which individual fractions were diluted 20 folds in PBS and coated on microtiter plates. The coated proteins were detected by NoV VLP- and RV VP8-specific antibodies.

Electron microscopy. Protein samples were prepared for electron microscopy (EM) inspection for particle formation using 1% ammonium molybdate as the staining solution [22]. Specimens were observed under an EM10 C2 microscope (Zeiss, Germany) at 80 kV at a magnification of 10,000× to 40,000×.

Electrospray ionization mass spectrometry (ESI-MS). All ESI-MS measurements were carried out in positive ion mode using a Synapt G2S quadrupole-ion mobility separation-time of flight (Q-IMS-TOF) mass spectrometer (Waters, Manchester, UK) equipped with a nanoflow ESI (nanoESI) source. Each sample solution was prepared in 200 mM aqueous ammonium acetate buffer (pH 6.8, 25° C.) and loaded into a nanoESI tip, which was produced from borosilicate capillaries (1.0 mm o.d., 0.68 mm i.d.) pulled to ~5 μm using a P-1000 micropipette puller (Sutter Instruments, Novato, CA). To perform ESI, a platinum wire was inserted into the nanoESI tip and a voltage of 1.10 kV was applied. A source temperature of 60° C. was used. The Cone, Trap and Transfer voltages were 50 V, 5 V and 2 V, respectively, and the Trap gas flow rate was 6.0 mL·min-1; all other parameters were set at their default values. Data acquisition and processing were performed using Waters MassLynx software (version 4.1).

N-terminal amino acid sequencing. The SDS-PAGE gel slice containing the cleaved S domain protein was cut out and N-terminal amino acid sequencing was conducted by 494 Procise Protein Sequencer/140C Analyzer from Applied Biosystem, Inc. at the Protein Facility of Iowa State University (http://www.protein.iastate.edu/).

Immunization of mice. BALB/c mice (Harlan-Sprague-Dawley, Indianapolis, IN) at 3-4 weeks of age were divided into four groups (N=6) for immunizations with following immunogens (10 μg/mouse): 1) S60-VP8 chimeric particles; 2) free VP8 protein; S60 particle without VP8 antigen; and 4) diluent (phosphate buffered saline, PBS, pH7.4) in the same volume. Immunization was performed intramuscularly three times with Inject Alum adjuvant (Thermo Scientific, 50 μl/mouse) at two-week intervals. Bloods were collected two weeks after the third immunization and sera were prepared from blood samples via a standard protocol.

Enzyme immunoassay (EIA). EIA was performed to measure the antibody titers of mouse sera after immunization with different immunogens, as described previously [46]. Gel-filtration-purified free VP8 antigen at 1 μg/mL was coated on 96-well microtiter plates and incubated with serially diluted mouse sera [47]. Bound antibodies were detected by goat-anti-mouse secondary antibody-HRP conjugates (MP Biomedicals, Inc). Antibody titers were defined by the end-point dilutions with a cutoff signal intensity of OD450=0.1.

HBGA binding assay. Synthetic oligosaccharide- and saliva-based HBGA binding assays were performed to measure the binding function of the S60 particle displayed VP8 to their HBGA ligands [45]. Briefly, synthetic oligosaccharides (2 μg/mL) representing the H1, Leb, and Ley antigens, respectively, or boiled saliva samples (1:1000 diluted) that are H1 and/or Leb positive or H1 and Leb negative were coated on 96-well microtiter plates and incubated with various S60-VP8 particles or S60 particles without RV VP8 at indicated concentrations. The bound proteins were measured by guinea pig anti-VP8 antiserum (for S60-VP8 particles) or guinea pig hyperimmune serum against GII.4 NoV VLPs (for S60 particles), followed by an incubation of HRP-conjugated goat anti-guinea pig IgG (ICN Pharmaceuticals).

Serum blocking titers against RV VP8-HBGA ligand attachment. This was performed as a surrogate neutralization assay as decried previously [47]. Boiled and diluted (1:1000) human saliva samples with positive H1 and Lewis b (Leb) antigens, the ligands of P[8] RV [45, 58], were coated on microtiter plates. The P particle-displayed RV VP8 (PP-VP8) [46] at 625 ng/mL was pre-incubated with the post-immune sera after immunization with various immunogens (S60-VP8 particles, free VP8 antigens, S60 particles, and PBS) at different dilutions before the PP-VP8 was added to the coated saliva samples. The 50% blocking titer (BT50) was defined as the lowest serum dilution causing at least 50% reduction against the binding of PP-VP8 particles to HBGAs/saliva samples compared with the unblocked positive control.

RV neutralization assay: This was performed as described previously [53]. Briefly, MA104 cells were cultivated in 6-well plates and tissue culture-adapted RV Wa strain (GIP [8]) at a titer of ~50 PFU/well was used as the inoculum. Trypsin-treated Wa RVs were incubated with mouse sera after immunization with indicated immunogens (see above) for one hour and then was added to the cells. The plates were overlaid with media including trypsin (Invitrogen) and 0.8% agarose. After a four-day incubation, the plaques were stained and counted. The neutralization (%) of the sera was calculated by the reduction in plaque numbers in the wells treated with antisera relative to the number in untreated control wells.

Structural modeling of the S60 particle. The structures of the S60 particles with or without Hisx6 peptide and the S60-VP8 chimeric particles were modeled using the crystal structure (PDB #: 4PB6) of the 60-valent feline calicivirus (FCV) VLPs [59] as template using software PyMOL Molecular Graphics System, version 1.8.2.0 (Schroinger, LLC). All crystal structure-based images were made by this software.

Structural reconstruction of the S60-VP8 chimeric particles by cryoEM. This was performed using a similar cryo-EM approach described in Applicant's previous studies [20, 21, 46]. Briefly, aliquots (3 to 4 μL) of gel-filtration-purified S60-VP8 chimeric particles were flash frozen onto Quantifoil grids that were then loaded into the microscope. Low-electron (e)-dose images (~20 e/Å2) were recorded on films using a CM200 cryomicroscope at a nominal magnification of ×50,000 and in the defocus range of 2.0 to 4.0 μm. The micrographs were selected and digitized by using a Nikon Super CoolScan 9000ED scanner at step size of 6.35 μm/pixel. The scanned images were binned, resulting in the final sampling of the images at 2.49 Å/pixel. The images of the S60-VP8 chimeric particles were selected using EMAN's boxer program. The selected images were manually filtered to exclude false positives. The EMAN's ctfit program was used to manually determine the contrast-transfer-function (CTF) parameters associated with the set of particle images originating from the same micrograph. Initial models of the particles were created using EMAN's startoct program. Then, the EMAN's refining program was used to iteratively determine the center and orientation of the raw particles and reconstruct the 3-D maps from the 2-D images by the EMAN make3d program until convergence. Icosahedron symmetry was imposed during reconstruction of the S60-VP8 chimeric particles. Analysis of cryo-EM models, including fitting of the S60 particle model (see above) and the crystal structure of P[8] RV VP8 (2DWR) were performed using UCSF Chimera software (version 1.12; http://www.rbvi.ucsf.edu/chimera).

Statistical analysis. Statistical differences among data sets were calculated by software GraphPad Prism 6 (GraphPad Software, Inc) using an unpaired, non-parametric t test. P-values were set at 0.05 ($P<0.05$) for significant difference, 0.01 ($P<0.01$) for highly significant difference, and 0.001 ($P<0.001$) for extremely significant difference.

Ethics statement. This study was carried out in strict accordance with the recommendations in the Guide for the Care and Use of Laboratory Animals (23a) of the National Institutes of Health. The protocols were approved by the Institutional Animal Care and Use Committee (IACUC) of the Cincinnati Children's Hospital Research Foundation (Animal Welfare Assurance no. A3108-01).

Results

Low particle formation efficiency of native NoV S domains. Applicant's study started with production of the native S domain with the hinge of a GII.4 NoV (VA387) in *E. coli* using the expression vector pGEX-4T-1, resulting in GST-S domain fusion proteins with a molecular weight (MW) of ~51 kDa (FIGS. 1, A and B). Free S domain proteins at ~25 kDa (FIG. 1C) without GST was obtained through thrombin cleavage, while the GST remained binding to the sepharose beads. EM observation of the S protein revealed few thin-layer, ring-shaped structures in diameters of ~20 nm (FIG. 1D), most likely equivalent to assembled S particles. To determine the S particle formation efficiency, gel-filtration chromatography of the S domain proteins was performed, revealing two broad peaks (FIG. 1E). SDS PAGE (FIG. 1F) followed by a Western analysis (data not shown) using NoV VLP hyperimmune serum [15] and N-terminally sequencing (FIG. 2, see below), confirmed that both peaks were S proteins. Peak 1 with high MWs larger than 800 kDa should represent the self-assembled S particles or complexes, while peak 2 should be S domain monomers (~25 kDa) and/or dimers (~50 kDa).

Applicant also observed a minor protein band with lower MW that co-occurred with the GST-S fusion proteins (FIG. 1B, 42 kDa) and the free S proteins (FIG. 1C, 16 kDa), respectively, which should be proteinase-cleaved forms of the S proteins as these minor protein bands reacted with the NoV VLP-specific antibody (data not shown) and showed S domain sequences (FIG. 2, see below). Applicant further noted that the S domain proteins that assembled into S particles or complexes were mostly digested into the smaller S domain proteins (FIGS. 1 E and F, peak 1, fraction #15 and #16). By contrast, the unassembled S proteins remained intact (FIGS. 1 E and F, peak 2, fraction #28 and #29), suggesting that the assembled S particles or complexes were sensitive to a proteinase, while the unassembled S proteins were not. The fact that peak 1 represents only a minor portion (<25%) of the total S proteins, Applicant concluded that the native NoV S domain proteins assembled into particles at low efficiency.

Identification of the exposed protease cleavage site in the S protein. The above findings prompted us to identify the protease cleaved site. This was achieved by N-terminally sequencing of the two cleaved S protein bands at ~16 kDa (FIGS. 1, C and F), resulted in the same five-residue sequences of NAPGE (SEQ ID NO: 52) (FIG. 2A). This penta-residues matched the S domain sequences N70 to E74, indicating that the cleavage site is between R69 and N70 (FIG. 2B), which is a trypsin/Clostripaina recognition site. Genetic analysis of NoV VP1 sequences showed that this protease site is highly conserved among all GII NoVs (FIG. 2C). Structural analysis of a GII NoV shell structure (Wen Jiang, unpublished data) indicated that this protease site is exposed on the shell surface (FIG. 2D).

Destruction of the protease site for high S particle formation efficiency. Based on the above data, Applicant introduced an R69A mutation to destruct the proteinase cleavage site, resulting in the $S_{R69A}$ (SEQ ID NO: 27) protein. In addition, Applicant used a C-terminally linked Hisx6 peptide to replace the GST tag to avoid the thrombin cleavage step for a simplified purification procedure (FIG. 3A). Applicant also inserted a short linker (GGGG) (SEQ ID NO: 53) between the hinge and the Hisx6 peptide for flexibility to the Hisx6 peptide to prove the concept of antigen presentation of the S particles.

Figure 3:
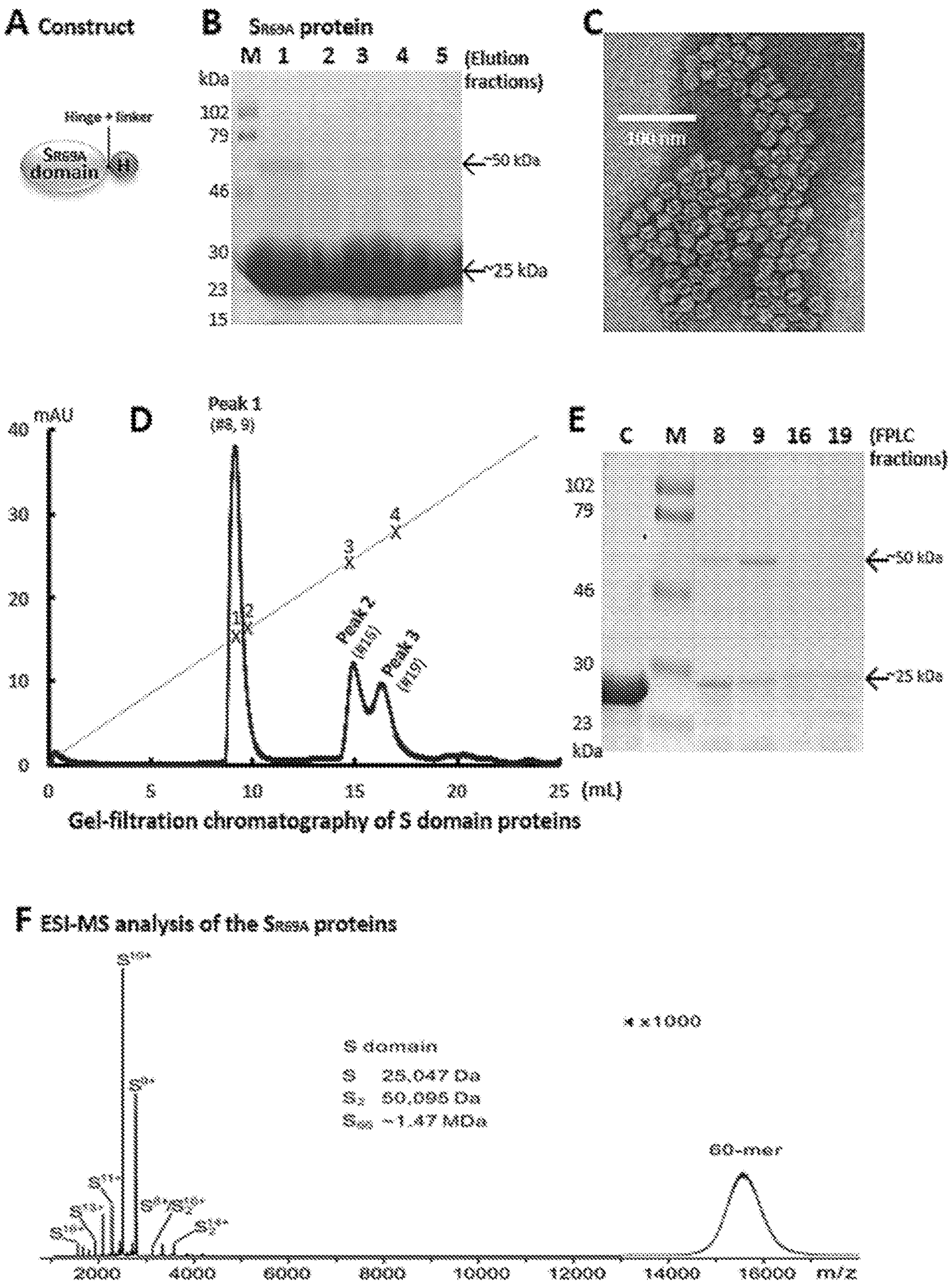
FIG. 3. Production and characterization of the $S_{R69A}$ proteins and the S60 particles. (A) Schematic diagram of the expression construct of the $S_{R69A}$ protein showing the hinge, a linker (GGGG), (SEQ ID NO: 53), and the Hisx6 peptide (an orange ball labeled as H). Its complete sequences are shown in FIG. 2B. (B) SDS-PAGE analysis of the $S_{R69A}$ proteins (~25 kDa). Lanes 1 to 5 were elution fractions from the TALON CellThru Resin. Lane M represents pre-stained protein markers with indicated molecular weights. (C) An EM micrograph of the $S_{R69A}$ (SEQ ID NO: 27) protein showing self-assembled S60 particles in unified sizes. (D and E) Analysis of the $S_{R69A}$ proteins by gel-filtration chromatography (D), followed by an SDS PAGE analysis of the elution peaks (E). (D) Elution curve of gel-filtration chromatography of the $S_{R69A}$ proteins via a size-exclusion column (Superdex 200, 10/300 GL). The gel-filtration column was calibrated as done in FIG. 1E. The elution positions of the blue Dextran 2000 (~2000 kDa), P particle (~830 kDa), P dimer (~69 kDa), and aprotinin (~6.5 kDa) are indicated by (x) and 1, 2, 3, and 4, respectively. (E) SDS-PAGE analysis of the $S_{R69A}$ proteins of the three majorpeaks in the gel-filtration (D), in which lane C is the control $S_{R69A}$ proteins before being loaded to the size-exclusion column; lane M is the pre-stained protein markers with indicated molecular weights; lanes 8 and 9 were from fractions #8 and 9 of peak 1, lane 16 was from fraction #16 of peak 2; while lane 19 was from fraction #19 of peak 3. (F) Electrospray ionization mass spectrometry (ESI-MS) analysis of the $S_{R69A}$ proteins. ESI-MS acquired in positive ion mode for aqueous ammonium acetate solutions (200 mM, pH 6.8 and 25° C.) of 80 μM $S_{R69A}$ protein (SEQ ID NO: 27) (based on monomers). Both the $S_{R69A}$ domain monomers (25.047 kDa) and dimers (50.095 kDa) were detected. A broad feature centered at m/z ~15,500 was observed. Although the mass resolution was insufficient to establish the charge states, the MW of these ions is estimated based on reported m/z of large protein complexes [61] to be approximately 1.47 MDa, corresponding to the MWs of the 60 valent S60 particles.

The $S_{R69A}$ (SEQ ID NO: 27) protein (~25 kDa) was produced well in the *E. coli* system and could be purified by the Hisx6-binding TALON CellThru Resin at extremely high yield (>40 mg/liter bacterial culture) and high stability (FIG. 3B). EM observation indicated many ring-shapes structures in unified size, representing the self-assembled S particles in diameters of ~22 nm (FIG. 3C). Gel-filtration revealed one major and two minor peaks (FIGS. 3, D and E) that should represent the S particles (>1 mDa), S dimers (~50 kDa), and S monomers (~25 kDa), respectively, based on their MWs, which were supported by EM observations and ESI-MS analysis (below). SDS-PAGE often revealed minor bands at ~50 kDa (FIGS. 3, B and E) that reacted with NoV VLP-specific antibody (data not shown), indicating that they were the S domain dimers that were not completely denatured in the SDS-PAGE analysis. This was particularly obvious in the S particles factions (peak 1: fractions #8 and #9) of the gel-filtration chromatography (FIGS. 3, D and E) compared with the dimer (peak 2: #16) and monomer (peak 3: #19) fractions. These data indicated that vast majority of the $S_{R69A}$ (SEQ ID NO: 27) protein assembled into unified S particles.

Figure 7:
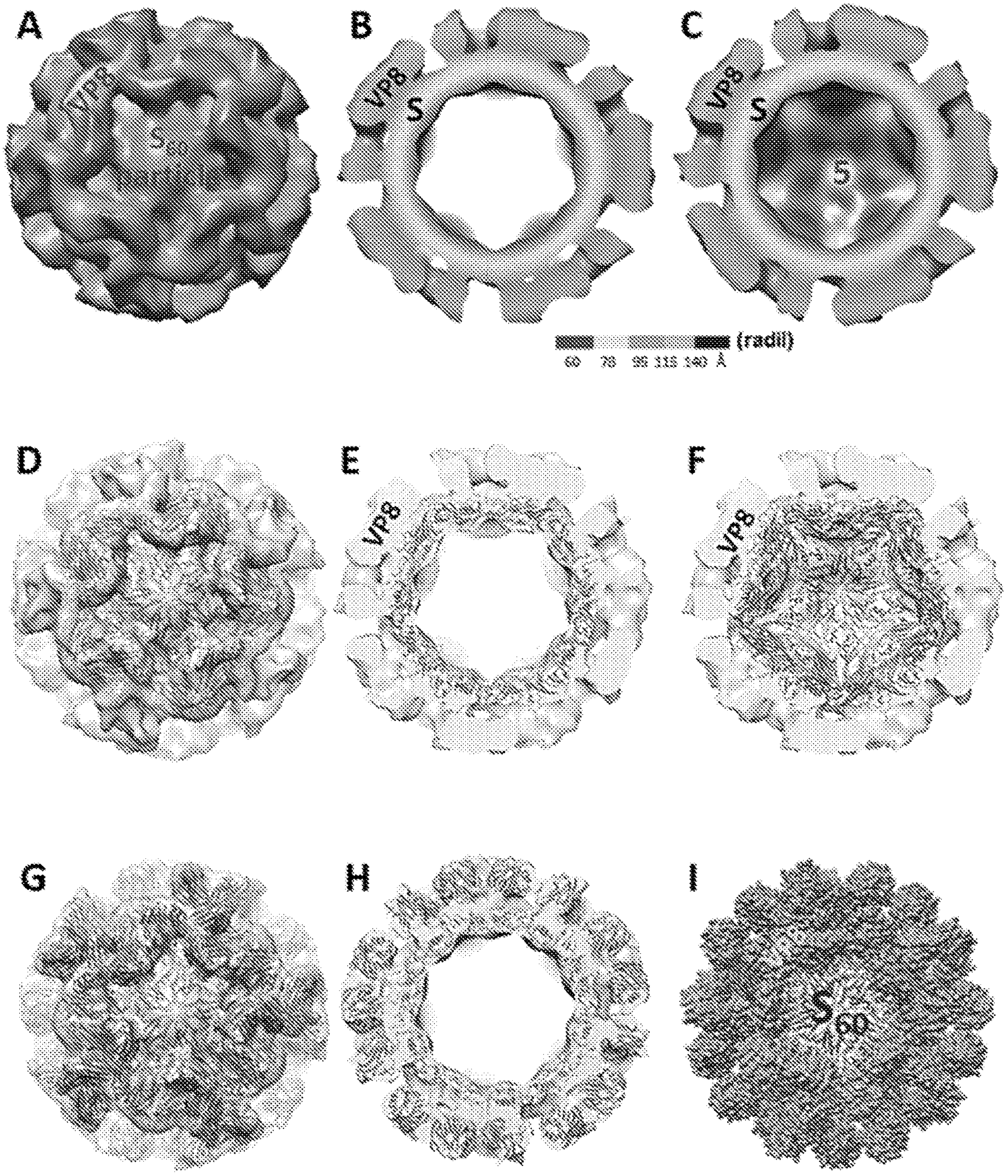
FIG. 7. Structure of the S60-VP8 particle. (A to C) The three-dimensional structures of the S60-VP8 particles were reconstructed by cryoEM technology. (A) Surface structure of the S60-VP8 particle at the five-fold axis. (B and C) The slice structures of the middle slice (B) and the second half (C) of the S60-VP8 particle showing the external and internal structures. The interior S60 particle (S) and the protruding VP8 antigens are indicated. The color schemes based radii are shown. "5" indicates the five-fold axis. (D to F) Fitting of the 60 valent FCV shell structure (red, cartoon representation) into the cryoEM density map (transparent grey) of the S60-VP8 particle. The fittings results are shown by three transparent slice views, showing the first half (D), the middle slice (E), and the second half (F) of the S60-VP8 particle viewing from the front. (G and H) Fitting of 60 copies of the VP8 crystal structure (PDB code: 2DWR) of a P[8] RV into the protruding regions of the S60-VP8 particle cryoEM density maps. The fitted FCV shell crystal structures in the S60 particle region of the S60-VP8 particle are shown in cartoon representation (red), while the fitted VP8 crystal structures in the protruding regions are shown in blue cartoon representation. (I) An S60-VP8 particle model based on the above fitting outcomes. The interior S60 particle is shown in red cartoon representation, while 60 protruding VP8 antigens are indicated in dot representation in light blue color.
Figure 8:
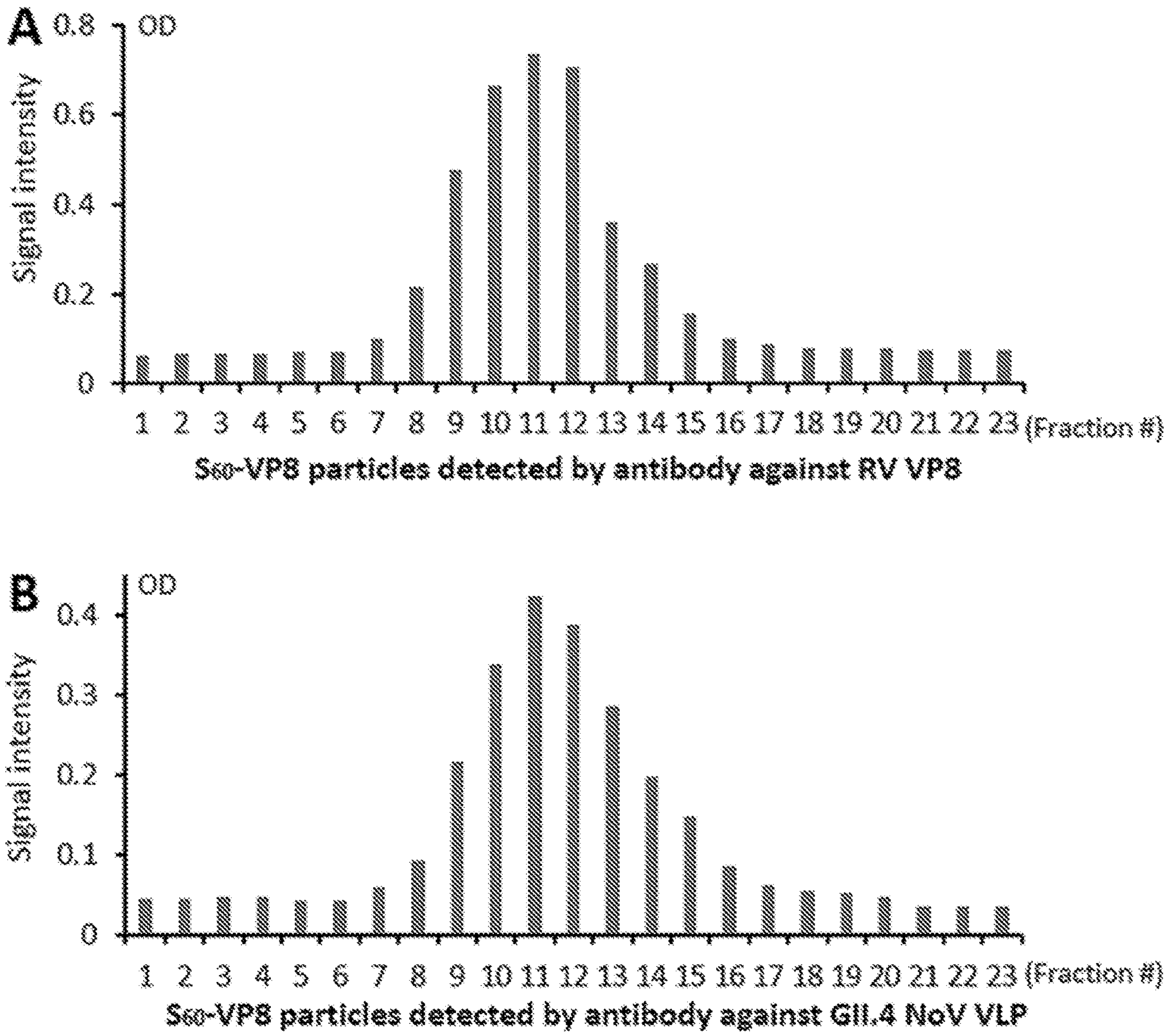
FIG. 8. The S60-VP8 particles formed a peak after CsCl density gradient centrifugation. The S60-VP8 particles was loaded on a CsCl density gradient. After ultracentrifugation the S60-VP8 particles in the fractionated gradient were detected by antibodies specific to P[8] RV VP8 (A) and GII.4 NoV VLPs (B), respectively. In both cases, a defined peak of the S60-VP8 particles was detected at the middle of the gradient.
Figure 9:
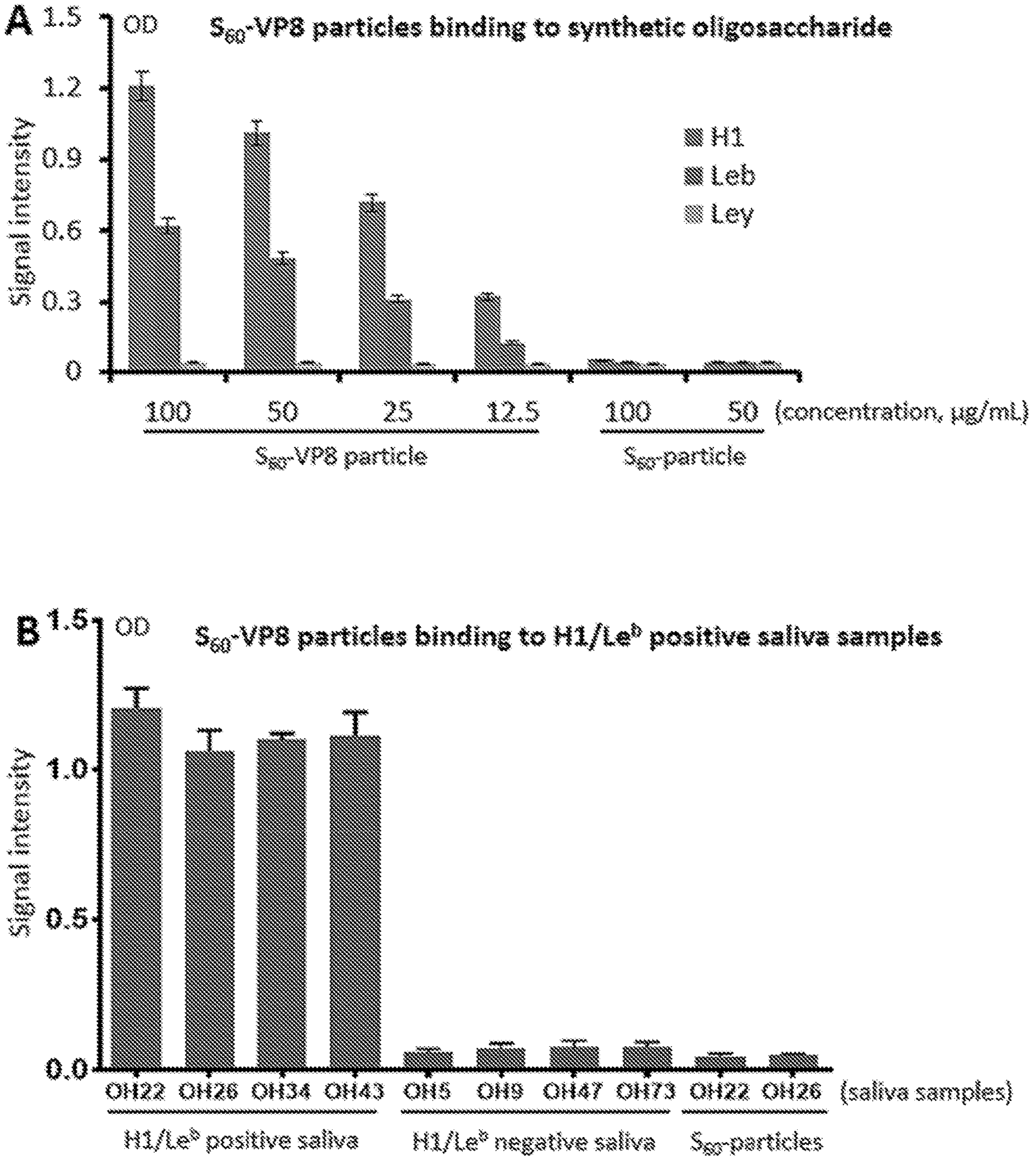
FIG. 9. The S60 particle-displayed VP8s retain ligand-binding function. (A) Glycan binding assays showed that the S60-VP8 particles bound synthetic oligosaccharides representing the H1 and Leb antigens, but not that representing the Ley antigens. The S60 particles without VP8 did not bind any of the three antigens.

Self-assembly of the SR68A (SEQ ID NO: 27) protein into 60-valent S60 particles. Applicant then performed ESI-MS analysis to determine the complexity of the $S_{R69A}$ (SEQ ID NO: 27) proteins, revealing three protein forms: 1) S monomers at 25.047 kDa, 2) S dimers at 50.095 kDa, and 3) S particles at ~1.47 mDa (FIG. 3F). Since the calculated MW of the recombinant S domain protein is 24585.89 Daltons (FIG. 2B), the observed self-assembled S particles should be 60-valent accordingly, designated as S60 particles. The fact that no signals larger than ~1.47 mDa were observed indicated that the traditional 180-valent S particle did not assemble, consistent with the unified particle size observed by EM (FIG. 3C). These 60-valent S60 particles were further confirmed by structural reconstruction of the S60-VP8 chimeric particle by cryoEM technology (FIG. 7, see below).

Figure 4:
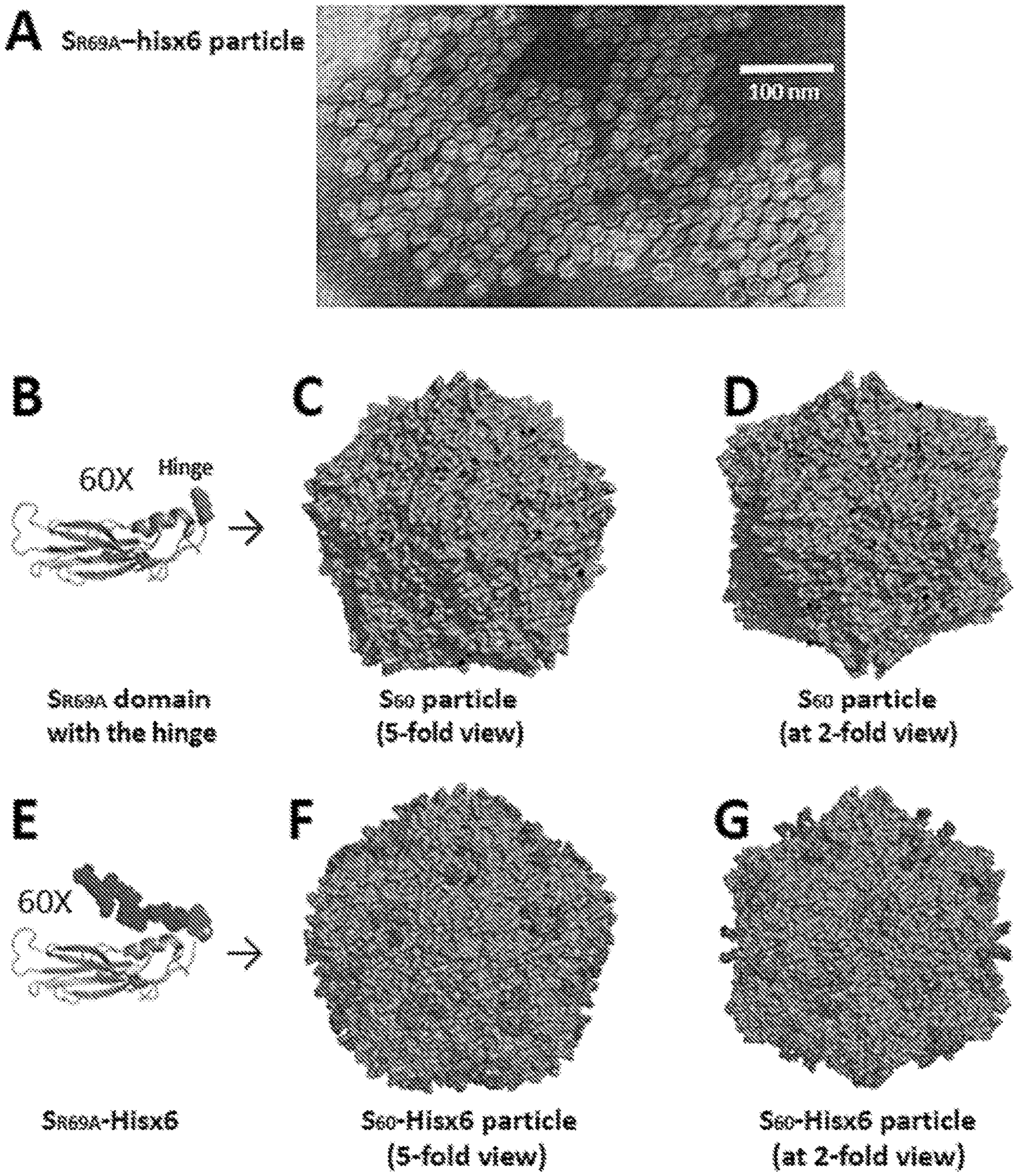
FIG. 4. Structural modeling of the S60 particles based on the known crystal structure (PDB #: 4PB6) of the 60-valent feline calicivirus VLPs. (A) An EM micrograph showing the S60 particles. (B to D) The structures of the $SR_{69A}$ (SEQ ID NO: 27) protein monomer (orange) in cartoon representation (B) and the S60 particles at five- (C) and two-fold (D) axis, respectively, in surface representation. The exposed C-terminal hinges (surface representation) are shown in green. (E to G) The structures of the $S_{R69A}$ (SEQ ID NO: 27) protein monomer (orange) in cartoon representation with a C-terminally fused linker (magenta) and a Hisx6 peptide (skyblue) in dot representation (E) and the resulting S60 particles at five- (F) and two-fold (G) axis, respectively, in surface representation. The exposed C-terminal hinges, linkers, and Hisx6 peptides are shown in dot representations.

Structural modeling of the S60 particle. While detailed structure of a 60-valent NoV capsid or its interior shell remains unknown, the crystal structure of the 60-valent feline calicivirus (FCV) VLP has been reported [59], providing a way to model the S60 particles to understand their structure features. The structure model of the S60 particle was built by using the crystal structure of the 60-valent FCV VLP (PDB #: 4PB6) as a template (FIG. 4, B to D). The modeled S60 particles exhibited somewhat pentagonal (FIG. 4C) and hexagonal (FIG. 4D) shapes at five- or two-fold axis, respectively. These pentagonal and hexagonal shapes can be easily recognized among the S60 particles in the EM micrographs (FIG. 4A and FIG. 3C). In addition, the S60 particle models can be fitted well into the S60 particle region of the cryoEM density map of the S60-VP8 particle (FIG. 7, D to F), supporting the structural similarity between the 60-valent FCV shell and the NoV S60 particle. As expected, 60 C-terminal hinges are exposed on the surface of each S60 particles (FIG. 4, B to D), providing excellent fusion points to foreign antigens to be displayed by the S60 particle.

Applicant also modeled the S60 particle with C-terminal linkers (GGGG) (SEQ ID NO: 53) and Hisx6 peptides to mimic antigen presentation by the S60 particle (FIG. 4, E to G). The resulting models indicated that 60 Hisx6 peptides were displayed on the surface of each S60 particle, supporting the fact the S60 particles with the C-terminal linked Hisx6 peptides were purified efficiently by the Hisx6-binding resin (FIG. 3B). Therefore, it is plausible to anticipate that various antigens from other pathogens can also be displayed by the S60 particles through fusing them to the exposed C-terminus of the S protein.

Figure 5:
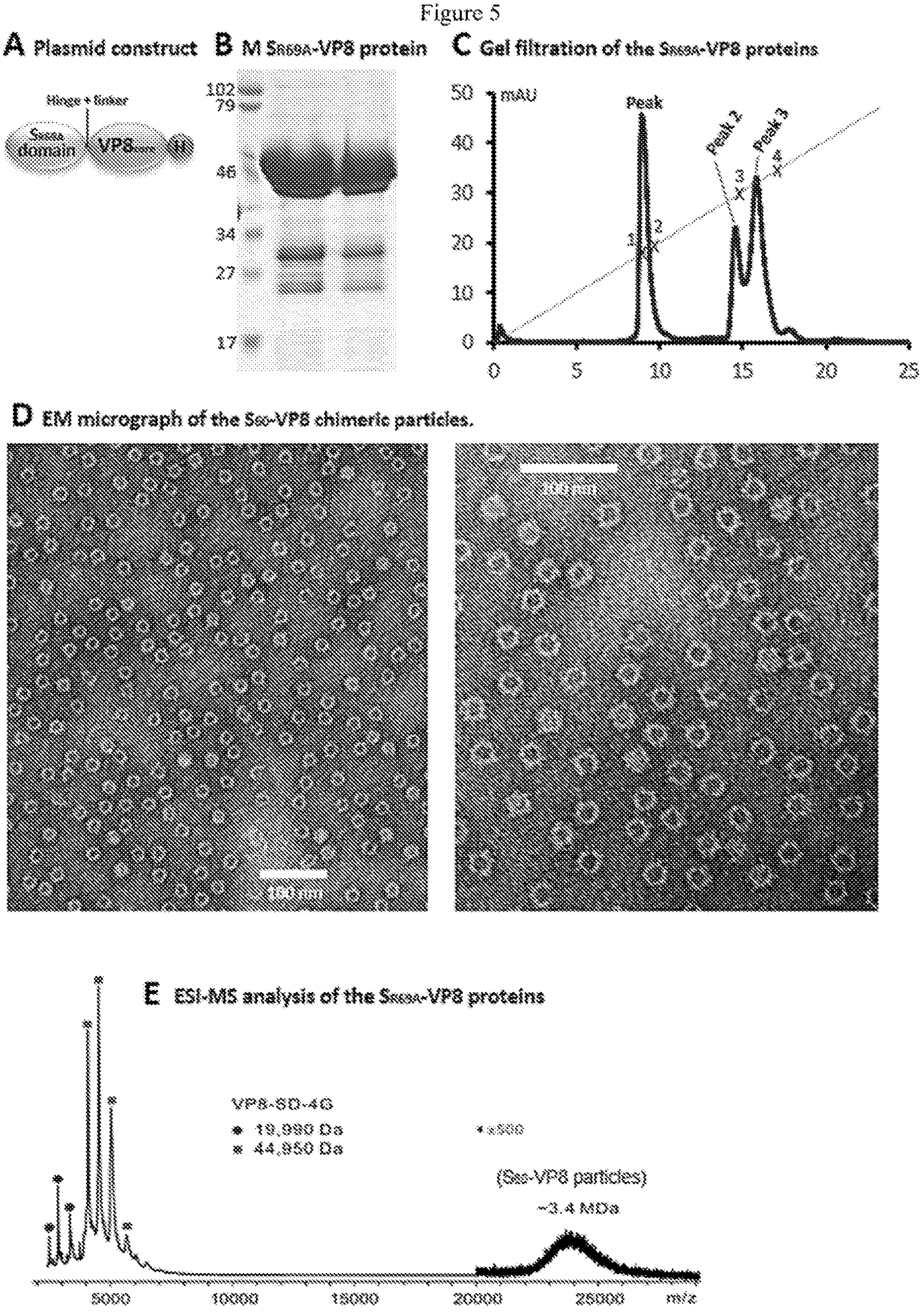
FIG. 5. Characterization of the S60-VP8 chimeric particles. (A) Schematic diagram of the $S_{R69A}$-VP8 (SEQ ID NO: 29) chimeric protein. The VP8 antigen (green) of rotavirus was fused to the hinge via a linker (HHHH) (SEQ ID NO: 54) . A Hisx6 peptide (orange) was fused to the C-terminus of the VP8 antigen. (B) SDS-PAGE analysis of the $S_{R69A}$-VP8 (SEQ ID NO: 29) protein (~45 kDa). (C) Gel-filtration chromatography of the $S_{R69A}$-VP8 (SEQ ID NO: 29) protein through the size-exclusion column (Superdex 200, 10/300 GL). The column was calibrated as done in FIG. 1E. The elution positions of the blue Dextran 2000 (~2000 kDa), P particle (~830 kDa), P dimer (~69 kDa), and aprotinin (~6.5 kDa) are indicated by (x) labeled as 1, 2, 3, and 4, respectively. (D) EM micrographs of the S60-VP8 particles from peak 1 of the gel-filtration (C). (E) Electrospray ionization mass spectrometry (ESI-MS) analysis of the $S_{R69A}$-VP8 proteins. ESI-MS acquired in positive ion mode for aqueous ammonium acetate solutions (200 mM, pH 6.8 and 25° C.) of 80 µM $S_{R69A}$-VP8 (SEQ ID NO: 29) protein (based on monomers). The $S_{R69A}$-VP8 monomers (44.950 kDa) and a degraded product (19.990 kDa) were detected. A broad feature centered at m/z ~23,700 was observed. Although the mass resolution was insufficient to establish the charge states, the MW of these ions is estimated based on reported m/z of large protein complexes [61] to be approximately 3.4 MDa, corresponding to the MWs of the 60 valent $S_{R69A}$-VP8 particles.

Production and characterization of S60-VP8 chimeric particles. To prove the feasibility of the S60 particle as a platform for antigen presentation for enhanced immunogenicity, Applicant produced S60-VP8 chimeric particles that display RV VP8 proteins, the major RV neutralizing antigens. This was achieved by fusion of the RV VP8 protein to the C-terminus of the $S_{R69A}$ (SEQ ID NO: 27) protein via a linker (FIG. 5A). A Hisx6 peptide was added to the C-terminus of the VP8 protein for purification purpose. The $S_{R69A}$-VP8 (SEQ ID NO: 29) chimeric protein (~45 kDa) was expressed well in the *E. coli* system at high yields of >30 mg/liter bacterial culture (FIG. 5B). Gel-filtration analysis of the $SR_{69A}$-VP8 proteins revealed three typical peaks, most likely representing the $S_{R69A}$-VP8 particles (peak 1), dimers (peak 2), and monomer (peak 3), respectively, based on their MWs (FIG. 5C). Retention comparison of the three peaks indicated that about a half of the SRMA-VP8 proteins self-assembled into particles (peak 1 vs. peak 2 and peak 3).

EM observation of the proteins from peak 1 revealed many $S_{R69A}$-VP8 particles (referred as S60-VP8 particles) in unified size with recognizable protrusions due to the surface displayed VP8 proteins, leading to rough surfaces (FIG. 5D), which differed from the relative smooth surface of S60 particles (FIGS. 3C, and 4A). ESI-MS analysis of the peak 1 proteins revealed anticipated 60-valent S60-VP8 particles with MWs of ~3.4 mDa (FIG. 5E). Again, no signal of 180-valent particles was observed, consistent with the unified size of the S60-VP8 particles on the micrographs of the same proteins (FIG. 5D). However, the ESI-MS analysis did reveal monomers (44.950 kDa) of the $S_{R69A}$-VP8 (SEQ ID NO: 29) protein and trace amount of degraded product at 19.990 kDa, indicating that the S60-VP8 particles could disassembled into monomers.

Further stabilization of the S60-VP8 particles. The relatively low particle formation efficiency by the $S_{R69A}$-VP8 proteins indicated room for improvement by increasing inter-molecular interaction between neighbor S domains in the S particles. Inspection of a GII.4 shell structure (W.J., unpublished data) indicated that V57 and Q58 of an S domain are sterically close to M140 and S136 of the neighboring S domain, respectively, with distances of 5.7 to 5.9 Å (FIGS. 6. A and B). This suggested that the two pair residues are good locations to introduce inter-S domain disulfide bonds to further enhanced the S60-VP8 particle formation.

When V57 and M140 of the $S_{R69A}$-VP8 (SEQ ID NO: 29) protein were mutated into cysteines (FIG. 6C), the $S_{69A/58C/140C}$-VP8 proteins were expressed well at extremely high yields of >50 mg/liter bacterial culture (FIG. 6D). Gel-filtration analysis indicated that majority (~70%) of the proteins assembled into the S60-VP8 particles (FIG. 6E) that was confirmed by EM observations (data not shown). It was noted that peak 3 representing the S monomers was completely gone, supporting the increase of inter-S domain interaction after the disulfide bond introduction.

Figure 6:
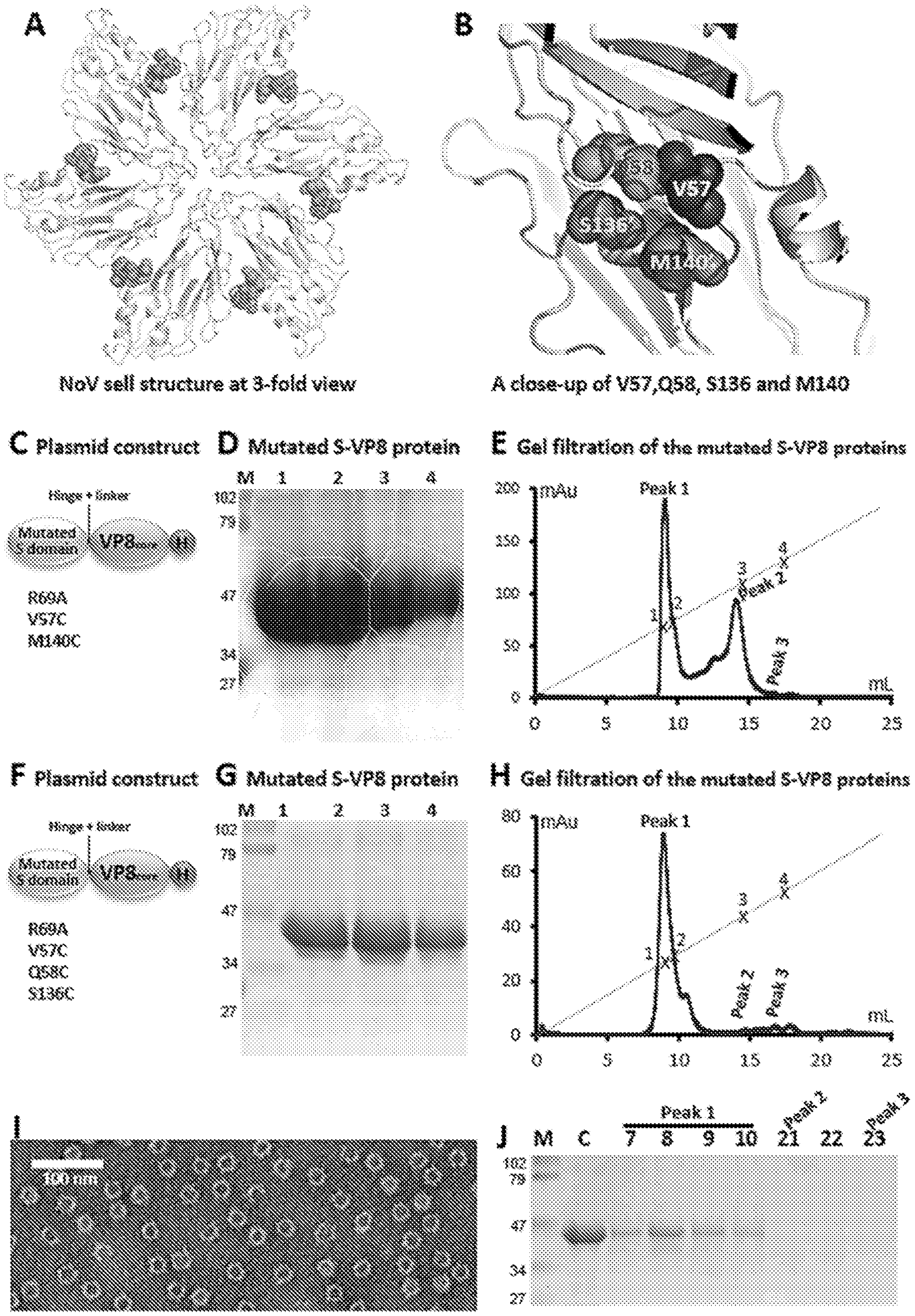
FIG. 6. Further stabilization of the S60-VP8 particles by introducing inter-S domain disulfide bonds. (A and B) Structural analysis of a GII. 4 shell structure. (A) Partial shell structure of a GII.4 NoV (W.J., unpublished data) at three-fold axis revealed that V57 and Q58 of an S domain are sterically close to M140' and S136' of the neighboring S domain, respectively. The six S domain are shown in cartoon representation in grey, while the mentioned four amino acids are shown in sphere representation in different colors. (B) A close-up of the steric relationship among V57 (red)/Q58 (cyan) of one S domain and S136' (green)/M140' (orange) of the neighboring S domain with distances of 5.7 to 5.9 Å. (C to E) Characterization of the $S_{R69A}$/V57C/M140C-VP8 proteins. (Protein Sequence shown in SEQ ID NO 31.) (C) The expression construct of the $S_{R69A}$/V57C/M140C-VP8 (SEQ ID NO: 31) protein. (D) SDS PAGE analysis of the $S_{R69A}$/V57C/M140C-VP8 (SEQ ID NO: 31) protein. Lanes 1, 2, 3, and 4 are four eluted protein fractions from the affinity column. 15 µl of each fraction were loaded in each lane. M, prestained protein markers. (E) The elution curve of a gel-filtration chromatography of the $S_{R69A}$/V57C/M140C-VP8 proteins through the size-exclusion column (Superdex 200, 10/300 GL). The gel-filtration column was calibrated as done in FIG. 1E. The elution positions of the blue Dextran 2000 (~2000 kDa), P particle (~830 kDa), P dimer (~69 kDa), and aprotinin (~6.5 kDa) are indicated by (x) labeled as 1, 2, 3, and 4, respectively. (F to J) Characterization of the $S_{R69A}$/V57C/Q58C/S136C-VP8 proteins. (Protein sequence shown in SEQ ID NO 32) (F) The expression construct of the $S_{R69A}$/V57C/Q58C/S136C-VP8 (SEQ ID NO: 32) protein. (G) SDS PAGE analysis of the $S_{R69A}$/V57C/Q58C/S136C-VP8 (SEQ ID NO: 32) proteins. Lanes 1, 2, and 3 are three eluted protein fractions from the affinity column. 10 µl of each fraction were loaded ro each lane. (H) Gel-filtration analysis of the $S_{R69A}$/V57C/Q58C/S136C-VP8 (SEQ ID NO: 32) proteins through the size-exclusion column (Superdex 200, 10/300 GL). The gel-filtration column was calibrated as done in FIG. 1E. The elution positions of four proteins with different MWs are indicated as (E). (I) EM micrograph of the S60-VP8 particles from peak 1 of the gel filtration (H). (J) SDS PAGE analysis of the proteins from peak 1 (fraction #7 to 10), peak 2 (faction #21), and peak 3 (fraction #23). Lane C is control protein before loading to the column.

When V57, Q58, and S136 of the $S_{R69A}$-VP8 (SEQ ID NO: 29) protein were mutated into cysteines (FIG. 6F), the $S_{69A57C/58C/136C}$-VP8 proteins can be produced at high yield to >40 mg/liter bacterial culture (FIG. 6G). Gel-filtration analysis (FIGS. 6, H and J) demonstrated that vast majority (>90%) of the $S_{69A/57C/136C}$-VP8 proteins self-assembled into the S60-VP8 particles that was confirmed by EM observations (FIG. 6I). Remarkably, both peaks 2 and 3 representing the S dimer and monomers, respectively, disappeared (FIGS. 6, H and J), supporting the notion that the S60-VP8 particles formation efficiency increased dramatically, as a result of inter-S domain disulfide bonds. Applicant also performed quadruple cysteine mutations to all four V57, Q58, S136, and M140 of the $S_{R69A}$-VP8 (SEQ ID NO: 29) protein, the outcomes in protein yields and S60-VP8 particle formation efficiency were similar to those of $S_{69A/57C/136C}$-VP8 proteins (data not shown), indicating that triple cysteine mutation was good enough to produce highly stable S60-VP8 particles.

Structures of the S60-VP8 particles. Applicant constructed the three-dimensional (3-D) structure of the S60-

VP8 particle by cryo-EM technology (see materials and methods) to a resolution of 14 Å, exhibit a T=1 symmetry containing 60 S-VP8 proteins (FIG. 7). The surface structure of the S60-VP8 particle (FIG. 7A) indicated that the VP8 antigens were displayed on the surface of the S60-VP8 particle, forming the protrusions extending from the interior S60 particle. The slice structures of the middle slice (FIG. 7B) and the second half (FIG. 7C) of the S60-VP8 particle showed the structures of the exterior VP8 antigens (cyan and partial green) and the interior S60 particle (red, yellow and partial green). The five-fold axis of the icosahedral S60 particle can be recognized (FIG. 7C). The diameter of the S60-VP8 chimeric particle is ~28 nm.

When the crystal structure of the 60-valent FCV shell (PDB #: 4PB6) was fitted into the S60-particle portion of the S60-VP8 particle cryoEM density map, both structures fitted very well each other (FIG. 7, D to F). Transparent cryoEM density maps with the fitted FCV shell structure of the first half (FIG. 7D), the middle slice (FIG. 7E), and the second half (FIG. 7F) of the S60-VP8 particle demonstrated an excellent fitness between the FCV 60-valent shell structure and the NoV S60 particle region of the S60-VP8 particle, confirming the 60-valent icosahedral structure of Applicant's S60 particle (FIG. 4) and the S60-VP8 particles.

Applicant then fitted 60 copies of the VP8 crystal structure (PDB code: 2DWR) of the P[8] RV Wa strain into the protruding regions of the S60-VP8 particle cryoEM density maps (FIGS. 7, G and H). Transparent cryoEM density maps of the first half (FIG. 7G) and the middle slice (FIG. 7H) of the S60-VP8 particle with the fitted VP8 crystal structures indicated excellent fitness between the protruding regions of the S60-VP8 particle and the 60 VP8 structures, further confirming the structures and orientations of the VP8 antigens on the surface of the S60 particle. Based on the fitting outcomes, Applicant made a S60-VP8 particle model using the crystal structures of the 60-valent FCV shell and 60 VP8s of P[8] RV (FIG. 7I).

The S60 particle displayed VP8s retain ligand-binding function. Applicant's previous study showed that VP8 of P[8] RV bound H1 antigens, but not Ley antigen [45]. Saliva-based binding assay indicated that S60-VP8 particles bound the H1 and/or Leb antigen-positive saliva samples, but not those that were negative for H1 and Leb antigens. These data indicated that the S60 particle-displayed VP8 antigens are in correct folding with ligand-binding function, validating the S60-VP8 particle as a RV vaccine candidate.

Figure 10:
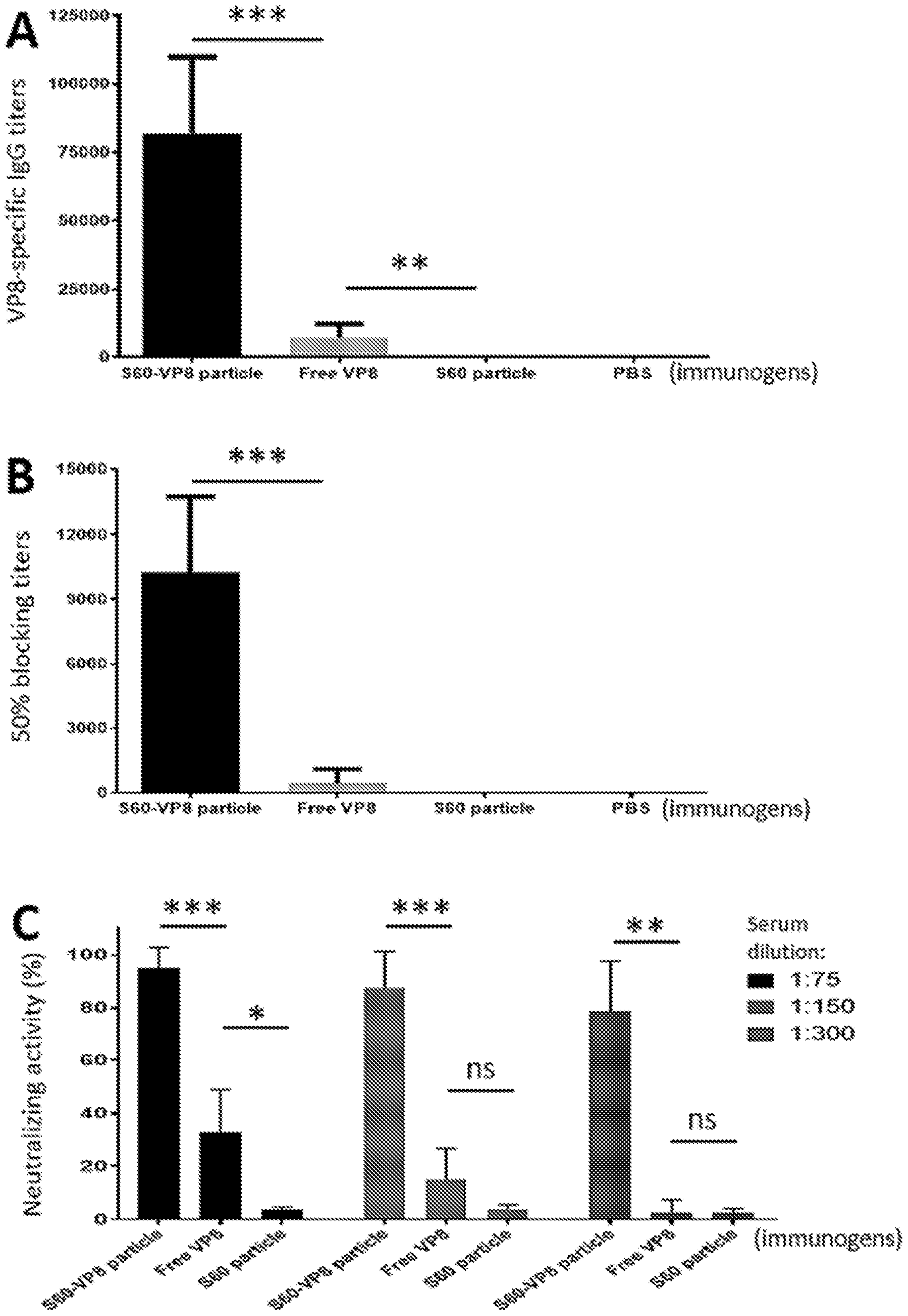
FIG. 10. The S60-VP8 particle enhanced immunogenicity toward the displayed RV VP8 antigen. Same dose/dosage of the S60-VP8 particles, free VP8 antigens, and S60 particles without VP8 were immunized to mice (N=6), respectively, followed by measurements of the VP8-specific IgG responses (A), as well as 50% blocking titer (BT50) against RV VP8-ligand interaction (B) and neutralization activity against RV infection (C) of the resulting mouse sera. (A) VP8-specific IgG response elicited by the S60-VP8 particle, free VP8 antigens, and the S60 particles, respectively. (B)

Improved immunogenicity toward the S60 particle-displayed VP8 antigens. The S60-VP8 particles were immunized to mice (N=6) and measured the VP8-specific immune responses using the free VP8 antigen as control for comparison. After three immunizations, the VP8-specific IgG response after immunization with the S60-VP8 particles was 11.6 folds higher than that induced by the free VP8 (P=0.0004) (FIG. 10A). As negative controls the S60 particles did not elicit any VP8-specific IgG response. These data indicated that the S60 particle is able to improve the immunogenicity of the displayed RV VP8 antigens.

The S60-VP8 particle-elicited antisera enhanced blockade against VP8-ligand binding. Binding of VP8s to RV host ligands or receptors is a key step in RV infection [43]. Accordingly, an in vitro blocking assay against the binding of RV VP8 proteins to HBGAs has been developed as a surrogate RV neutralization assay [47]. Applicant performed such blocking assays using the previously developed P-VP8 particles [47] and Leb-positive saliva samples as the RV ligands [45]. Applicant found that the mouse antisera after immunization with the S60-VP8 particles exhibited 22.8 folds higher 50% blocking titer (BT50) than that of the antisera after immunization with the free VP8 antigens (P=0.0003) (FIG. 10B), further supporting the notion that the S60 particle significantly improved the immunogenicity of the displayed RV VP8 antigens. As negative control, mouse sera after immunization with the S60 particles without VP8 antigens did not reveal such blockades.

The S60-VP8 particle-elicited antisera enhanced neutralization against RV infection. Applicant also performed conventional cell culture-based neutralization assays to determine the neutralizing activity of the S60-VP8 particle-elicited antisera against infection of the cell-culture adapted (P[8]) RV Wa strain. In consistence with their BT50s (see above), the mouse antisera after immunization with the S60-VP8 particles exhibited significantly higher neutralizing activities at three different serum dilutions (1:75, 1:150, and 1:300) than those of the antisera after immunization with the free VP8 antigens (P=0.0003, P=0.0001, and P=0.0016, respectively) (FIG. 10C). The mouse antisera after immunization with the S60 particles without VP8 did not revealed such neutralization activity. These data further supported the notions that the S60 particles is a capable vaccine platform for increased immunogenicity of the displayed RV VP8 antigens and that the S60-VP8 particle is a promising vaccine candidate against RV infection.

The S60 particle as a multifunction vaccine platform. In addition to the RV VP8 antigen, Applicant have been able to fuse several other epitopes and antigens to the S60 particle through the same exposed S domain C-terminus via a linker, including the M2e epitope of influenza A virus, the TSR antigen of the circumsporozoite surface protein (CSP) of malaria parasite *Plasmodium falciparum*, and the P domain of hepatitis E virus (Table 1). Thus, the artificially developed S60 particle serves as a multifunction platform for novel vaccine development.

TABLE 1

A list of epitopes and antigens displayed by the $S_{60}$ particles.

| Epitope/Antigen | Size (residue) | Yield (mg/liter bacteria culture) | $S_{60}$-antigen particle formation |
|---|---|---|---|
| M2e epitope[1] | 23 | 5 | yes |
| TSR/CSP antigen[2] | 67 | 10 | yes |
| Full RV VP8[3] | 231 | 20 | yes |
| Murine RV VP8[3] | 159 | 5 | yes |
| HEV P domain[4] | 187 | 10 | yes |

[1]M2e epitope is the ectodomain of Matrix-2 (M2) protein forming the proton-selective ion channel of an influenza A virus.
[2]TSR/CSP antigen is the C-terminal antigen of the major surface protein of a circumsporozoite (CSP) that play a key role in host cell invasion of a malaria parasite *plasmodium falciparum*.
[3]Full RV VP8 is the full-length VP8 domain of the spike protein of a human P[8] rotavirus.
[3]Murine RV VP8 is the core portion of the spike protein of a murine rotavirus.
[4]HEV P domain is the protruding domain of a hepatitis E virus capsid.

Discussion

In this study Applicant have developed a new technology to produce unified 60-valent NoV S60 particles in a high efficiency via the simple bacterial expression system. This was achieved by taking advantage of the homotypic interactions of NoV VP1 S domain that naturally builds the interior shells of NoV capsids, as well as several modifications to stabilize the S domain proteins and enhance the inter-S domain interactions. Specifically, Applicant introduced an R69A mutation to destruct the exposed protease cleavage site on the native shells that otherwise leads to easy degradation of the S proteins. In addition, Applicant introduced triple (V57C/Q58C/S136'C) or quadruple (V57C/

Q58C/S136'C/M140'C) cysteine mutations to two pairs of sterically close residues (V57/M140' and Q58/S136', FIG. 6) between two neighboring S domains to establish inter-S domain disulfide bonds for stronger inter-S domain interactions than what they exhibit in the native NoV shell. Ultimately, the bioengineered S domains are easily produced by the simple *E. coli* system at high yields, resulting in self-formation the S60 particle at a high efficiency.

The self-assembled, polyvalent S60 particle with 60 flexibly exposed S domain C-termini is an ideal platform of antigen presentation for improved immunogenicity toward the displayed antigens for vaccine development. This idea has been largely proven in this study by constructing a chimeric S60 particles displaying 60 RV VP8 proteins, the major RV neutralizing antigens. The S60-VP8 particles can be easily produced with high stability. They elicited significantly higher IgG response in mice toward the displayed VP8 antigen than that induced by the free VP8 proteins. The mouse antisera after vaccination with the S60-VP8 particles exhibited significantly stronger blockade against RV VP8 binding to its glycan ligands and significantly higher neutralizing activities against RV infection and replication in culture cells than those of sera after immunization with the free VP8 antigens. While protective efficacy of the S60-VP8 particle vaccine is being determined using a murine RV challenge model in Applicant's lab, the presented data in this report strongly supported the notion that the S60-VP8 particle is a promising vaccine candidate against RV infection and thus the S60 particle is an excellent platform for antigen display for novel vaccine development.

Native NoV capsids are made by 180 VP1s that are the single major structural protein of NoVs. In vitro expression of NoV VP1 via a eukaryotic system often resulted in a mixture of 180- and 60-valent VLPs and the two VLP formats were exchangeable via artificial denature and renature treatments [60]. Although it has not yet been thoroughly studied, previous expression of truncated S domains via the baculovirus/insect cell system appeared to self-assemble 180-valent S particles [11, 24]. However, unified 60-valent NoV VLPs or S particles via an expression system has never been produced previously. Therefore, Applicant's production technology of unified NoV S60 particles via the simple *E. coli* system represents a bioengineering advancement. The self-formation of the unified S60 particles may result from the combined impacts of the heavily modified S domain and the unique folding environment of the prokaryotic *E. coli* expression system. Homogenous complexity and size of a vaccine candidate is an important consideration for quality control, because variations in vaccine complexity and size will lead to variations in immunization outcomes of the vaccine.

Artificially introduced inter-molecular disulfide bonds may be used as a general approach to stabilize a viral protein particle or complex. During Applicant's previous construction of NoV P particles, Applicant found that addition of a cysteine-containing peptide to the end of NoV P domain promoted and stabilized P particle formation via inter-P dimer disulfide bonds [20-23]. In this current study, the S60 particles self-assembled efficiently (FIG. 3D), but the formation efficiency of the original version of the S60-VP8 particles were relatively low (FIG. 5C), due to an addition of the VP8 antigen. Remarkably, the self-formation efficiency of the S60-VP8 particles was significantly enhanced by introducing inter-S domain disulfide bonds. This was achieved by two basic steps. First, Applicant analyzed the shell structure of a GII.4 NoV (Wen Jiang, unpublished data) to identify two pairs of sterically close (5.7 to 5.9 Å) residues (V57/M140' and Q58/S136') between two adjacent S domains (FIGS. 6, A and B). Then two to four of these residues were mutated into cysteines simultaneously in different combinations: 1) V57C/M140'C, 2) Q58C/S136'C, 3) V57C/Q58C/S136'C, 4) V57C/Q58C/S140'C, and 5) V57C/Q58C/S136'C/S140'C, followed by production and measurement the self-formation efficiency of the resulted S60-VP8 particles.

Among these mutations, the S60-VP8 particles with the triple cysteine mutations (V57C/Q58C/S136'C) exhibited the highest particle formation efficiency with >95% the S-VP8 proteins self-assembling into the S60-VP8 particles (FIG. 6, F to J). The dimer and monomer forms of the mutated S-VP8 proteins were completely gone (compared FIG. 6H with FIG. 5C and FIG. E). Applicant also noted that the S60-VP8 particles with quadruple cysteine mutations (V57C/Q58C/S136'C/M140'C) exhibited nearly the same high efficiency of S60-VP8 particle formation as the ones with the triple cysteine mutations (data not shown). However, the detailed structural bases or mechanisms behind these different outcomes among various cysteine mutation combinations remain elusive. These results and Applicant's previous studies on the P particles [20-23] suggested that introduction of inter-molecular disulfide bonds may be utilized as a general approach to promote and stabilize a viral protein particle or complex formation. According to these data, the S60-VP8 particles with the R69A and V57C/Q58C/S136'C mutations was used to perform downstream experiments, while the modified S domain with the same mutations was and will be used to produce the stable S60 particles as a platform to display other antigens.

The S60- and S60-VP8 particles in this study were purified via a small Hisx6 peptide that was linked to the exposed C-terminus of the S domain or the S-VP8 protein. Applicant's data showed that the GST tag is not suitable for the S60- and S60-VP8 particle production, because it is large (220 residues), disturbing the S60 particle formation, and thus needs to be removed by an extra thrombin cleavage step, greatly complicating the purification procedure. In addition, we also tested the possibility of a tag-free purification method. Applicant found that the both S60 and S60-VP8 particles can be selectively precipitated by ammonium sulfate and resolved in PBS and other buffers (data not shown). Finally, Applicant discovered that the S60 and the S60-VP8 particles were eluted as a single peak through the gel-filtration size exclusion column and in anion exchange chromatography (data not shown). These data collectively indicated that the S60 and the S60-VP8 particles, and most likely other S60-antigen chimeric particles can be purified through a tag-free approach.

The 60 freely exposed C-termini are another feature facilitating the S60 particle to be a useful vaccine platform. Foreign antigens or epitopes can simply be fused to the end of the S domain via a flexible linker through recombinant DNA technology. This study showed clearly that the Hisx6 peptide and the RV VP8 antigen can be presented well by the S60 particle, as shown by the structural stability of the S60-Hisx6 and the S60-VP8 particles, as well as by their excellent binding abilities to the TALON CellThru Resin (Hisx6) and the H1 and Leb ligands (RV VP8). In addition, the fact that several other tested antigens or epitopes can be well presented by the S60 particles indicate the S60 particles as a multifunctional vaccine platform.

The modeling of the S60 particle, the S60-Hisx6 using the crystal structure of the 60 valent FCV VLP and the reconstruction of the 3-D structures of the S60-VP8 particle via cryoEM technology provide new insights into the structural basis of how the S60 particle displays the Hsix6 peptide and the RV VP8 antigen. Fitting the structure of the S60 particle model into the S60 particle region, as well as 60 copies of VP8 antigens into the protruding regions of the S60-VP8 particle cryoEM density map shed further light on the structural relationship between the S60 particle and their displayed antigens. These structural data will help design and understanding of future presentations of other foreign antigens by the S60 particle. Finally, these structural studies also confirmed the 60 valent T=1 icosahedral symmetry of the S60 particles and the S60-VP8 particles.

In summary, we have developed a self-assembled, polyvalent protein nanoparticle featured with easy production, high stability, and high immunogenicity, serving as an ideal platform for antigen display. As a proof of concept, a chimeric S60 particle displaying 60 copies of RV neutralizing VP8 antigens has been constructed. Applicant's data indicated that the highly immunogenic S60-VP8 particle is a promising vaccine candidate against RV infection and that the S60 particle is a multifunctional platform to enhance immunogenicity of various antigens for novel vaccine development against different pathogens.

REFERENCES

[1] Tan M, Jiang X. Norovirus P particle: a subviral nanoparticle for vaccine development against norovirus, rotavirus and influenza virus. Nanomedicine (Lond) 2012; 7:889-97.
[2] Tan M, Jiang X. Subviral particle as vaccine and vaccine platform. Current opinion in virology 2014; 6C:24-33.
[3] Tan M, Jiang X. Recent Advancements in Combination Subunit Vaccine Development. Human vaccines & immunotherapeutics 2016:0.
[4] Patel M M, Widdowson M A, Glass R I, Akazawa K, Vinje J, Parashar U D. Systematic literature review of role of noroviruses in sporadic gastroenteritis. Emerg Infect Dis 2008; 14:1224-31.
[5] Glass R I, Noel J, Mitchell D, Herrmann J E, Blacklow N R, Pickering L K, et al. The changing epidemiology of astrovirus-associated gastroenteritis: a review. Archives of virology Supplementum 1996; 12:287-300.
[6] Prasad B V, Hardy M E, Dokland T, Bella J, Rossmann M G, Estes MK. X-ray crystallographic structure of the Norwalk virus capsid. Science 1999; 286:287-90.
[7] Bu W, Mamedova A, Tan M, Xia M, Jiang X, Hegde R S. Structural basis for the receptor binding specificity of Norwalk virus. J Virol 2008; 82:5340-7.
[8] Cao S, Lou Z, Tan M, Chen Y, Liu Y, Zhang Z, et al. Structural basis for the recognition of blood group trisaccharides by norovirus. J Virol 2007; 81:5949-57.
[9] Chen Y, Tan M, Xia M, Hao N, Zhang X C, Huang P, et al. Crystallography of a lewis-binding norovirus, elucidation of strain-specificity to the polymorphic human histo-blood group antigens. PLoS pathogens 2011; 7:e1002152.
[10] Choi J M, Hutson A M, Estes M K, Prasad B V. Atomic resolution structural characterization of recognition of histo-blood group antigens by Norwalk virus. Proceedings of the National Academy of Sciences of the United States of America 2008; 105:9175-80.
[11] Tan M, Hegde R S, Jiang X. The P domain of norovirus capsid protein forms dimer and binds to histo-blood group antigen receptors. J Virol 2004; 78:6233-42.
[12] Tan M, Jiang X. Norovirus gastroenteritis, carbohydrate receptors, and animal models. PLoS pathogens 2010; 6:e 1000983.
[13] Tan M, Jiang X. Norovirus-host interaction: Multi-selections by human histo-blood group antigens. Trends in microbiology 2011; 19:382-8.
[14] Tan M, Jiang X. Histo-blood group antigens: a common niche for norovirus and rotavirus. Expert Rev Mol Med 2014; 16:e5.
[15] Huang P, Farkas T, Zhong W, Tan M, Thornton S, Morrow A L, et al. Norovirus and histo-blood group antigens: demonstration of a wide spectrum of strain specificities and classification of two major binding groups among multiple binding patterns. J Virol 2005; 79:6714-22.
[16] Liu W, Chen Y, Jiang X, Xia M, Yang Y, Tan M, et al. A Unique Human Norovirus Lineage with a Distinct HBGA Binding Interface. PLoS Pathog 2015; 11:e1005025.
[17] Shanker S, Choi J M, Sankaran B, Atmar R L, Estes M K, Prasad B V. Structural analysis of histo-blood group antigen binding specificity in a norovirus GII.4 epidemic variant: implications for epochal evolution. J Virol 2011; 85:8635-45.
[18] Shanker S, Czako R, Sankaran B, Atmar R L, Estes M K, Prasad B V. Structural analysis of determinants of histo-blood group antigen binding specificity in genogroup I noroviruses. J Virol 2014; 88:6168-80.
[19] Hansman G S, Biertumpfel C, Georgiev I, McLellan J S, Chen L, Zhou T, et al. Crystal Structures of GII. 10 and GII.12 Norovirus Protruding Domains in Complex with Histo-Blood Group Antigens Reveal Details for a Potential Site of Vulnerability. J Virol 2011; 85:6687-701.
[20] Tan M, Fang P A, Xia M, Chachiyo T, Jiang W, Jiang X. Terminal modifications of norovirus P domain resulted in a new type of subviral particles, the small P particles. Virology 2011; 410:345-52.
[21] Tan M, Fang P, Chachiyo T, Xia M, Huang P, Fang Z, et al. Noroviral P particle: Structure, function and applications in virus-host interaction. Virology 2008; 382:115-23.
[22] Tan M, Jiang X. The p domain of norovirus capsid protein forms a subviral particle that binds to histo-blood group antigen receptors. Journal of Virology 2005; 79:14017-30.
[23] Bereszczak J Z, Barbu I M, Tan M, Xia M, Jiang X, van Duijn E, et al. Structure, stability and dynamics of norovirus P domain derived protein complexes studied by native mass spectrometry. Journal of structural biology 2012; 177:273-82.
[24] Bertolotti-Ciarlet A, White I J, Chen R, Prasad B V, Estes M K. Structural requirements for the assembly of Norwalk virus-like particles. J Virol 2002; 76:4044-55.
[25] Tate J E, Burton A H, Boschi-Pinto C, Steele A D, Duque J, Parashar U D, et al. 2008 estimate of worldwide rotavirus-associated mortality in children younger than 5 years before the introduction of universal rotavirus vaccination programmes: a systematic review and meta-analysis. Lancet Infect Dis 2012; 12:136-41.
[26] Parashar U D, Gibson C J, Bresse J S, Glass R I. Rotavirus and severe childhood diarrhea. Emerg Infect Dis 2006; 12:304-6.
[27] Walker C L, Rudan I, Liu L, Nair H, Theodoratou E, Bhutta Z A, et al. Global burden of childhood pneumonia and diarrhoea. Lancet 2013; 381:1405-16.

[28] Vesikari T, Itzler R, Matson D O, Santosham M, Christie C D, Coia M, et al. Efficacy of a pentavalent rotavirus vaccine in reducing rotavirus-associated health care utilization across three regions (I countries). Int J Infect Dis 2007; 11 Suppl 2:S29-35.
[29] Yen C, Tate J E, Patel M M, Cortese M M, Lopman B, Fleming J, et al. Rotavirus vaccines: update on global impact and future priorities. Human vaccines 2011; 7:1282-90.
[30] Zaman K, Dang D A, Victor J C, Shin S, Yunus M, Dallas M J, et al. Efficacy of pentavalent rotavirus vaccine against severe rotavirus gastroenteritis in infants in developing countries in Asia: a randomised, double-blind, placebo-controlled trial. Lancet 2010; 376:615-23.
[31] Madhi S A, Cunliffe N A, Steele D, Witte D, Kirsten M, Louw C, et al. Effect of human rotavirus vaccine on severe diarrhea in African infants. N Engl J Med 2010; 362:289-98.
[32] Armah G E, Sow S O, Breiman R F, Dallas M J, Tapia M D, Feikin D R, et al. Efficacy of pentavalent rotavirus vaccine against severe rotavirus gastroenteritis in infants in developing countries in sub-Saharan Africa: a randomised, double-blind, placebo-controlled trial. Lancet 2010; 376:606-14.
[33] Liu Y, Ramelot T A, Huang P, Liu Y, Li Z, Feizi T, et al. Glycan Specificity of P[19] Rotavirus and Comparison with Those of Related P Genotypes. J Virol 2016; 90:9983-96.
[34] Jiang X, Liu Y, Tan M. Histo-blood group antigens as receptors for rotavirus, new understanding on rotavirus epidemiology and vaccine strategy. Emerging Microbes & Infections 2017; 6.
[35] Desai R, Cortese M M, Meltzer M I, Shankar M, Tate J E, Yen C, et al. Potential intussusception risk versus benefits of rotavirus vaccination in the United States. The Pediatric infectious disease journal 2013; 32:1-7.
[36] Bauchau V, Van Holle L, Mahaux O, Holl K, Sugiyama K, Buyse H. Post-marketing monitoring of intussusception after rotavirus vaccination in Japan. Pharmacoepidemiology and drug safety 2015; 24:765-70.
[37] Yung C-F, Chan S P, Soh S, Tan A, Thoon K C. Intussusception and Monovalent Rotavirus Vaccination in Singapore: Self-Controlled Case Series and Risk-Benefit Study. The Journal of pediatrics 2015; 167:163-8.e 1.
[38] Rosillon D, Buyse H, Friedland L R, Ng S-P, Velazquez F R, Breuer T. Risk of Intussusception After Rotavirus Vaccination: Meta-analysis of Postlicensure Studies. The Pediatric infectious disease journal 2015; 34:763-8.
[39] Yih W K, Lieu T A, Kulldorff M, Martin D, McMahill-Walraven C N, Platt R, et al. Intussusception risk after rotavirus vaccination in U.S. infants. The New England journal of medicine 2014; 370:503-12.
[40] Weintraub E S, Baggs J, Duffy J, Vellozzi C, Belongia E A, Irving S, et al. Risk of intussusception after monovalent rotavirus vaccination. The New England journal of medicine 2014; 370:513-9.
[41] Glass R I, Parashar U D. Rotavirus vaccines—balancing intussusception risks and health benefits. The New England journal of medicine 2014; 370:568-70.
[42] Settembre E C, Chen J Z, Dormitzer P R, Grigorieff N, Harrison S C. Atomic model of an infectious rotavirus particle. EMBO J 2011; 30:408-16.
[43] Hu L, Crawford S E, Czako R, Cortes-Penfield N W, Smith D F, Le Pendu J, et al. Cell attachment protein VP8* of a human rotavirus specifically interacts with A-type histo-blood group antigen. Nature 2012; 485: 256-9.
[44] Hu L, Ramani S, Czako R, Sankaran B, Yu Y, Smith D F, et al. Structural basis of glycan specificity in neonate-specific bovine-human reassortant rotavirus. Nat Commun 2015; 6:8346.
[45] Huang P, Xia M, Tan M, Zhong W, Wei C, Wang L, et al. Spike protein VP8* of human rotavirus recognizes histo-blood group antigens in a type-specific manner. J Virol 2012; 86:4833-43.
[46] Tan M, Huang P, Xia M, Fang P A, Zhong W, McNeal M, et al. Norovirus P particle, a novel platform for vaccine development and antibody production. J Virol 2011; 85:753-64.
[47] Xia M, Wei C, Wang L, Cao D, Meng X J, Jiang X, et al. Development and evaluation of two subunit vaccine candidates containing antigens of hepatitis E virus, rotavirus, and astrovirus. Sci Rep 2016; 6:25735.
[48] Groome M J, Koen A, Fix A, Page N, Jose L, Madhi S A, et al. Safety and immunogenicity of a parenteral P2-VP8-P[8] subunit rotavirus vaccine in toddlers and infants in South Africa: a randomised, double-blind, placebo-controlled trial. Lancet Infect Dis 2017; 17:843-53.
[49] Wen X B, Cao D J, Jones R W, Hoshino Y, Yuan L J. Tandem truncated rotavirus VP8*subunit protein with T cell epitope as non-replicating parenteral vaccine is highly immunogenic. Human vaccines & immunotherapeutics 2015; 11:2483-9.
[50] Du J, Lan Z, Liu Y, Liu Y, Li Y, Li X, et al. Detailed analysis of BALB/c mice challenged with wild type rotavirus EDIM provide an alternative for infection model of rotavirus. Virus research 2017; 228:134-40.
[51] Doud M B, Koksal A C, Mi L Z, Song G, Lu C, Springer T A. Unexpected fold in the circumsporozoite protein target of malaria vaccines. Proceedings of the National Academy of Sciences of the United States of America 2012; 109:7817-22.
[52] Xia M, Tan M, Wei C, Zhong W, Wang L, McNeal M, et al. A candidate dual vaccine against influenza and noroviruses. Vaccine 2011; 29:7670-7.
[53] Wang L, Huang P, Fang H, Xia M, Zhong W, McNeal M M, et al. Polyvalent complexes for vaccine development. Biomaterials 2013; 34:4480-92.
[54] Wang L, Cao D, Wei C, Meng X J, Jiang X, Tan M. A dual vaccine candidate against norovirus and hepatitis E virus. Vaccine 2014; 32:445-52.
[55] Wang L, Xia M, Huang P, Fang H, Cao D, Meng X J, et al. Branched-linear and agglomerate protein polymers as vaccine platforms. Biomaterials 2014; 35:8427-38.
[56] Xia M, Wei C, Wang L, Cao D, Meng X J, Jiang X, et al. A trivalent vaccine candidate against hepatitis E virus, norovirus, and astrovirus. Vaccine 2016; 34:905-13.
[57] Tan M, Jiang X. The p domain of norovirus capsid protein forms a subviral particle that binds to histo-blood group antigen receptors. J Virol 2005; 79:14017-30.
[58] Liu Y, Huang P, Tan M, Liu Y, Biesiada J, Meller J, et al. Rotavirus VP8*: phylogeny, host range, and interaction with histo-blood group antigens. J Virol 2012; 86:9899-910.
[59] Burmeister W P, Buisson M, Estrozi L F, Schoehn G, Billet O, Hannas Z, et al. Structure determination of feline calicivirus virus-like particles in the context of a pseudo-octahedral arrangement. PLoS One 2015; 10:e0119289.

[60] White L U, Hardy M E, Estes M K. Biochemical characterization of a smaller form of recombinant Norwalk virus capsids assembled in insect cells. J Virol 1997; 71:8066-72.

[61] Shoemaker G K, van Duijn E, Crawford S E, Uetrecht C, Baclayon M, Roos W H, et al. Norwalk virus assembly and stability monitored by mass spectrometry. Molecular & cellular proteomics: MCP 2010; 9:1742-51.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A polyvalent icosahedral composition for antigen presentation comprising an S particle, wherein said S particle comprises a recombinant fusion protein comprising a) a norovirus (NoV) S domain protein comprising a mutation at position 69, and a mutation selected from 57C/140C, 57C/58C/136C, and 57C/58C/136C/140C;

b) a linker protein domain operatively connected to said norovirus S domain protein; and c) an antigen protein domain operatively connected to said linker;

wherein said mutations are with reference to SEQ ID NO: 25;

wherein said mutation at position 69 renders a cleavage site between R69 and N70 resistant to trypsin cleavage; and wherein said norovirus is a human calicivirus.

2. The polyvalent icosahedral composition of claim 1, wherein said composition has an icosahedral symmetry structure.

3. The polyvalent icosahedral composition of claim 1, wherein said composition comprises 60 sites for antigen presentation.

4. The polyvalent icosahedral composition of claim 1, wherein said norovirus S domain protein comprises a mutation sufficient to provide a non-native disulfide bond binding site.

5. The polyvalent icosahedral composition of claim 1, wherein said norovirus S domain protein comprises a mutation of at least two amino acids sufficient to provide at least one non-native disulfide bond binding site, or at least two non-native disulfide bond binding sites, or at least three non-native disulfide bond binding sites between neighboring S domain proteins of the polyvalent icosahedral S particle.

6. The polyvalent icosahedral composition of claim 1, wherein said calicivirus has 180 copies of a single capsid protein.

7. The polyvalent icosahedral composition of claim 1, wherein said linker comprises three to six amino acids.

8. The polyvalent icosahedral composition of claim 1, wherein said antigen protein domain comprises an antigen having a size of from 8 amino acids up to about 300 amino acids, or from 8 amino acids up to about 400 amino acids, or from 8 amino acids up to about 500 amino acids.

9. The polyvalent icosahedral composition of claim 1, wherein said antigen protein domain comprises a rotavirus (RV) antigen.

10. The polyvalent icosahedral composition of claim 1, wherein said antigen protein domain comprises an RV spike protein antigen (VP8 antigen).

11. The polyvalent icosahedral composition of claim 1, wherein said antigen protein domain comprises an antigen selected from a TSR antigen of circumsporozoite protein (CSP) of malaria parasite Plasmodium falciparum, a receptor-binding domain of the HA1 protein and an M2e epitope of influenza A virus, a P domain antigen of hepatitis E, a surface spike protein of the astrovirus, and combinations thereof.

12. A recombinant fusion protein comprising a) a norovirus (NoV) S domain protein comprising a mutation at position 69, and a mutation selected from 57C/140C, 57C/58C/136C, and 57C/58C/136C/140C;

b) a linker protein domain operatively connected to said norovirus S domain protein; and c) an antigen protein domain operatively connected to said linker;

wherein said mutation at position 69 renders a cleavage site between R69 and N70 resistant to trypsin cleavage;

wherein said mutations are with reference to SEQ ID NO: 25; and wherein said norovirus is a human calicivirus.

13. A method of making the polyvalent icosahedral structure of claim 1, comprising the steps of a) making a first region comprising a norovirus (NoV) S domain protein comprising a mutation at position 69, and a mutation selected from 57C/140C, 57C/58C/136C, and 57C/58C/136C/140C and b) recombinantly expressing said first region with a linker and an antigen, wherein said mutations are with reference to SEQ ID NO: 25.

14. The method of claim 13, wherein said composition is produced in *E.coli*.

15. A method of eliciting an immune response in an individual in need thereof, comprising the step of administering a composition according to claim 1.

16. A container comprising at least one dose of composition according to claim 1.

17. A kit comprising one or more containers according to claim 16, a delivery device, and instructions for administration of said composition.

18. The composition of claim 1 wherein said mutation at position 69 is an R69A mutation.

* * * * *